US007585500B2

(12) United States Patent
Foltz et al.

(10) Patent No.: US 7,585,500 B2
(45) Date of Patent: Sep. 8, 2009

(54) FULLY HUMAN MONOCLONAL ANTIBODIES TO IL-13

(75) Inventors: Ian Foltz, Burnaby (CA); Raffaella Faggioni, Pleasanton, CA (US); Giorgio Senaldi, Dublin, CA (US); Kathy Manchulenko, Port Coquitlam (CA); Jaspal S. Kang, British Columbia (CA); Palaniswami Rathanaswami, Vancouver (CA); Kiran Ahluwalia, Fremont, CA (US); Orit Foord, Foster City, CA (US); Scott Klakamp, Fremont, CA (US)

(73) Assignee: Amgen Inc., Thousand Oaks, CA (US)

( * ) Notice: Subject to any disclaimer, the term of this patent is extended or adjusted under 35 U.S.C. 154(b) by 552 days.

(21) Appl. No.: 11/281,266

(22) Filed: Nov. 16, 2005

(65) Prior Publication Data

US 2006/0140948 A1 Jun. 29, 2006

Related U.S. Application Data

(60) Provisional application No. 60/629,135, filed on Nov. 17, 2004, provisional application No. 60/728,604, filed on Oct. 19, 2005.

(51) Int. Cl.
*A61K 39/395* (2006.01)
*C07K 16/24* (2006.01)

(52) U.S. Cl. ............. 424/130.1; 424/133.1; 424/135.1; 424/139.1; 424/141.1; 424/142.1; 424/145.1; 424/158.1; 530/387.1; 530/387.3; 530/387.9; 530/388.1; 530/388.15; 530/388.23; 530/389.1; 530/389.2

(58) Field of Classification Search .................. None
See application file for complete search history.

(56) References Cited

U.S. PATENT DOCUMENTS

| | | | |
|---|---|---|---|
| 5,596,072 A | 1/1997 | Culpepper et al. |
| 5,652,123 A | 7/1997 | Caput et al. |
| 5,696,234 A | 12/1997 | Zurawski et al. |
| 5,710,023 A | 1/1998 | Collins et al. |
| 5,783,181 A | 7/1998 | Browne et al. |
| 5,830,453 A | 11/1998 | Badr et al. |
| 5,919,456 A | 7/1999 | Puri et al. |
| 5,939,598 A | 8/1999 | Kucherlapati et al. |
| 6,075,181 A | 6/2000 | Kucherlapati et al. |
| 6,114,598 A | 9/2000 | Kucherlapati et al. |
| 6,143,871 A | 11/2000 | Bonnefoy et al. |
| 6,150,584 A | 11/2000 | Kucherlapati et al. |
| 6,162,963 A | 12/2000 | Kucherlapati et al. |
| 6,214,559 B1 | 4/2001 | Collins et al. |
| 6,248,714 B1 | 6/2001 | Collins et al. |
| 6,268,480 B1 | 7/2001 | Collins et al. |
| 6,407,218 B1 | 6/2002 | Tamarkin et al. |
| 6,468,528 B1 | 10/2002 | Mak et al. |
| 6,495,331 B1 | 12/2002 | Gelfand et al. |
| 6,511,848 B2 | 1/2003 | Jungfer et al. |
| 6,518,061 B1 | 2/2003 | Puri et al. |
| 6,599,914 B2 | 7/2003 | Schleimer et al. |
| 6,638,621 B2 | 10/2003 | Anderson |
| 6,656,695 B2 | 12/2003 | Berg et al. |
| 6,676,939 B2 | 1/2004 | Hurst et al. |
| 6,746,839 B1 | 6/2004 | Duff et al. |
| 6,811,780 B2 | 11/2004 | Furfine et al. |
| 6,824,986 B1 | 11/2004 | Finkelman et al. |
| 2002/0197266 A1 | 12/2002 | Debinski |
| 2003/0013851 A1 | 1/2003 | Powers |
| 2003/0031666 A1 | 2/2003 | Debinski et al. |
| 2003/0044975 A1 | 3/2003 | Rossjohn et al. |
| 2003/0118546 A1 | 6/2003 | Wei et al. |
| 2003/0129132 A1 | 7/2003 | Puri et al. |
| 2003/0129166 A1 | 7/2003 | Irvine et al. |
| 2003/0134419 A1 | 7/2003 | Steinman et al. |
| 2003/0138433 A1 | 7/2003 | Newell et al. |
| 2003/0143199 A1 | 7/2003 | Carson et al. |
| 2003/0143658 A1 | 7/2003 | Casella |
| 2003/0165887 A1 | 9/2003 | Reed |
| 2003/0170203 A1 | 9/2003 | Yu |
| 2003/0175898 A1 | 9/2003 | Pantelidis |
| 2003/0180252 A1 | 9/2003 | Tamarkin |

(Continued)

FOREIGN PATENT DOCUMENTS

EP 0 506 574 A1 3/1992

(Continued)

OTHER PUBLICATIONS

U.S. Appl. No. 10/058,393.
U.S. Appl. No. 07/466,008, filed Jan. 12, 1990.
U.S. Appl. No. 07/610,515, filed Nov. 8, 1990.
U.S. Appl. No. 07/919,297, filed Jul. 24, 1992.
U.S. Appl. No. 07/922,649, filed Jul. 30, 1992.
U.S. Appl. No. 08/031,801, filed Mar. 15, 1993.
U.S. Appl. No. 08/112,848, filed Aug. 27, 1993.
U.S. Appl. No. 08/234,145, filed Apr. 28, 1994.
U.S. Appl. No. 08/376,279, filed Jan. 20, 1995.
U.S. Appl. No. 08/430,938, filed Apr. 27, 1995.
U.S. Appl. No. 08/464,584, filed Jun. 5, 1995.

(Continued)

*Primary Examiner*—Jeffrey Stucker
*Assistant Examiner*—Stephen Gucker
(74) *Attorney, Agent, or Firm*—Nathan A. Machin

(57) ABSTRACT

The present invention is related to antibodies directed to IL-13 and uses of such antibodies. For example, in accordance with the present invention, there are provided human monoclonal antibodies directed to IL-13. Isolated polynucleotide sequences encoding, and amino acid sequences comprising, heavy and light chain immunoglobulin molecules, particularly sequences corresponding to contiguous heavy and light chain sequences spanning the framework regions (FR's) and/or complementarity determining regions (CDR's), are provided. Additionally, methods of using these antibodies to treat patients are also provided. Additionally, IL-13 dependent biomarkers and methods of their identification and use are also provided.

3 Claims, 33 Drawing Sheets

U.S. PATENT DOCUMENTS

| | | | |
|---|---|---|---|
| 2003/0211104 A1 | 11/2003 | Furfine et al. | |
| 2003/0235555 A1 | 12/2003 | Shealy et al. | |
| 2004/0023337 A1 | 2/2004 | Heavner et al. | |
| 2004/0028650 A1 | 2/2004 | Van Snick | |
| 2004/0030097 A1 | 2/2004 | Serrano et al. | |
| 2004/0115194 A1 | 6/2004 | Wang | |
| 2004/0234499 A1* | 11/2004 | Shealy et al. | 424/85.1 |
| 2004/0248260 A1 | 12/2004 | Heavner et al. | |
| 2005/0065237 A1 | 3/2005 | Schmidt | |
| 2005/0065327 A1* | 3/2005 | Monk et al. | 530/388.23 |
| 2005/0096268 A1 | 5/2005 | Wynn | |
| 2005/0169901 A1 | 8/2005 | Pang | |
| 2005/0266005 A1 | 12/2005 | Heavner | |
| 2006/0024306 A1 | 2/2006 | Strober et al. | |
| 2006/0063228 A1 | 3/2006 | Kasaian et al. | |
| 2006/0073148 A1 | 4/2006 | Tchistiakova et al. | |
| 2008/0171014 A1 | 7/2008 | Wu et al. | |

FOREIGN PATENT DOCUMENTS

| | | |
|---|---|---|
| EP | 0621341 A2 | 4/1994 |
| EP | 0 463 151 B1 | 6/1996 |
| EP | 1327681 A1 | 7/2003 |
| JP | 3 068 180 B2 | 3/1991 |
| JP | 3 086 506 B2 | 3/1991 |
| JP | 3 086 507 B2 | 3/1991 |
| WO | WO 94/02602 | 2/1994 |
| WO | WO 94/04680 | 3/1994 |
| WO | WO 96/04388 | 2/1996 |
| WO | WO 96/29417 | 9/1996 |
| WO | WO 96/34096 | 10/1996 |
| WO | WO 97/15663 | 5/1997 |
| WO | WO 97/20926 | 6/1997 |
| WO | WO 98/10638 | 3/1998 |
| WO | WO 98/24893 | 6/1998 |
| WO | WO 98/31384 | 7/1998 |
| WO | WO 00/40264 | 1/2000 |
| WO | WO 00/36103 A1 | 6/2000 |
| WO | WO 00/62736 | 10/2000 |
| WO | WO 00/64944 | 11/2000 |
| WO | WO 00/76310 | 12/2000 |
| WO | WO 01/08660 | 2/2001 |
| WO | WO 02/055100 A2 | 7/2002 |
| WO | WO 02/056902 | 7/2002 |
| WO | WO 02/056905 | 7/2002 |
| WO | WO 02/085308 | 10/2002 |
| WO | WO 02/085309 | 10/2002 |
| WO | WO 02/100432 | 12/2002 |
| WO | WO 03/034984 | 5/2003 |
| WO | WO 03/035847 | 5/2003 |
| WO | WO 03/058201 | 7/2003 |
| WO | WO 03/068799 | 8/2003 |
| WO | WO 03/086451 | 10/2003 |
| WO | WO 03/090776 | 11/2003 |
| WO | WO 03/092610 | 11/2003 |
| WO | WO 2004/001655 | 12/2003 |
| WO | WO 2004/015070 | 2/2004 |
| WO | WO 2004/019974 | 3/2004 |
| WO | WO 2004/022096 | 3/2004 |
| WO | WO 2004/069274 | 8/2004 |
| WO | WO 2004/090539 | 10/2004 |
| WO | WO 2004/092404 | 10/2004 |
| WO | WO 2004/094458 | 11/2004 |
| WO | WO 2005/007699 A2 | 1/2005 |
| WO | WO 2005062967 A2 * | 7/2005 |
| WO | WO 2005/091853 | 10/2005 |
| WO | WO 2006/003407 | 1/2006 |

OTHER PUBLICATIONS

U.S. Appl. No. 08/464,582, filed Jun. 5, 1995.
U.S. Appl. No. 08/463,191, filed Jun. 5, 1995.
U.S. Appl. No. 08/462,837, filed Jun. 5, 1995.
U.S. Appl. No. 08/486,853, filed Jun. 5, 1995.
U.S. Appl. No. 08/486,859, filed Jun. 5, 1995.
U.S. Appl. No. 08/462,513, filed Jun. 5, 1995.
U.S. Appl. No. 08/724,752, filed Oct. 2, 1996.
U.S. Appl. No. 08/759,620, filed Dec. 3, 1996.
Bost, et al. "In Vivo Treatment with Anti-Interleukin-13 Antibodies Significantly Reduces the Humoral Immune Response Against an Oral Immunogen In Mice" *Immunology*, Blackwell Publishing, Oxford, GB, vol. 87, 1996, pp. 633-641.
Blease et al., "Therapeutic Effect of IL-13 Immunoneutralization During Chronic Experimental Fungal Asthma,", *The Journal of Immunology*, 5219-5224 (2001).
Green et al., *Nature Genetics* 7:13-21 (1994).
Heinzmann et al., "Genetic Variants of IL-13 Signalling and Human Asthma and Atopy" *Human Molecular Genetics*, vol. 9, No. 4, pp. 549-559, Oxford University Press (2000).
Tekkanat et al., "IL-13-Induced Airway Hyperreactivity During Respiratory Syncytial Virus Infection is STAT6 Dependent," *The Journal of Immunology* 3542-3548 (2001).
Yang, et al., "Anti-IL-13 Monoclonal Antibody Inhibits Airway Hyperresponsiveness, Inflammation and Airway Remodeling," *Cytokine* 28 224-232 (2004).
Skinnider, et al. "Interleukin 13 and interleukin 13 receptor are frequently expressed by Hodgkin and Reed-Sternberg cells of Hodgkin lymphoma" *Blood*, Jan. 1, 2001- vol. 97, No. 1 2001 by the American Society of Hematology.
Mckenzie, et al.. "Interleukin 13, a T-cell-derived cytokine that regulates human monocyte and B-cell function" Proc.Natl. Acad. Sci. USA vol. 90, pp. 3735-3739, Apr. 1993 Immunology.
Males, Maria et al. "Real-time polymerase chain reaction determination of cytokine mRNA expression profiles in Hodgkin's lymphoma" *Haematologica*, Jun. 2006, 89(6): 678-685.
Arima et al., "Upregulation of IL-13 concentration in vivo by the IL13 variant associated with bronchial asthma," *J Allergy Clin Immunol* 109(6) pp. 980-987 (2002).
Babcook et al., "A novel strategy for generating monoclonal antibodies from single, isolated lymphocytes producing antibodies of defined specificities," *Proc. Natl. Acad. Sci. USA*, 93:7843-7848 (1996).
Charman W.N. "Lipids, Lipophilic Drugs, and Oral Drug Delivery -Some Emerging Concepts," *J. Pharm. Sci.* 89(8):967-78 (2000).
Graves et al., "A cluster of seven tightly linked polymorphisms in the IL-13 gene is associated with total serum IgE levels in three populations of white children," *J Allergy Clin Immunol*, 105(3) pp. 506-513 (2000).
Howard, T.D. et al., "Gene-Gene Interaction in Asthma: IL4RA and IL13 in a Dutch Population with Asthma," *Am J Hum Genet*, 70(1) pp. 230-236 (2002).
Kauppi et al., "A Second-Generation Association Study of the 5q31 Cytokine Gene Cluster and the interleukin-4 Receptor in Asthma," *Genomics* 77(1-2) pp. 35-42 (2001).
Ma et al., "The C10-CCL6 Chemokine and CCR1 Play Critical Roles in the Pathogenesis of IL-13-Induced Inflammation and Remodeling," *J Immunol.*, 172(3):1872-81 (2004).
Nomura et al. Interleukin-13 Induces Thymus and Activation-Regulated Chemokine (CCL17) in Human Peripheral Blood Mononuclear Cells, *Cytokine*, 20(2):49-55 (2002).
Powell et al., "Compendium of Excipients for Parenteral Formulations" *PDA J. Pharm. Sci. Technol*. 52:238-311 (1998).
Punnonen et al., Interleukin 13 Induces Interleukin 4-Independent IgG4 and IgE Synthesis and CD23 Expression by Human B Cells, *Proc Natl Acad Sci USA*, 90:3730-3734 (1993).
"Remington: The Science and Practice of Pharmacy" $20^{th}$ ed., Lippincott Williams & Wilkens Publishers, Baltimore, Maryland, USA (2000).
Van Der Pouw Kraan et al., "An IL-13 Promoter Polymorphism Associated with Increased Risk of Allergic Asthma," *Genes Immun*. 1(1) pp. 61-65 (1999).
Wang W., "Lyophilization and Development of Solid Protein Pharmaceuticals" *Int. J. Pharm*. 203(1-2):1-60 (2000).
Wills-Karp M., "Interleukin-13 in Asthma," *Curr. Opin. Pulm. Med.* 9-21-27 (2003).

Willis-Karp M., "Murine Models of Asthma in Understanding Dysregulation in Human Asthma," *Immunopharmacology*, 25:48:263-8 (2000).

Wynn T.A., "IL-13 Effector Functions," *Annu. Rev. Immunol.* 21:425-456 (2003).

Zhu et al., "IL-13-Induced Chemokine Responses in the Lung: Role of CCR2 in the Pathogenesis of IL-13-Induced Inflammation and Remodeling," *J. Immunol.* 168(6):2953-362 (2002).

Zhu et al., "Pulmonary Expression of Interleukin-13 Causes Inflammation, Mucus Hypersecretion, Subepithelial Fibrosis, Physiologic Abnormalities, and Eotaxin Production," *J. Clin. Invest.* 103(6):779-88 (1999).

Communication Pursuant to Article 96(2) EPC, received in EP Application No. 05 823 172.1, dated Oct. 11, 2007, in 8 pages.

International Preliminary Report on Patentability, dated May 31, 2007, received in International Application No. PCT/US2005/041536, in 10 pages.

* cited by examiner

SEQ ID NO: 72

FIG. 10

GPVPPSTALRELIEELVNITQNQKAPLCNGSMVWSINLTAGMYCAALESLINVSGCSAIEKTQRMLSGFCPHKVSAG
QFSSLHVRDTKIEVAQFVKDLLHLKKLFREGRFN (SEQ ID NO: 96)

SEQUENCE LISTING

<160> NUMBER OF SEQ ID NOS: 96

<210> SEQ ID NO 1
<211> LENGTH: 366
<212> TYPE: DNA
<213> ORGANISM: Homo sapiens

<400> SEQUENCE: 1

```
caggtgcagc tggtggagtc tgggggaggc gtggtccagc ctgggaggtc cctgagactc      60
tcctgtgtag cgtctggatt caccttcagt agctatgaca tgcactgggt ccgccaggct     120
ccaggcaagg ggctggagtg ggtggcagtt atatggtatg atggaagtaa taaatactat     180
gcagactccg tgcagggccg attcaccatc tccagagaca attccaagaa cacgctgtat     240
ctgcaaatga acagcctgag agccgaggac acggctgtgt attactgtac gagcgaagat     300
agcagtggct ggtacgacgg ctggttcgac ccctggggcc agggaaccct ggtcaccgtc     360
tcctca                                                                366
```

<210> SEQ ID NO 2
<211> LENGTH: 122
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
  1               5                  10                  15

Ser Leu Arg Leu Ser Cys Val Ala Ser Gly Phe Thr Phe Ser Ser Tyr
             20                  25                  30

Asp Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ser Glu Asp Ser Ser Gly Trp Tyr Asp Gly Trp Phe Asp Pro Trp
            100                 105                 110

Gly Gln Gly Thr Leu Val Thr Val Ser Ser
        115                 120
```

<210> SEQ ID NO 3
<211> LENGTH: 321
<212> TYPE: DNA
<213> ORGANISM: Homo sapiens

<400> SEQUENCE: 3

```
gacatccaga tgacccagtc tccatcctcc ctgtctgcat ctgtaggaga cagagtcacc      60
atcacttgcc gggcgagtca gggcattagc aattatttag cctggtatca gcagaaacca     120
gggaaagttc ctaaggtcct gatctatgct gcatccactt tgcaatcagg ggtcccatct     180
cgattcagtg gcagtggatc tgggacagat ttcactctca ccatcagcag cctgcagcct     240
gaagatgttg caacttatta ctgtcaaaag tataacagtg ccccattcac tttcggccct     300
gggaccaaag tggatatcaa a                                                321
```

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys
            100                 105

<210> SEQ ID NO 5
<211> LENGTH: 360
<212> TYPE: DNA
<213> ORGANISM: Homo sapiens

<400> SEQUENCE: 5
caggtgcagc tgcaggagtc gggcccagga ctggtgaagc cttcggagac cctgtccctc      60
acctgcactg tctctggtgg ctccatcagt acttactact ggagctggat ccggcagccc     120
ccagggaagg gactggagtg gattgggtat atctattaca gtgggagcac caactacaat     180
ccctccctca agagtcgagt caccatatca gtagacacgt ccaagaacca gttctccctg     240
aagctgagct ctgtgaccgc tgcggacacg gccgtgtatt actgtgcgag agatggtgga     300
cactactggg atgatgcttt tgatatctgg ggccaaggga caatggtcac cgtctcttca     360

<210> SEQ ID NO 6
<211> LENGTH: 120
<212> TYPE: PRT
<213> ORGANISM: Homo sapiens

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Gly His Tyr Trp Asp Asp Ala Phe Asp Ile Trp Gly Gln
            100                 105                 110

Gly Thr Met Val Thr Val Ser Ser
        115                 120

<210> SEQ ID NO 7
<211> LENGTH: 321
<212> TYPE: DNA
<213> ORGANISM: Homo sapiens
<220> FEATURE:
<221> NAME/KEY: misc_feature
<222> LOCATION: 20, 68, 140, 205, 217, 232, 233, 240, 265
<223> OTHER INFORMATION: n = A,T,C or G

<400> SEQUENCE: 7

```
gacatccaga tgacccagtn tccatcctcc ctgtctgcat ctgtaggaga cagagtcacc    60
atcacttncc gggcaagtca gggcattaga aatgatttag actggtatca gcagaaacca   120
gggaaagccc ctaagcgccn gatctatgat gcatccagtt tgcaaagtgg ggtcccatca   180
aggttcagcg gcagtggatg tgggncagaa ttcactntca ctatcagcag cnngcagccn   240
gaagattttg caacttatta ctgtntacag catgatagtt acccattccc tttcggccct   300
gggaccaaag tggatatcaa a                                             321
```

<210> SEQ ID NO 8
<211> LENGTH: 75
<212> TYPE: PRT
<213> ORGANISM: Homo sapiens

<400> SEQUENCE: 8

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Arg Asn Asp
                 20                  25                  30
Leu Asp Trp Tyr Gln Gln Lys Pro Gly Lys Ala Pro Lys Arg Leu Ile
             35                  40                  45
Tyr Asp Ala Ser Ser Leu Gln Ser Leu Gln His Asp Ser Tyr Pro Phe
         50                  55                  60
Thr Phe Gly Pro Gly Thr Lys Val Asp Ile Lys
 65                  70                  75
```

<210> SEQ ID NO 9
<211> LENGTH: 357
<212> TYPE: DNA
<213> ORGANISM: Homo sapiens

<400> SEQUENCE: 9

```
gaggtgcagt tggtggagtc tgggggaggc ctggtcaagc ctggggggtc cctgagactc    60
tcctgtgcag cctctggatt caccttcagt gattataaca tgcactgggt ccgccaggct   120
ccagggaagg ggttagagtg ggtctcatcc attagttata gtagtactta catatactac   180
gcagactcag tgaggggccg attcaccatc tccagagaca acgccaagaa ctcactttat   240
ctgcaaatga acagcctgag agccgaggac acggctgtat tttactgtgc gagagaagac   300
tactactact acggtttgga cgtctggggc caagggacca cggtcaccgt ctcctca     357
```

<210> SEQ ID NO 10
<211> LENGTH: 119
<212> TYPE: PRT
<213> ORGANISM: Homo sapiens

<400> SEQUENCE: 10

```
Glu Val Gln Leu Val Glu Ser Gly Gly Gly Leu Val Lys Pro Gly Gly
  1               5                  10                  15
```

```
Ser Leu Arg Leu Ser Cys Ala Ala Ser Gly Phe Thr Phe Ser Asp Tyr
            20                  25                  30

Asn Met His Trp Val Arg Gln Ala Pro Gly Lys Gly Leu Glu Trp Val
        35                  40                  45

Ser Ser Ile Ser Tyr Ser Ser Thr Tyr Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Glu Asp Tyr Tyr Tyr Gly Leu Asp Val Trp Gly Gln Gly
            100                 105                 110

Thr Thr Val Thr Val Ser Ser
        115

<210> SEQ ID NO 11
<211> LENGTH: 321
<212> TYPE: DNA
<213> ORGANISM: Homo sapiens

<400> SEQUENCE: 11
gacatccaga tgacccagtc tccatcctcc ctgtctgcat ctgtaggaga cagagtcacc      60
atcacttgcc gggcaagtca ggacattaga aatgatttag ctggtatca gcagaaacca     120 gggaaagccc ctaagcgcct gatttatgat gcatccagtt tgcaaagtgg ggtcccatca    180
aggttcagcg gcagtggatc tgggacagaa ttcactctca caatcagcag cctgcagcct    240
gaagattttg caatttatta ctgtctacaa cataatagtt acccgtggac gttcggccaa    300
gggaccaagg tggaaatcaa a                                              321

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ile Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 13
<211> LENGTH: 363
<212> TYPE: DNA
<213> ORGANISM: Homo sapiens

<400> SEQUENCE: 13
gaggtgcagc tggtggagtc tgggggaggc ctggtcaagc ctggggggtc cctgagactc      60
```

```
tcctgtgcag cctctggatt caccttcagt agctatagca tgaactgggt ccgccaggct    120
ccaggaaagg ggctggagtg ggtctcatac attagtacca gtaatagtta catatactac    180
gcagactcag tgaagggccg attcaccatc tccagagaca tgccaagaa ctcactgtat    240 ctgcaaatga acagcctgag agccgaggac acggctgtgt attactgtgc gagagatcaa    300
gtgggagcta cccttgatgc ttttgatatc tggggccaag gacaatggt caccgtctct    360 tca                                                                 363

<210> SEQ ID NO 14
<211> LENGTH: 121
<212> TYPE: PRT
<213> ORGANISM: Homo sapiens

<400> SEQUENCE: 14

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Thr Ser Asn Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Val Gly Ala Thr Leu Asp Ala Phe Asp Ile Trp Gly
            100                 105                 110

Gln Gly Thr Met Val Thr Val Ser Ser
        115                 120

<210> SEQ ID NO 15
<211> LENGTH: 321
<212> TYPE: DNA
<213> ORGANISM: Homo sapiens

<400> SEQUENCE: 15
gacatccaga tgacccagtc tccatcctcc ctgtctgctt ctgtaggaga cagagtcacc     60
ttcacttgcc gggcaagtca ggacattaca gatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccattcac cttcggtcct    300
gggaccaaag tggatatcag a                                              321

<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
  1               5                  10                  15

Asp Arg Val Thr Phe Thr Cys Arg Ala Ser Gln Asp Ile Thr Asp Asp
             20                  25                  30
```

```
Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Arg
            100                 105
```

```
<210> SEQ ID NO 17
<211> LENGTH: 363
<212> TYPE: DNA
<213> ORGANISM: Homo sapiens

<400> SEQUENCE: 17
gaggtgcagc tggtggagtc tgggggaggc ctggtcaagc ctgggggtc cctgagactc      60 tcctgtgcag cctctggatt caccttcagt agctatagca tgaactgggt ccgccaggct    120
ccaggaaagg gctggagtg gtctcatac attagtacca gtaatagtta catatactac      180
gcagactcag tgaagggccg attcaccatc tccagagaca tgccaagaa ctcactgtat     240 ctgcaaatga acagcctgag agccgaggac acggctgtgt attactgtgc gagagatcaa    300
gtgggagcca cccttgatgc ttttgatatc tggggccaag ggacaatggt caccgtctct    360
tca                                                                  363

<210> SEQ ID NO 18
<211> LENGTH: 121
<212> TYPE: PRT
<213> ORGANISM: Homo sapiens

<400> SEQUENCE: 18
```

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Thr Ser Asn Ser Tyr Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Val Gly Ala Thr Leu Asp Ala Phe Asp Ile Trp Gly
            100                 105                 110

Gln Gly Thr Met Val Thr Val Ser Ser
            115                 120
```

```
<210> SEQ ID NO 19
<211> LENGTH: 321
<212> TYPE: DNA
<213> ORGANISM: Homo sapiens

<400> SEQUENCE: 19
gacatccaga tgacccagtc tccatcctcc ctgtctgctt ctgtaggaga cagagtcacc      60
```

```
ttcacttgcc gggcaagtca ggacattaca gatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccattcac cttcggtcct    300
gggaccaaag tggatatcag a                                              321
```

```
<210> SEQ ID NO 20
<211> LENGTH: 107
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
  1               5                  10                  15

Asp Arg Val Thr Phe Thr Cys Arg Ala Ser Gln Asp Ile Thr Asp Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Phe
                 85                  90                  95

Thr Phe Gly Pro Gly Thr Lys Val Asp Ile Arg
            100                 105
```

```
<210> SEQ ID NO 21
<211> LENGTH: 363
<212> TYPE: DNA
<213> ORGANISM: Homo sapiens

<400> SEQUENCE: 21
gaggtgcagc tggtggagtc tgggggaggc ctggtcaagc ctgggggagtc cctgagactc    60 tcctgtgcag cctctggatt caccttcagt agctatagca tgaactgggt ccgccaggct    120
ccagggaagg gctggagtg gtctctcatac attagtacta gttataatta catatactac    180
gcagactcag tgaagggccg attcaccatc tccagagaca acgccaagaa ctcactgtat    240
ctgcaaatga acagcctgag agccgaggac acggctgtgt attactgtgc gagagatcaa    300
gtgggagcta cccttgatgc ttttgatatc tggggccaag gacaatggt caccgtctct    360 tca                                                                  363
```

```
<210> SEQ ID NO 22
<211> LENGTH: 121
<212> TYPE: PRT
<213> ORGANISM: Homo sapiens

<400> SEQUENCE: 22

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Thr Ser Tyr Asn Tyr Ile Tyr Tyr Ala Asp Ser Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Val Gly Ala Thr Leu Asp Ala Phe Asp Ile Trp Gly
            100                 105                 110

Gln Gly Thr Met Val Thr Val Ser Ser
        115                 120

<210> SEQ ID NO 23
<211> LENGTH: 321
<212> TYPE: DNA
<213> ORGANISM: Homo sapiens

<400> SEQUENCE: 23
gacatccaga tgacccagtc tccatcctcc ctgtctgcat ctgtaggaga cagagtcacc      60
atcacttgcc gggcaagtca gggcattgga gatgatttag ctggtatca gcagaagcca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccattcac tttcggccct    300
gggaccagag tggatatcaa a                                              321

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Gly Asp Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Phe
                 85                  90                  95

Thr Phe Gly Pro Gly Thr Arg Val Asp Ile Lys
            100                 105

<210> SEQ ID NO 25
<211> LENGTH: 363
<212> TYPE: DNA
<213> ORGANISM: Homo sapiens

<400> SEQUENCE: 25
gaggtgcagc tggtggagtc tgggggaggc ctggtcaagc ctggggggtc cctgagactc      60
tcctgtgcag cctctggatt cacccttcagt agctatagca tgaactgggt ccgccaggct    120
ccaggaaagg ggctggagtg ggtctcatac attagtacca gtaatagtta catatactac    180
gcagactcag tgaagggccg attcaccatc tccagagaca atgccaagaa ctcactgtat    240
```

```
ctgcaaatga acagcctgag agccgaggac acggctgtgt attactgtgc gagagatcaa    300
gtgggagcta cccttgatgc ttttgatatc tggggccaag gacaatggt caccgtctct    360 tca                                                                  363
```

<210> SEQ ID NO 26
<211> LENGTH: 121
<212> TYPE: PRT
<213> ORGANISM: Homo sapiens

<400> SEQUENCE: 26

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Thr Ser Asn Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Gln Val Gly Ala Thr Leu Asp Ala Phe Asp Ile Trp Gly
            100                 105                 110

Gln Gly Thr Met Val Thr Val Ser Ser
        115                 120
```

<210> SEQ ID NO 27
<211> LENGTH: 321
<212> TYPE: DNA
<213> ORGANISM: Homo sapiens

<400> SEQUENCE: 27

```
gacatccaga tgacccagtc tccatcctcc ctgtctgctt ctgtaggaga cagagtcacc    60
ttcacttgcc gggcaagtca ggacattaca gatgatttag gctggtatca gcagaaacca    120
gggaaagccc ctaagcgcct gatctatgct gcatccagtt tgcaaagtgg ggtcccacca    180
aggttcagcg gcagtggatc tgggacagaa ttcactctca caatcagcag cctgcagcct    240
gaagattttg caacttatta ctgtctacag cataatagtt acccattcac cttcggtcct    300
gggaccaaag tggatatcag a                                              321
```

<210> SEQ ID NO 28
<211> LENGTH: 107
<212> TYPE: PRT
<213> ORGANISM: Homo sapiens

<400> SEQUENCE: 28

```
Asp Ile Gln Met Thr Gln Ser Pro Ser Ser Leu Ser Ala Ser Val Gly
  1               5                  10                  15

Asp Arg Val Thr Phe Thr Cys Arg Ala Ser Gln Asp Ile Thr Asp Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Pro Arg Phe Ser Gly
 50                  55                  60

Ser Gly Ser Gly Thr Glu Phe Thr Leu Thr Ile Ser Ser Leu Gln Pro
```

```
                65                  70                  75                  80
Glu Asp Phe Ala Thr Tyr Tyr Cys Leu Gln His Asn Ser Tyr Pro Phe
                    85                  90                  95

Thr Phe Gly Pro Gly Thr Lys Val Asp Ile Arg
                100                 105
```

<210> SEQ ID NO 29
<211> LENGTH: 363
<212> TYPE: DNA
<213> ORGANISM: Homo sapiens

<400> SEQUENCE: 29

```
gaggtgcagc tggtggagtc tgggggaggc ctggtcaagc ctgggggggtc cctgagactc      60 tcctgtgcag cctctggatt caccttcagt agctatagca tgaactgggt ccgccaggct     120
ccagggaagg gctggagtg gtctcatac attagtagta gttataatta catatactac       180
ggagactcag tgaagggccg attcaccatc tccagagaca cgccaagaa ctcactgtat      240 ttgcaaatga acagcctgag agccgaggac acggctgtgt attactgtgc gagagatcaa    300
gtgggagcta cccttgatgc ttttgatatc tggggccaag ggacaatggt caccgtctct    360
tca                                                                   363
```

<210> SEQ ID NO 30
<211> LENGTH: 121
<212> TYPE: PRT
<213> ORGANISM: Homo sapiens

<400> SEQUENCE: 30

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Tyr Asn Tyr Ile Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Val Gly Ala Thr Leu Asp Ala Phe Asp Ile Trp Gly
            100                 105                 110

Gln Gly Thr Met Val Thr Val Ser Ser
        115                 120
```

<210> SEQ ID NO 31
<211> LENGTH: 321
<212> TYPE: DNA
<213> ORGANISM: Homo sapiens

<400> SEQUENCE: 31

```
gacatccaga tgacccagtc tccatcctcc ctgtctgcat ctgtaggaga cagagtcacc      60
atcacttgcc gggcaagtca gggcattgga gatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct   240
gaagattttg caacttatta ctgtctacag cataatagtt acccattcac tttcggccct    300
```
gggaccaaag tggatatcaa a                                              321

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105

<210> SEQ ID NO 33
<211> LENGTH: 369
<212> TYPE: DNA
<213> ORGANISM: Homo sapiens

<400> SEQUENCE: 33
gaggtgcagc tgttggagtc tgggggaggc ttggtacagc ctggggggtc cctgagactc      60
tcctgtgcag cctctggatt cacctttagc agctatgcca tgagctgggt ccgccaggct    120
ccagggaagg ggctggagtg ggtctcagct tttagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgt gcaagatggg    300 ctggggcccct acttctacaa ctacggtatg gacgtctggg gccaagggac cacggtcacc    360
gtctcctca                                                             369

<210> SEQ ID NO 34
<211> LENGTH: 123
<212> TYPE: PRT
<213> ORGANISM: Homo sapiens

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Phe Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Val Gln Asp Gly Leu Gly Pro Tyr Phe Tyr Asn Tyr Gly Met Asp Val
            100                 105                 110

Trp Gly Gln Gly Thr Thr Val Thr Val Ser Ser
        115                 120

<210> SEQ ID NO 35
<211> LENGTH: 321
<212> TYPE: DNA
<213> ORGANISM: Homo sapiens

<400> SEQUENCE: 35
tcctatgaac tgactcagcc accctcagtg tccgtgtccc caggacagac agccagcatc    60
acctgctctg gagataaaat tggggataaa tatacttgct ggtttcaaca gaagccaggc   120
cagtcccctg tgctggtcat ctatcacgat agcaagcggc cctcagggat ccctgagcga   180
ttctctggct ccaactctgg gacacagcc actctgacca tcagcgggac ccaggctatg    240
gatgaggctg actattactg tcaggcgtgg gacagcagca cttatgtctt cggaactggg   300
accaaagtca ccgtcctagg t                                             321

<210> SEQ ID NO 36
<211> LENGTH: 107
<212> TYPE: PRT
<213> ORGANISM: Homo sapiens

<400> SEQUENCE: 36

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Thr
            20                  25                  30

Cys Trp Phe Gln Gln Lys Pro Gly Gln Ser Pro Val Leu Val Ile Tyr
        35                  40                  45

His Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Tyr Val
                85                  90                  95

Phe Gly Thr Gly Thr Lys Val Thr Val Leu Gly
            100                 105

<210> SEQ ID NO 37
<211> LENGTH: 369
<212> TYPE: DNA
<213> ORGANISM: Homo sapiens

<400> SEQUENCE: 37
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct tttagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgt gcaagatggg   300
ctggggccct acttctacaa ctacggtatg gacgtctggg gccaagggac cacggtcacc   360
gtctcctca                                                           369
```

<210> SEQ ID NO 38
<211> LENGTH: 123
<212> TYPE: PRT
<213> ORGANISM: Homo sapiens

<400> SEQUENCE: 38

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Phe Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Gln Asp Gly Leu Gly Pro Tyr Phe Tyr Asn Tyr Gly Met Asp Val
            100                 105                 110

Trp Gly Gln Gly Thr Thr Val Thr Val Ser Ser
        115                 120
```

<210> SEQ ID NO 39
<211> LENGTH: 321
<212> TYPE: DNA
<213> ORGANISM: Homo sapiens

<400> SEQUENCE: 39

```
tcctatgaac tgactcagcc accctcagtg tccgtgtccc caggacagac agccagcatc     60
acctgctctg gagataaaatt ggggataaa tatgcttgct ggtttcaaca gaagccaggc    120
cagtcccctg tgctggtcat ctatcacgat agcaagcggc cctcagggat ccctgagcga    180
ttctctggct ccaactctgg gacacagca ctctgacca tcagcgggac ccaggctatg      240
gatgaggctg actattactg tcaggcgtgg gacagcagca cttatgtctt cggaactggg    300
accaaagtca ccgtcctagg t                                              321
```

<210> SEQ ID NO 40
<211> LENGTH: 107
<212> TYPE: PRT
<213> ORGANISM: Homo sapiens

<400> SEQUENCE: 40

```
Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
            20                  25                  30

Cys Trp Phe Gln Gln Lys Pro Gly Gln Ser Pro Val Leu Val Ile Tyr
        35                  40                  45

His Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Tyr Val
                85                  90                  95

Phe Gly Thr Gly Thr Lys Val Thr Val Leu Gly
```

<210> SEQ ID NO 41
<211> LENGTH: 354
<212> TYPE: DNA
<213> ORGANISM: Homo sapiens

<400> SEQUENCE: 41

```
caggtgcagc tgcaggagtc gggcccagga ctggtgaagc cttcggagac cctgtccctc      60
acctgcagtg tctctggcgg ctccatcagt agttactatt ggagctggat ccggcagccc     120
gccgggaagg gactggagtg gattggcgt atctatatga ctgggagaac caactacaat     180
tcttccctca agagtcgagt caccatgtca atagacacgt ccaagaacca gctctccctg     240
aagttgagtt ttatgaccgc cgcggacacg gccgtgtatt actgtgcgag agaaagtgga     300
tccagctata gttacgacta ctggggccag ggaaccctgg tcaccgtctc ctca           354
```

<210> SEQ ID NO 42
<211> LENGTH: 118
<212> TYPE: PRT
<213> ORGANISM: Homo sapiens

<400> SEQUENCE: 42

```
Gln Val Gln Leu Gln Glu Ser Gly Pro Gly Leu Val Lys Pro Ser Glu
 1               5                  10                  15

Thr Leu Ser Leu Thr Cys Ser Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Met Thr Gly Arg Thr Asn Tyr Asn Ser Ser Leu Lys
    50                  55                  60

Ser Arg Val Thr Met Ser Ile Asp Thr Ser Lys Asn Gln Leu Ser Leu
65                  70                  75                  80

Lys Leu Ser Phe Met Thr Ala Ala Asp Thr Ala Val Tyr Tyr Cys Ala
                85                  90                  95

Arg Glu Ser Gly Ser Ser Tyr Ser Tyr Asp Tyr Trp Gly Gln Gly Thr
            100                 105                 110

Leu Val Thr Val Ser Ser
        115
```

<210> SEQ ID NO 43
<211> LENGTH: 328
<212> TYPE: DNA
<213> ORGANISM: Homo sapiens

<400> SEQUENCE: 43

```
tcctatgtgc tgactcagcc accctcggtg tcagtggccc caggacagac ggccaggatt      60
acctgtgggg gaaacaacat tggaagtaaa ggtgttcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gttagtagta gtgatcatca tgtggtattc     300
ggcggaggga ccaagctgac cgtcgtag                                        328
```

<210> SEQ ID NO 44
<211> LENGTH: 109
<212> TYPE: PRT
<213> ORGANISM: Homo sapiens

<400> SEQUENCE: 44

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Val Ser Ser Asp His
                85                  90                  95

His Val Val Phe Gly Gly Gly Thr Lys Leu Thr Val Val
            100                 105

<210> SEQ ID NO 45
<211> LENGTH: 378
<212> TYPE: DNA
<213> ORGANISM: Homo sapiens

<400> SEQUENCE: 45
gaggtgcagt tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attagaagtg agattgatgg tgggacgaca    180
aattacgctg cacccgtgaa aggcagattc accatctcaa gagatgattc aaaaaacacg    240
ctgtatctgc aaatgaacag cctgagaacc gaggacacag ccgtgtatta ctgtgccaca    300
gatcaggtgg gagcttacta cggggactac tacggtatgg acgtctgggg ccaagggacc    360
acggtcaccg tctcctca                                                  378

<210> SEQ ID NO 46
<211> LENGTH: 126
<212> TYPE: PRT
<213> ORGANISM: Homo sapiens

<400> SEQUENCE: 46

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Arg Ser Glu Ile Asp Gly Gly Thr Thr Asn Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Ala Thr Asp Gln Val Gly Ala Tyr Tyr Gly Asp Tyr Tyr Gly
            100                 105                 110

Met Asp Val Trp Gly Gln Gly Thr Thr Val Thr Val Ser Ser
        115                 120                 125

<210> SEQ ID NO 47
<211> LENGTH: 327
<212> TYPE: DNA
<213> ORGANISM: Homo sapiens

<400> SEQUENCE: 47

```
tcctatgagc tgacacagcc accctcggtg tcagtgtccc caggacaaac ggccaggatc      60
acctgctctg gagatgcgtt gccagaaaaa tatgcttatt ggtaccagca gaagtcaggc     120
caggcccctg tgctggtcat ctatgaggac agcaaacgac cctccgggat ccctgagaga     180
ttctctggct ccagctcagg gacaatggcc accttgacta tcagtggggc ccaggtggag     240
gatgaagctg actactactg tcattcaaca gacagcagtg gtaatcatgg ggtgttcggc     300
ggagggacca agctgaccgt cctaggt                                         327
```

<210> SEQ ID NO 48
<211> LENGTH: 109
<212> TYPE: PRT
<213> ORGANISM: Homo sapiens

<400> SEQUENCE: 48

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Glu Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys His Ser Thr Asp Ser Ser Gly Asn His
                85                  90                  95

Gly Val Phe Gly Gly Gly Thr Lys Leu Thr Val Leu Gly
            100                 105

<210> SEQ ID NO 49
<211> LENGTH: 379
<212> TYPE: DNA
<213> ORGANISM: Homo sapiens

<400> SEQUENCE: 49

```
gaggtgcagt tggtgagagt ctgggggagg cttggtaaag cctgggggt ccttagact       60
ctcctgtgca gcctctggat tcactttcag taacgcctgg atgagctggg tccgccaggc    120
tccaggaag gggctggagt gggttggccg tattagaagt gaaattgatg gtgggacaac    180
aaactacgct gcacccgtga aggcagatt caccatctca agagatgatt caaaaaacac    240
gctgtatctg caaatgaaca gcctgaaaac cgaggacaca gccgtgtatt actgtgccac    300
agatcaggtg ggagcttact acggggacta ctacggtatg gacgtctggg gccaagggac    360
cacggtcacc gtctcctca                                                 379
```

<210> SEQ ID NO 50
<211> LENGTH: 126
<212> TYPE: PRT
<213> ORGANISM: Homo sapiens

<400> SEQUENCE: 50

Glu Val Gln Leu Val Glu Ser Gly Gly Gly Leu Val Lys Pro Gly Gly

```
                1               5                   10                  15
Ser Leu Arg Leu Ser Cys Ala Ala Ser Gly Phe Thr Phe Ser Asn Ala
                    20                  25                  30

Trp Met Ser Trp Val Arg Gln Ala Pro Gly Lys Gly Leu Glu Trp Val
            35                  40                  45

Gly Arg Ile Arg Ser Glu Ile Asp Gly Gly Thr Thr Asn Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Thr Asp Gln Val Gly Ala Tyr Tyr Gly Asp Tyr Tyr Gly
                    100                 105                 110

Met Asp Val Trp Gly Gln Gly Thr Thr Val Thr Val Ser Ser
                115                 120                 125

<210> SEQ ID NO 51
<211> LENGTH: 327
<212> TYPE: DNA
<213> ORGANISM: Homo sapiens

<400> SEQUENCE: 51
tcctatgagc tgacacagcc accctcggtg tcagtgtccc caggacaaac ggccaggatc      60
acctgctctg gagatgcatt gccagaaaaa tatgcttatt ggtaccagca gaagtcaggc     120
caggcccctg tgctggtcat ctatgaggac agcaaacgac cctccgggat ccctgagaga     180
ttctctggct ccagctcagg gacaatggcc accttgacta tcagtggggc cagghtggag     240
gatgaagctg actactactg tcattcaaca gacagcagtg gtaatcatgg ggtgttcggc     300
ggagggacca agctgaccgt cctaggt                                         327

<210> SEQ ID NO 52
<211> LENGTH: 109
<212> TYPE: PRT
<213> ORGANISM: Homo sapiens

<400> SEQUENCE: 52

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Glu Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
5                   70                  75                  80

Asp Glu Ala Asp Tyr Tyr Cys His Ser Thr Asp Ser Ser Gly Asn His
                85                  90                  95

Gly Val Phe Gly Gly Gly Thr Lys Leu Thr Val Leu Gly
                100                 105

<210> SEQ ID NO 53
<211> LENGTH: 378
<212> TYPE: DNA
<213> ORGANISM: Homo sapiens

<400> SEQUENCE: 53
```

-continued

```
gaggtgcagc tggtggagtc tgggggaggc ttggtaaagc ctggggggtc tcttagactc      60
tcctgtgcag cctctggatt cactttcagt aacgcctgga tgagctgggt ccgccaggct     120
ccagggaagg gctggagtg gttggccgt attagaagca aaattgatgg tgggacaata      180
aactacgctg cacccgtgaa aggcagattc accatctcaa gagatgattc aaaaaacacg     240
ctgtatctgc aaatgaacag cctgaaaacc gaggacacag ccgtgtatta ctgtgccaca     300
gatcaggtgg gagcttacta cggggactac tacggtatgg acgtctgggg ccaagggacc     360
acggtcaccg tctcctca                                                   378
```

<210> SEQ ID NO 54
<211> LENGTH: 126
<212> TYPE: PRT
<213> ORGANISM: Homo sapiens

<400> SEQUENCE: 54

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Arg Ser Lys Ile Asp Gly Gly Thr Ile Asn Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Thr Asp Gln Val Gly Ala Tyr Tyr Gly Asp Tyr Tyr Gly
            100                 105                 110

Met Asp Val Trp Gly Gln Gly Thr Thr Val Thr Val Ser Ser
        115                 120                 125
```

<210> SEQ ID NO 55
<211> LENGTH: 327
<212> TYPE: DNA
<213> ORGANISM: Homo sapiens

<400> SEQUENCE: 55

```
tcctatgagc tgacacagcc accctcggtg tcagtgtccc caggacaaac ggccaggatc      60
acctgctctg gagatgcatt gccagaaaaa tatgcttatt ggtaccagca gaagtcaggc     120
caggcccctg tgctggtcat ctatgaggac accaaacgac cctccgggat ccctgagaga     180
ttctctggct ccagctcagg gacaatggcc accttgacta tcagtggggc caggtggag      240 gatgaagctg actactattg ttattcaaca gacagcagtg gtaatcatgg ggtgttcggc     300
ggagggacca agctgaccgt cctaggt                                         327
```

<210> SEQ ID NO 56
<211> LENGTH: 109
<212> TYPE: PRT
<213> ORGANISM: Homo sapiens

<400> SEQUENCE: 56

```
Ser Tyr Glu Leu Thr Gln Pro Pro Ser Val Ser Val Ser Pro Gly Gln
  1               5                  10                  15

Thr Ala Arg Ile Thr Cys Ser Gly Asp Ala Leu Pro Glu Lys Tyr Ala
```

-continued

```
                    20                  25                  30
Tyr Trp Tyr Gln Gln Lys Ser Gly Gln Ala Pro Val Leu Val Ile Tyr
            35                  40                  45

Glu Asp Thr Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Gly Asn His
                 85                  90                  95

Gly Val Phe Gly Gly Gly Thr Lys Leu Thr Val Leu Gly
            100                 105
```

<210> SEQ ID NO 57
<211> LENGTH: 366
<212> TYPE: DNA
<213> ORGANISM: Homo sapiens

<400> SEQUENCE: 57

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagccgat     300
ttttggagtg gtacattatg ggggtttgac tactggggcc agggaaccct ggtcaccgtc     360
tcctca                                                                366
```

<210> SEQ ID NO 58
<211> LENGTH: 122
<212> TYPE: PRT
<213> ORGANISM: Homo sapiens

<400> SEQUENCE: 58

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Asp Phe Trp Ser Gly Thr Leu Trp Gly Phe Asp Tyr Trp
            100                 105                 110

Gly Gln Gly Thr Leu Val Thr Val Ser Ser
        115                 120
```

<210> SEQ ID NO 59
<211> LENGTH: 327
<212> TYPE: DNA
<213> ORGANISM: Homo sapiens

<400> SEQUENCE: 59

-continued

```
tcctatgtgc tgactcagcc accctcggtg tcagtggccc caggacagac ggccaggatt    60
acctgtgggg gaaacaacat tggaaataaa attgtgcact ggtaccagca aaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca agctgaccgt cctaggt                                       327
```

<210> SEQ ID NO 60
<211> LENGTH: 109
<212> TYPE: PRT
<213> ORGANISM: Homo sapiens

<400> SEQUENCE: 60

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Asn Lys Ile Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 61
<211> LENGTH: 112
<212> TYPE: PRT
<213> ORGANISM: Homo sapiens

<400> SEQUENCE: 61

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Gln Phe Asn
            100                 105                 110

<210> SEQ ID NO 62
<211> LENGTH: 114
<212> TYPE: PRT
<213> ORGANISM: Homo sapiens

<400> SEQUENCE: 62

Ser Pro Gly Pro Val Pro Pro Ser Thr Ala Leu Arg Glu Leu Ile Glu
1               5                   10                  15

-continued

```
                1               5                  10                 15
Glu Leu Val Asn Ile Thr Gln Asn Gln Lys Ala Pro Leu Cys Asn Gly
                20                 25                 30

Ser Met Val Trp Ser Ile Asn Leu Thr Ala Gly Met Tyr Cys Ala Ala
                35                 40                 45

Leu Glu Ser Leu Ile Asn Val Ser Gly Cys Ser Ala Ile Glu Lys Thr
                50                 55                 60

Gln Arg Met Leu Ser Gly Phe Cys Pro His Lys Val Ser Ala Gly Gln
 65                 70                 75                 80

Phe Ser Ser Leu His Val Arg Asp Thr Lys Ile Glu Val Ala Gln Phe
                85                 90                 95

Val Lys Asp Leu Leu Leu His Leu Lys Lys Leu Phe Arg Glu Gly Arg
                100                105                110

Phe Asn
```

<210> SEQ ID NO 63
<211> LENGTH: 115
<212> TYPE: PRT
<213> ORGANISM: Homo sapiens

<400> SEQUENCE: 63

```
Met Ser Pro Gly Pro Val Pro Ser Thr Ala Leu Arg Glu Leu Ile
 1               5                  10                 15

Glu Glu Leu Val Asn Ile Thr Gln Asn Gln Lys Ala Pro Leu Cys Asn
                20                 25                 30

Gly Ser Met Val Trp Ser Ile Asn Leu Thr Ala Gly Met Tyr Cys Ala
                35                 40                 45

Ala Leu Glu Ser Leu Ile Asn Val Ser Gly Cys Ser Ala Ile Glu Lys
                50                 55                 60

Thr Gln Arg Met Leu Ser Gly Phe Cys Pro His Lys Val Ser Ala Gly
 65                 70                 75                 80

Gln Phe Ser Ser Leu His Val Arg Asp Thr Lys Ile Glu Val Ala Gln
                85                 90                 95

Phe Val Lys Asp Leu Leu Leu His Leu Lys Lys Leu Phe Arg Glu Gly
                100                105                110

Gln Phe Asn
        115
```

<210> SEQ ID NO 64
<211> LENGTH: 364
<212> TYPE: PRT
<213> ORGANISM: Homo sapiens

<400> SEQUENCE: 64

```
Met Ala Leu Leu Leu Thr Thr Val Ile Ala Leu Thr Cys Leu Gly Gly
 1               5                  10                 15

Phe Ala Ser Pro Gly Pro Val Pro Pro Ser Thr Ala Leu Arg Glu Leu
                20                 25                 30

Ile Glu Glu Leu Val Asn Ile Thr Gln Asn Gln Lys Ala Pro Leu Cys
                35                 40                 45

Asn Gly Ser Met Val Trp Ser Ile Asn Leu Thr Ala Gly Met Tyr Cys
                50                 55                 60

Ala Ala Leu Glu Ser Leu Ile Asn Val Ser Gly Cys Ser Ala Ile Glu
 65                 70                 75                 80

Lys Thr Gln Arg Met Leu Ser Gly Phe Cys Pro His Lys Val Ser Ala
                85                 90                 95
```

Gly Gln Phe Ser Ser Leu His Val Arg Asp Thr Lys Ile Glu Val Ala
                100                 105                 110

Gln Phe Val Lys Asp Leu Leu Leu His Leu Lys Lys Leu Phe Arg Glu
            115                 120                 125

Gly Arg Phe Asn Glu Pro Lys Ser Cys Asp Lys Thr His Thr Cys Pro
        130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
    355                 360

<210> SEQ ID NO 65
<211> LENGTH: 367
<212> TYPE: PRT
<213> ORGANISM: Homo sapiens

<400> SEQUENCE: 65

Met Ala Leu Leu Leu Thr Thr Val Ile Ala Leu Thr Cys Leu Gly Gly
  1               5                  10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala

-continued

```
            100                 105                 110
Gln Phe Val Lys Asp Leu Leu His Leu Lys Lys Leu Phe Arg Glu
            115                 120                 125

Gly Arg Phe Asn Arg Tyr Leu Asp Lys Thr Val Ala Pro Ser Thr Cys
130                 135                 140

Ser Lys Pro Thr Cys Pro Pro Glu Leu Leu Gly Pro Ser Val
145                 150                 155                 160

Phe Ile Phe Pro Pro Lys Pro Lys Asp Thr Leu Met Ile Ser Arg Thr
                    165                 170                 175

Pro Glu Val Thr Cys Val Val Asp Val Ser Gln Asp Asp Pro Glu
                180                 185                 190

Val Gln Phe Thr Trp Tyr Ile Asn Asn Glu Gln Val Arg Thr Ala Arg
            195                 200                 205

Pro Pro Leu Arg Glu Gln Gln Phe Asn Ser Thr Ile Arg Val Val Ser
        210                 215                 220

Thr Leu Pro Ile Ala His Gln Asp Trp Leu Arg Gly Lys Glu Phe Lys
225                 230                 235                 240

Cys Lys Val His Asn Lys Ala Leu Pro Ala Pro Ile Glu Lys Thr Ile
                    245                 250                 255

Ser Lys Ala Arg Gly Gln Pro Leu Glu Pro Lys Val Tyr Thr Met Gly
                260                 265                 270

Pro Pro Arg Glu Glu Leu Ser Ser Arg Ser Val Ser Leu Thr Cys Met
            275                 280                 285

Ile Asn Gly Phe Tyr Pro Ser Asp Ile Ser Val Glu Trp Glu Lys Asn
        290                 295                 300

Gly Lys Ala Glu Asp Asn Tyr Lys Thr Thr Pro Ala Val Leu Asp Ser
305                 310                 315                 320

Asp Gly Ser Tyr Phe Leu Tyr Asn Lys Leu Ser Val Pro Thr Ser Glu
                    325                 330                 335

Trp Gln Arg Gly Asp Val Phe Thr Cys Ser Val Met His Glu Ala Leu
                340                 345                 350

His Asn His Tyr Thr Gln Lys Ser Ile Ser Arg Ser Pro Gly Lys
            355                 360                 365

<210> SEQ ID NO 66
<211> LENGTH: 150
<212> TYPE: PRT
<213> ORGANISM: Homo sapiens

<400> SEQUENCE: 66

Met His Pro Leu Leu Asn Pro Leu Leu Leu Ala Leu Gly Leu Met Ala
  1               5                  10                  15

Leu Leu Leu Thr Thr Val Ile Ala Leu Thr Cys Leu Gly Gly Phe Ala
                20                  25                  30

Ser Pro Gly Pro Val Pro Arg Ser Val Ser Leu Pro Leu Thr Leu Lys
            35                  40                  45

Glu Leu Ile Glu Glu Leu Val Asn Ile Thr Gln Asn Gln Lys Ala Pro
        50                  55                  60

Leu Cys Asn Gly Ser Met Val Trp Ser Ile Asn Leu Thr Ala Gly Met
65                  70                  75                  80

Tyr Cys Ala Ala Leu Glu Ser Leu Ile Asn Val Ser Gly Cys Ser Ala
                    85                  90                  95

Ile Glu Lys Thr Gln Arg Met Leu Ser Gly Phe Cys Pro His Lys Val
                100                 105                 110
```

```
Ser Ala Gly Gln Phe Ser Ser Leu His Val Arg Asp Thr Lys Ile Glu
        115                 120                 125
Val Ala Gln Phe Val Lys Asp Leu Leu Leu His Leu Lys Lys Leu Phe
130                 135                 140
Arg Glu Gly Gln Phe Asn
145                 150

<210> SEQ ID NO 67
<211> LENGTH: 146
<212> TYPE: PRT
<213> ORGANISM: Homo sapiens

<400> SEQUENCE: 67

Met His Pro Leu Leu Asn Pro Leu Leu Leu Ala Leu Gly Leu Met Ala
1               5                   10                  15
Leu Leu Leu Thr Thr Val Ile Ala Leu Thr Cys Leu Gly Gly Phe Ala
                20                  25                  30
Ser Pro Gly Pro Val Pro Pro Ser Thr Ala Leu Arg Glu Leu Ile Glu
                35                  40                  45
Glu Leu Val Asn Ile Thr Gln Asn Gln Lys Ala Pro Leu Cys Asn Gly
        50                  55                  60
Ser Met Val Trp Ser Ile Asn Leu Thr Ala Gly Gly Phe Cys Val Ala
65                  70                  75                  80
Leu Asp Ser Leu Thr Asn Val Ser Gly Cys Ser Ala Ile Glu Lys Thr
                85                  90                  95
Gln Arg Met Leu Ser Gly Phe Cys Pro His Lys Val Ser Ala Gly Gln
                100                 105                 110
Phe Ser Ser Leu His Val Arg Asp Thr Lys Ile Glu Val Ala Gln Phe
            115                 120                 125
Val Lys Asp Leu Leu Leu His Leu Lys Lys Leu Phe Arg Glu Gly Gln
        130                 135                 140
Phe Asn
145

<210> SEQ ID NO 68
<211> LENGTH: 146
<212> TYPE: PRT
<213> ORGANISM: Homo sapiens

<400> SEQUENCE: 68

Met His Pro Leu Leu Asn Pro Leu Leu Leu Ala Leu Gly Leu Met Ala
1               5                   10                  15
Leu Leu Leu Thr Thr Val Ile Ala Leu Thr Cys Leu Gly Gly Phe Ala
                20                  25                  30
Ser Pro Gly Pro Val Pro Pro Ser Thr Ala Leu Arg Glu Leu Ile Glu
                35                  40                  45
Glu Leu Val Asn Ile Thr Gln Asn Gln Lys Ala Pro Leu Cys Asn Gly
        50                  55                  60
Ser Met Val Trp Ser Ile Asn Leu Thr Ala Gly Met Tyr Cys Ala Ala
65                  70                  75                  80
Leu Glu Ser Leu Ile Asn Val Ser Gly Cys Ser Ala Ile Tyr Arg Thr
                85                  90                  95
Gln Arg Ile Leu His Gly Leu Cys Pro His Lys Val Ser Ala Gly Gln
                100                 105                 110
Phe Ser Ser Leu His Val Arg Asp Thr Lys Ile Glu Val Ala Gln Phe
            115                 120                 125
```

Val Lys Asp Leu Leu His Leu Lys Leu Phe Arg Glu Gly Gln
130                 135                 140

Phe Asn
145

<210> SEQ ID NO 69
<211> LENGTH: 147
<212> TYPE: PRT
<213> ORGANISM: Homo sapiens

<400> SEQUENCE: 69

Met His Pro Leu Leu Asn Pro Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala His Phe
        115                 120                 125

Ile Thr Lys Leu Leu Ser Tyr Thr Lys Gln Leu Phe Arg His Gly Gln
130                 135                 140

Gln Phe Asn
145

<210> SEQ ID NO 70
<211> LENGTH: 12
<212> TYPE: PRT
<213> ORGANISM: Homo sapiens

<400> SEQUENCE: 70

Tyr Lys Ile Gly Glu Pro His Lys Asp Thr Tyr Met
1               5                   10

<210> SEQ ID NO 71
<211> LENGTH: 51
<212> TYPE: PRT
<213> ORGANISM: Homo sapiens

<400> SEQUENCE: 71

Thr Gln Arg Met Leu Ser Gly Phe Cys Pro His Lys Val Ser Ala Gly
1               5                   10                  15

Gln Phe Ser Ser Leu His Val Arg Asp Thr Lys Ile Glu Val Ala Gln
                20                  25                  30

Phe Val Lys Asp Leu Leu Leu His Leu Lys Lys Leu Phe Arg Glu Gly
            35                  40                  45

Arg Phe Asn
    50

<210> SEQ ID NO 72
<211> LENGTH: 113
<212> TYPE: PRT

<213> ORGANISM: Homo sapiens

<400> SEQUENCE: 72

Met Gly Pro Val Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Arg Phe
                100                 105                 110

Asn

<210> SEQ ID NO 73
<211> LENGTH: 88
<212> TYPE: PRT
<213> ORGANISM: Homo sapiens

<400> SEQUENCE: 73

Gly Pro Val Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys
                85

<210> SEQ ID NO 74
<211> LENGTH: 73
<212> TYPE: PRT
<213> ORGANISM: Homo sapiens

<400> SEQUENCE: 74

Gly Pro Val Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
50                  55                  60

Met Leu Ser Gly Phe Cys Pro His Lys
65                  70

<210> SEQ ID NO 75
<211> LENGTH: 72

```
<212> TYPE: PRT
<213> ORGANISM: Homo sapiens

<400> SEQUENCE: 75

Ala Pro Leu Cys Asn Gly Ser Met Val Trp Ser Ile Asn Leu Thr Ala
1               5                   10                  15

Gly Met Tyr Cys Ala Ala Leu Glu Ser Leu Ile Asn Val Ser Gly Cys
            20                  25                  30

Ser Ala Ile Glu Lys Thr Gln Arg Met Leu Ser Gly Phe Cys Pro His
        35                  40                  45

Lys Val Ser Ala Gly Gln Phe Ser Ser Leu His Val Arg Asp Thr Lys
50                  55                  60

Ile Glu Val Ala Gln Phe Val Lys
65                  70

<210> SEQ ID NO 76
<211> LENGTH: 64
<212> TYPE: PRT
<213> ORGANISM: Homo sapiens

<400> SEQUENCE: 76

Ala Pro Leu Cys Asn Gly Ser Met Val Trp Ser Ile Asn Leu Thr Ala
1               5                   10                  15

Gly Met Tyr Cys Ala Ala Leu Glu Ser Leu Ile Asn Val Ser Gly Cys
            20                  25                  30

Ser Ala Ile Glu Lys Thr Gln Arg Met Leu Ser Gly Phe Cys Pro His
        35                  40                  45

Lys Val Ser Ala Gly Gln Phe Ser Ser Leu His Val Arg Asp Thr Lys
50                  55                  60

<210> SEQ ID NO 77
<211> LENGTH: 150
<212> TYPE: PRT
<213> ORGANISM: Homo sapiens

<400> SEQUENCE: 77

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Arg Ser Val Ser Leu Pro Leu Thr Leu Lys
        35                  40                  45

Glu Leu Ile Glu Glu Leu Val Asn Ile Thr Gln Asn Gln Lys Ala Pro
50                  55                  60

Leu Cys Asn Gly Ser Met Val Trp Ser Ile Asn Leu Thr Ala Gly Met
65                  70                  75                  80

Tyr Cys Ala Ala Leu Glu Ser Leu Ile Asn Val Ser Gly Cys Ser Ala
            85                  90                  95

Ile Glu Lys Thr Gln Arg Met Leu Ser Gly Phe Cys Pro His Lys Val
        100                 105                 110

Ser Ala Gly Gln Phe Ser Ser Leu His Val Arg Asp Thr Lys Ile Glu
    115                 120                 125

Val Ala Gln Phe Val Lys Asp Leu Leu Leu His Leu Lys Lys Leu Phe
    130                 135                 140

Arg Glu Gly Gln Phe Asn
145                 150
```

```
<210> SEQ ID NO 78
<211> LENGTH: 146
<212> TYPE: PRT
<213> ORGANISM: Homo sapiens

<400> SEQUENCE: 78

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Phe Cys Val Ala
65                  70                  75                  80

Leu Asp Ser Leu Thr Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu His Leu Lys Lys Leu Phe Arg Glu Gly Gln
    130                 135                 140

Phe Asn
145

<210> SEQ ID NO 79
<211> LENGTH: 146
<212> TYPE: PRT
<213> ORGANISM: Homo sapiens

<400> SEQUENCE: 79

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Tyr Arg Thr
                85                  90                  95

Gln Arg Ile Leu His Gly Leu Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140

Phe Asn
145

<210> SEQ ID NO 80
<211> LENGTH: 147
<212> TYPE: PRT
```

<213> ORGANISM: Homo sapiens

<400> SEQUENCE: 80

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala His Phe
        115                 120                 125

Ile Thr Lys Leu Leu Ser Tyr Thr Lys Gln Leu Phe Arg His Gly Gln
    130                 135                 140

Gln Phe Asn
145

<210> SEQ ID NO 81
<211> LENGTH: 109
<212> TYPE: PRT
<213> ORGANISM: Homo sapiens

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Met Val Thr Val Ser Ser
            100                 105

<210> SEQ ID NO 82
<211> LENGTH: 108
<212> TYPE: PRT
<213> ORGANISM: Homo sapiens

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Trp Gly Gln Gly Thr Met Val Thr Val Ser Ser
            100                 105

<210> SEQ ID NO 83
<211> LENGTH: 109
<212> TYPE: PRT
<213> ORGANISM: Homo sapiens

<400> SEQUENCE: 83

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Val Thr Val Ser Ser
            100                 105

<210> SEQ ID NO 84
<211> LENGTH: 109
<212> TYPE: PRT
<213> ORGANISM: Homo sapiens

<400> SEQUENCE: 84

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105

<210> SEQ ID NO 85
<211> LENGTH: 108
<212> TYPE: PRT
<213> ORGANISM: Homo sapiens

<400> SEQUENCE: 85

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gln Gly Thr Leu Val Thr Val Ser Ser
                100                 105
```

<210> SEQ ID NO 86
<211> LENGTH: 111
<212> TYPE: PRT
<213> ORGANISM: Homo sapiens

<400> SEQUENCE: 86

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Trp Gly Gln Gly Thr Leu Val Thr Val Ser Ser
                100                 105                 110
```

<210> SEQ ID NO 87
<211> LENGTH: 109
<212> TYPE: PRT
<213> ORGANISM: Homo sapiens

<400> SEQUENCE: 87

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
                100                 105
```

<210> SEQ ID NO 88
<211> LENGTH: 109
<212> TYPE: PRT
<213> ORGANISM: Homo sapiens

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Trp Gly Gln Gly Thr Thr Val Thr Val Ser Ser
        100                 105

<210> SEQ ID NO 89
<211> LENGTH: 98
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Phe Gly Pro Gly Thr Lys Val Asp
            85                  90                  95

Ile Lys

<210> SEQ ID NO 90
<211> LENGTH: 98
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

```
Glu Asp Val Ala Thr Tyr Tyr Cys Phe Gly Pro Gly Thr Lys Val Asp
                 85                  90                  95

Ile Lys

<210> SEQ ID NO 91
<211> LENGTH: 98
<212> TYPE: PRT
<213> ORGANISM: Homo sapiens

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Phe Gly Gln Gly Thr Lys Leu Glu
                85                  90                  95

Ile Lys

<210> SEQ ID NO 92
<211> LENGTH: 97
<212> TYPE: PRT
<213> ORGANISM: Homo sapiens

<400> SEQUENCE: 92

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Phe Gly Thr Gly Thr Lys Val Thr Val
                85                  90                  95

Leu

<210> SEQ ID NO 93
<211> LENGTH: 97
<212> TYPE: PRT
<213> ORGANISM: Homo sapiens

<400> SEQUENCE: 93

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45
```

```
Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Phe Gly Gly Gly Thr Lys Leu Thr Val
                85                  90                  95

Leu

<210> SEQ ID NO 94
<211> LENGTH: 97
<212> TYPE: PRT
<213> ORGANISM: Homo sapiens

<400> SEQUENCE: 94

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Phe Gly Gly Gly Thr Lys Leu Thr Val
                85                  90                  95

Leu

<210> SEQ ID NO 95
<211> LENGTH: 10
<212> TYPE: PRT
<213> ORGANISM: Homo sapiens

<400> SEQUENCE: 95

Thr Gln Asn Gln Lys Ala Pro Leu Cys Asn
 1               5                  10

<210> SEQ ID NO 96
<211> LENGTH: 112
<212> TYPE: PRT
<213> ORGANISM: Homo sapiens

<400> SEQUENCE: 96

Gly Pro Val Pro Pro Ser Thr Ala Leu Arg Glu Leu Ile Glu Glu Leu
 1               5                  10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
        50                  55                  60

Met Leu Ser Gly Phe Cys Pro His Lys Val Ser Ala Gly Gln Phe Ser
 65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
               100                 105                 110
```

FULLY HUMAN MONOCLONAL ANTIBODIES TO IL-13

RELATED APPLICATIONS

This Application claims priority under 35 U.S.C. §119(e) to U.S. Provisional Application Nos. 60/629,135 and 60/728,604, filed Nov. 17, 2004, and Oct. 19, 2005, respectively, which are incorporated by reference in their entireties.

FIELD OF INVENTION

The present invention relates generally to compounds that relate to IL-13. More specifically, the compounds can bind to interleukin-13. More specifically, the invention relates to human monoclonal antibodies that specifically bind interleukin-13 and can affect IL-13 activity.

BACKGROUND OF THE INVENTION

Interleukin-13 (IL-13) is a cytokine that was first recognized for its effects on B cells and monocytes, where it up-regulates class II expression, promotes IgE class switching and inhibits inflammatory cytokine production. The IL-13 receptor shares the IL-4 receptor alpha chain with the IL-4 receptor. As a result, IL-13 has many similar biological activities to IL-4.

IL-13 inhibits proinflammatory cytokine release and has an anti-inflammatory activity in vivo. IL-13 plays a role in IgE mediated allergic responses and is the central mediator of allergic asthma (Wills-Karp M., Curr. Opin. Pulm. Med., 2003; 9:21-27). In the lung it regulates eosinophilic inflammation, mucus secretion, and airway hyperresponsiveness. In addition to asthma, IL-13 is implicated in the pathogenesis of a large number of diseases (Wynn T A. Annu. Rev. Immunol. 2003. 21:425-456).

SUMMARY OF THE INVENTION

Some aspects of the invention relate to an isolated human antibody that binds to IL-13. In some embodiments, the isolated human antibody binds to human IL-13 with a $K_D$ of less than 170 pM. In some embodiments, the isolated human antibody binds to IL-13 with a $K_D$ of less than 50 pM. In some embodiments, the antibody can inhibit airway hyperresponsiveness. In some embodiments, the antibody allows for a complete reversal of airway hyperresponsiveness. In some embodiments, the antibody can reduce mucus production in the lung. In some embodiments, the antibody allows for the reduction of at least about 30% of the mucus production. In some embodiments, the antibody can inhibit an IL-13 related disorder selected from the group consisting of: chronic obstructive pulmonary disease, chronic bronchitis, emphysema, asthma. In some embodiments, the antibody binds to an epitope of IL-13 that prevents IL-13 from signaling through an interaction with an alpha 1 IL-13 receptor. In some embodiments, the antibody has an $IC_{50}$ of no more than 60 pM in an eotaxin release assay with 300 pM of IL-13. In some embodiments, the antibody binds to human IL-13 but does not detectably bind to murine IL-13.

Some aspects of the invention relate to a method of treating an IL-13 related disorder. In some embodiments, the method comprises administering an effective amount of a human antibody that binds to IL-13 to a subject in need of treatment, wherein the isolated human antibody binds to IL-13 with a $K_D$ of no more than 170 pM, thereby treating the IL-13 related disorder.

In some embodiments, the treatment of airway hyperresponsiveness, mucus production, or both in a subject occurs as a prophylactic treatment, and the method further comprises the step of identifying a patient at risk of developing airway hyperresponsiveness, mucus production or both. In some embodiments, the IL-13 related disorder is selected from the group consisting of: airway hyperresponsiveness, mucus production, asthma or some combination thereof. In some embodiments, the antibody has a $K_D$ of no more than about 10 pM. In some embodiments, the IL-13 related disorder is hodgkins lymphoma. In some embodiments, the effective amount is an amount that is sufficient to lower an amount of a detectable biomarker in a patient. In some embodiments, an effective amount is an amount that can reduce the amount of IL-13 present in a subject by and significant amount, for example 1-10, 10-20, 20-30, 30-40, 40-50, 50-60, 60-70, 70-80, 80-90, 90-95, 95-99, 99-100%. In some embodiments, the biomarker is selected from the group consisting of: C10, TARC, eotaxin, and some combination thereof. In some embodiments, the effective amount is at least an amount sufficient to inhibit at least some cell proliferation of HDLM-2, L-1236 cells, or some combination thereof. In some embodiments, the IL-13 related disorder relates to the expression of CD23.

Other aspects of the invention relate to an isolated human antibody that binds to IL-13, wherein the isolated human antibody binds to IL-13 in a manner such that IL-13 can still bind to IL-13 receptor alpha 2, and wherein the isolated human antibody binds to IL-13 in a manner so as to prevent IL-13 from binding to IL-13 receptor alpha 1.

Other aspects of the invention relate to a method for measuring an inhibition of IL-13 activity. In some embodiments, the method comprises administering an antibody to a sample or a subject and measuring an amount of a biomarker released, wherein a decrease in the amount biomarker released correlates with an inhibition of IL-13 activity.

Other aspects of the invention relate to an isolated human antibody to IL-13. The antibody binds IL-13 and IL-13Q110R with a $K_D$ that is less than 170 pM and binds to both IL-13 and IL-13Q110R with $K_D$s that are within 50% of each other. In some embodiments, the antibody binds to IL-13 and IL-13Q110R with effectively the same $K_D$.

Other aspects of the invention relate to a kit for treating IL-13 related disorders. In some embodiments, the kit comprises an IL-13 antibody and a biomarker detector for detecting biomarker levels. In some embodiments, the biomarker is selected from the group consisting of: eotaxin, TARC, C10, and some combination thereof. In some embodiments, the biomarker detector comprises an antibody to a protein selected from the group consisting of: eotaxin, TARC, C10, or some combination thereof.

Other aspects of the invention relate to a method of treating an IL-13 related disorder. In some embodiments, the method comprises administering a first amount of a human antibody that binds to IL-13 to a subject in need of treatment, wherein the isolated human antibody binds to IL-13 with a $K_D$ of no more than 100 pM, detecting an amount of a biomarker to determine a level of IL-13 related activity occurring after the administration of the first amount of the human antibody, and determining if more or less treatment is required based upon the amount of IL-13 activity indicated by said detection of the biomarker. In some embodiments, the method further comprises administering a second amount of a human antibody, wherein said second amount of the antibody is based upon the amount of the biomarker detected. In some embodiments, the second amount of a human antibody is of an antibody that is different from the amount of antibody administered in the first amount of the human antibody. In some embodiments, the determination is achieved by comparing the amount of biomarker determined to either a standard amount of the biomarker for a healthy subject or a set goal amount of the biomarker for a subject. In some embodiments, the biomarker is selected from the group consisting of: TARC, eotaxin, C10, and some combination thereof. In some embodiments, the subject in need of treatment is a subject that will benefit from a prophylactic treatment for the prevention of IL-13 related disorders. In some embodiments, the subject in need of treatment is a subject that will benefit from a therapeutic treatment regarding IL-13 related disorders.

Other aspects of the invention relate to a method for treating asthma. In some embodiments, the method comprises identifying a subject with asthma and administering an effective amount of a human antibody that binds to human IL-13 with a $K_D$ of no more than about 170 pM. In some embodiments, the effective amount is determined by monitoring a level of a biomarker, wherein said effective amount is achieved once the level of the biomarker decreases. In some embodiments, the biomarker is selected from the group consisting of: eotaxin, C10, TARC, and some combination thereof, wherein an increase or lack of sufficient decrease in the level of the biomarker indicates that additional antibody should be administered. In some embodiments, the patient with asthma is identified by the subject having a higher level of a biomarker than a control group.

Other aspects of the invention relate to a method of treating a symptom of an IL-13 related disorder. In some embodiments, the method comprises identifying a subject having a symptom of an IL-13 related disorder by identifying a subject with a symptom that is common to asthma and administering an effective amount of a human antibody to IL-13 to said subject, wherein said effective amount is sufficient to reduce said symptom. In some embodiments, the symptom is selected from the group consisting of the following: airway-hyperresponsiveness, excess mucus production, leukocyte recruitment in bronchoalveolar lavage fluid (BALF), and any combination thereof. In some embodiments, the symptom is a symptom that results in a subject when significant amounts of IL-13 are administered to the subject.

Other aspects of the invention relate to the use of an effective amount of a human antibody that binds to IL-13 in the preparation of a medicament for treating an IL-13 related disorder, wherein the isolated human antibody binds to IL-13 with a $K_D$ of no more than 170 pM. In some embodiments, the IL-13 related disorder is treatment of airway hyperresponsiveness, mucus production, or both, and wherein the treatment is a prophylactic treatment. In some embodiments, the IL-13 related disorder is selected from the group consisting of: airway hyperresponsiveness, mucus production, asthma or some combination thereof. In some embodiments, the antibody has a $K_D$ of no more than about 10 pM. In some embodiments, the IL-13 related disorder is hodgkins lymphoma. In some embodiments, the effective amount is an amount that is sufficient to lower an amount of a detectable biomarker in a patient. In some embodiments, the effective amount is an amount that is sufficient to lower the amount of IL-13 in a subject by any significant amount, for example, 1-10, 10-20, 20-30, 30-40, 40-50, 50-60, 60-70, 70-80, 80-90, 90-95, 95-99, 99-100 percent. In some embodiments, the medicament further comprises a biomarker detector that can report on a level of a biomarker. In some embodiments, the biomarker is selected from the group consisting of: C10, TARC, eotaxin, and some combination thereof. In some embodiments, the biomarker detector comprises an antibody that binds to the biomarker. In some embodiments, the effective amount is at least an amount sufficient to inhibit at least some cell proliferation of HDLM-2, L-1236 cells, or some combination thereof. In some embodiments, the IL-13 related disorder relates to the expression of CD23.

Other aspects of the invention relate to the use of a biomarker detector in the production of a medicament for monitoring the level of a biomarker as it reports on an IL-13 related disorder.

Other aspects of the invention relate to the use of an antibody to IL-13 in the production of a medicament, wherein the antibody binds to IL-13 in a manner such that IL-13 can still bind to IL-13 receptor alpha 2, thereby allowing IL-13 receptor alpha 2 to still function as a sink for IL-13, thereby enhancing the clearance of IL-13 from a subject.

Some embodiments of the invention relate to isolated monoclonal antibodies, or fragments thereof, that specifically bind to IL-13. It will be appreciated that in these embodiments, the isolated antibodies can be monoclonal antibodies, chimeric antibodies and/or human or humanized antibodies. Preferably, the antibodies are human or fully human monoclonal antibodies and bind to IL-13 with an equilibrium dissociation constant lower than 200 pM. In one embodiment, the antibodies bind to IL-13 with a dissociation constant lower than 100 pM. In another embodiment, the antibodies bind to IL-13 with an equilibrium dissociation constant lower than 55 pM. In some embodiments, the antibodies binds to IL-13 with a $K_D$ lower than 200 pM or even lower than 50 pM. In some embodiments, these antibodies, when administered to a patient, inhibit partially or completely airway hyperresponsiveness.

In one embodiment, the antibody is the "623" antibody discussed below having heavy chain SEQ ID NO: 50 and light chain SEQ ID NO: 52. In another embodiment, the antibody is the "731" antibody having heavy chain SEQ ID NO: 38 and light chain SEQ ID NO: 40.

In another embodiment of the invention, the antibodies preferably bind to specific epitopes of IL-13. In one embodiment, the antibody binds to an epitope including amino acids 21-33 of IL-13. In another embodiment, the antibody binds to an epitope including amino acids 109-121 of IL-13. In yet another embodiment, the antibody binds to an epitope including amino acids 111-128. Still another embodiment is an antibody that binds to an epitope including amino acids 45-108 of IL-13. Other embodiments include antibodies that bind to amino acids 70-80 or 83-92 of IL-13. Still another embodiment is an antibody that binds to a specific Helix of IL-13. For example, antibodies that bind to HelixA, HelixC or HelixD of IL-13 are within the scope of the invention. In another embodiment, the antibody binds to an epitope on IL-13, wherein the epitope includes amino acids 20 through 29 of IL-13.

Another embodiment of the invention is an antibody that has a specific heavy chain amino acid sequence. For example, one embodiment is an antibody that specifically binds to IL-13 and has a heavy chain amino acid sequence shown in Table 18 below. Preferably, such antibodies also have a light chain amino acid sequence as shown in Table 19 or 20 below. In one embodiment, the antibodies include human heavy chain immunoglobulin molecules represented by SEQ ID NOs: 2, 6, 10, 14, 18, 22, 26, 30, 34, 38, 42, 46, 50, 54, 58, and 81-88, for example, and the human kappa light chain immunoglobulin molecules represented by SEQ ID NOs 4, 8, 12, 16, 20, 24, 28, 32, 36, 40, 44, 48, 52, 56, 60, and 89-94, for example. Other embodiments include antibody molecules formed by combinations comprising the heavy chain immunoglobulin molecules with light chain immunoglobulin molecules, such as the kappa light chain immunoglobulin molecules, and vice versa, as well as fragments and analogs thereof. In some embodiments, the antibody has a sequence from the heavy chain CDR1, CDR2, CDR3, FR1, FR2, FR3, and/or FR4 or any of the sequences listed in Table 18. In some embodiments, the antibody has a sequence from the light chain CDR1, CDR2, CDR3, FR1, FR2, FR3, and/or J or any of the sequences listed in Tables 19 and 20.

In some embodiments, the antibody above, when administered to a patient, can reduce mucus production in the lung. The reduction can be a partial, or a complete reduction. In some embodiments, these antibodies can be effective for reducing mucus production in a mouse. In some embodiments, the antibody, when administered to a human patient, can inhibit chronic obstructive pulmonary disease, chronic bronchitis, emphysema, and/or asthma.

In some embodiments, the antibody binds to a region of IL-13 that prevents IL-13 from signaling through an interaction with an IL-13 receptor. In some embodiments, the antibody can allow binding of IL-13 to an IL-13 receptor alpha 2, while inhibiting IL-13 signaling through the interaction with the IL-13 receptor alpha 1. In some embodiments, the isolated fully human antibody can inhibit IL-13 dependent signaling by blocking IL-13 from binding to the IL-13 receptor alpha 1.

In some embodiments the antibody has a $K_D$ of no more than 3 nM for a macaque IL-13 protein.

Another embodiment of the invention is a method of inhibiting airway hyperresponsiveness. The method comprises administering an effective amount of a fully human antibody that binds to IL-13 to a subject in need of treatment. In one embodiment, the isolated fully human antibody binds to IL-13 with a $K_D$ of no more than 100 pM and thereby inhibits airway hyperresponsiveness.

Another embodiment of the invention is a method of inhibiting mucus production. The method comprises administering an effective amount of a fully human antibody that binds to IL-13 to a subject in need of such treatment. Preferably, the isolated fully human antibody binds to IL-13 with a $K_D$ of no more than 100 pM and thereby inhibits mucus production.

In some embodiments, the antibody binds to IL-13 with a $K_D$ of no more than about 50 pM. In another embodiment, the antibody binds to IL-13 with a $K_D$ of no more than about 10 pM. In some embodiments, the method is performed on a mouse, while in other embodiments, the method is performed on a human.

In some embodiments, the above antibody has an $IC_{50}$ of no more than about 100 pM, about 50 pM, about 30 pM, and/or about 20 pM.

Still another embodiment is a method of enhancing the clearance of IL-13 from a subject. In some embodiments, the method comprises administering an antibody that can bind to IL-13 to a subject. The antibody preferably binds to IL-13 in a manner such that IL-13 can still bind to IL-13 receptor alpha 2 and thereby allows IL-13 receptor alpha 2 to still function as a "sink" for IL-13, thereby enhancing the clearance of IL-13 from a subject. One such example of an antibody that may be capable of doing this is mAb 731. In another embodiment, the antibody binds to IL-13 in a manner such that IL-13 cannot bind to either of the alpha 1 or alpha 2 receptors.

One other embodiment is a method of suppressing the level of IL-13 dependent activity in a subject. In some embodiments, the method comprises administering an antibody to IL-13 to a subject. The antibody binds to the IL-13 in a manner so as to prevent the IL-13 from signaling through its endogenous receptor. Preferably, the signaling requires the IL-13 to bind to an IL-13 receptor alpha 1, and the antibody binding to the IL-13 does not significantly interfere with the IL-13 binding to an IL-13 receptor alpha 2. In some embodiments, the method further comprises monitoring a level of an IL-13 dependent biomarker and adjusting the amount of antibody administered accordingly. In some embodiments, the antibody is mAb 623, 731, and an antibody that bind to the same epitope as the 623 or 731 antibody. In some embodiments the biomarker is eotaxin, C10 (a CC chemokine), and/or thymus- and activation-regulated chemokine (TARC). Additionally contemplated are biomarker detectors, which are compositions, such as proteins (e.g., antibodies) that can be employed in some manner to detect the level of a biomarker in a sample.

In some embodiments, the method allows for measuring the inhibition of IL-13. The method comprises applying a candidate antibody to a sample comprising IL-13 and measuring the amount of eotaxin released. The inhibition of eotaxin correlates with the binding of an antibody to IL-13. In some embodiments, the method comprises measuring the amount of C10 and/or TARC. In some embodiments, the method can be used to identify a subject suffering from an IL-13 related disorder.

In some embodiments, an isolated variant of IL-13 comprising a point mutation at amino acid position 110 is provided. The point mutation results in a change from a glutamine at position 110 to an arginine residue.

Some embodiments of the invention include an isolated fully human antibody to IL-13, wherein the antibody specifically binds to a variant of IL-13. In some embodiments, the antibody may specifically bind to the IL-13 variant IL-13Q110R more strongly than the antibody binds to IL-13. In some embodiments, the antibody may bind specifically to the variant IL-13Q110R, but does not bind to the wild-type IL-13. In some embodiments the antibody binds to the variant with a $K_D$ of no more than 100 pM. In some embodiments, the antibody may bind to IL-13 more strongly than it does the IL-13 variant IL-13Q110. In some embodiments, the antibody may bind specifically to the wild-type IL-13, but does not detectably bind to the variant IL-13Q110R. In some embodiments, the antibody binds to IL-13 as effectively as it binds to IL-13Q110R. In some embodiments, there is less than a 20% difference in the $K_D$ of the fully human mAb for IL-13 and IL-13Q110R, for example, less than 20-15, 15-10, 10-8, 8-6, 6-4, 4-2, 2-1, 1-0 percent difference in the $K_D$s of the antibody.

In some embodiments, a transgenic mouse is provided. The mouse is humanized and expresses human IL-13. In some embodiments, the mouse is susceptible to allergen-induced airway hyper-reactivity.

In some embodiments, the above monoclonal antibody or antigen-binding portion thereof of is a monoclonal antibody.

In some embodiments, a composition comprising the above monoclonal antibody or antigen-binding portion and a pharmaceutically acceptable carrier is provided.

In some embodiments a kit for treating IL-13 related disorders contains an IL-13 antibody. In some embodiments, the kit comprises an IL-13 antibody disclosed herein and instructions for administering the IL-13 antibody to a subject. In some embodiments, the kit further includes an IL-13 dependent biomarker for determining if more or less antibody is required for treating the IL-13 related disorder.

It will also be appreciated that embodiments of the invention are not limited to any particular form of an antibody. For example, the antibodies provided may be a full length antibody (e.g. having an intact human Fc region) or an antibody fragment (e.g. a Fab, Fab' or F(ab')$_2$). In addition, the antibodies may be manufactured from a hybridoma that secretes the antibody, or, recombinantly, from a cell that has been transformed or transfected with a gene or genes encoding the antibody.

Other embodiments include isolated nucleic acid molecules encoding any of the antibodies described herein.

In yet further embodiments, the invention provides an isolated polynucleotide molecule described herein. As will be appreciated by one of skill in the art, in some embodiments, any of the presently disclosed antibodies or variants thereof can be used in or for any of the described embodiments or aspects, as appropriate.

BRIEF DESCRIPTION OF THE DRAWINGS

The invention will be better understood from the Detailed Description and from the appended drawings, which are meant to illustrate and not to limit the invention.

FIG. 10 is a depiction of an amino acid sequence highlighting a binding site of mAb 623.

DETAILED DESCRIPTION

Figure 1:
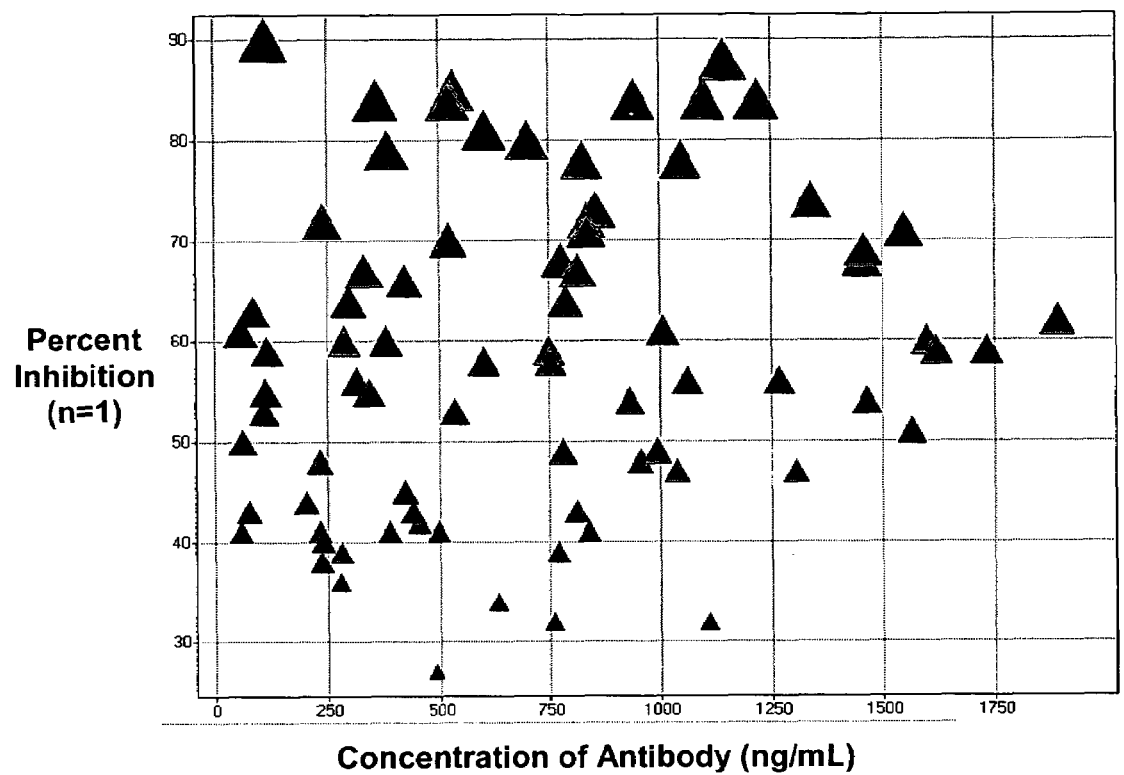
FIG. 1 shows a plot of the relative antibody concentration against neutralization data for each well. The data was used to identify wells with the highest potency antibodies.

Some embodiments of the invention relate to isolated antibodies that bind to IL-13 and methods of using those antibodies to treat diseases in humans. Preferably the antibodies are fully human monoclonal antibodies that bind to IL-13 with high affinity, high potency, or both. In one embodiment, the antibodies, or antibody fragments, specifically bind to regions of the IL-13 molecule that prevent it from signaling through the IL-13 receptor complex. In one embodiment, the fully human monoclonal antibodies are neutralizing towards IL-13 based activity.

In another embodiment of the invention, the antibodies bind to IL-13 while allowing it to bind to a receptor, other than the IL-13 receptor alpha 1. For example, in one embodiment, the antibody binds to IL-13 and allows IL-13 to bind to a decoy receptor known as IL-13 receptor alpha 2. In this case, the antibody prevents IL-13 from binding to its signaling receptor, but not to the decoy receptor. Embodiments of the invention also include cells for producing these antibodies.

In addition, embodiments of the invention include methods of using these anti-IL-13 antibodies as a diagnostic agent or treatment for a disease. For example, the antibodies are useful for treating asthma, including both allergic (atopic) and non-allergic (non-atopic), bronchial asthma, chronic bronchitis, emphysema, chronic obstructive pulmonary disease (COPD), hay fever, rhinitis, urticaria, angioedema, allergic dermatitis, including contact dermatitis, Stevens-Johnson syndrome, anaphylatctic shock, food allergies, keratitis, conjunctivitis, steroid-resistant nephritic syndrome, mastocytosis, fibrotic disease such as lung fibrosis, including idiopathic pulmonary fibrosis, cystic fibrosis, bleomycin-induced fibrosis, hepatic fibrosis and systemic sclerosis, cancers, such as Hodgkin's disease, B-cell proliferative disorders such as B-cell lymphoma, particularly mediastinal large B-cell lymphoma, B-cell leukemias, ovarian carcinoma, diseases characterized by non-malignant B-cell proliferation such as systemic lupus erythematosus, rheumatoid arthritis, chronic active hepatitis and cryoglobulinemias, high levels of autoantibodies, such as hemolytic anemia, thrombocytopenia, phospholipids syndrome and pemphigus, inflammatory bowel disease and graft-versus-host disease. In some embodiments, the method of treatment further comprises checking the effectiveness of the administration of the antibody by following the level of a biomarker, such as eotaxin, TARC and/or C10.

In association with such treatment, embodiments of the invention include articles of manufacture comprising the antibodies. One embodiment of the invention is an assay kit comprising IL-13 antibodies that is used to screen for diseases or disorders associated with IL-13 activity. In some embodiments, the kit includes a biomarker, allowing one to determine the effectiveness of the antibody in a particular patient.

Additionally, antibodies to IL-13 have been used to influence interleukin-13's (IL-13) role as an effector cytokine, which plays a role in the pathogenesis of asthma and other disorders. In animals, direct administration of IL-13 induces asthma, and blockade of IL-13 inhibits IL-13-induced or allergen-induced asthma. As shown herein, mAb 623 binds with high affinity to IL-13 ($K_D$=24 pM) and IL-13R130Q ($K_D$=39 pM), a common IL-13 variant associated with allergy and asthma. Furthermore, it is presently shown that mAb 623 prevents IL-13 from binding to IL-13Rα1 and IL-13Rα2. In vitro, mAb 623 inhibits IL-13-induced eotaxin-1 production by human dermal fibroblast (HDFa) cells, and IL-13-induced CD23 up-regulation on whole blood B cells. Additionally, mAb 623 also inhibits cell proliferation of HDLM-2 and L-1236 cells, two Hodgkin's lymphoma-derived cell lines that use IL-13 as an autocrine growth factor. Thus, the antibody appears to have a wide range of desirable characteristics relating to treating disorders relating to IL-13.

Additionally, a mouse model designed for examining asthma has also been developed and tested. As mAb 623 does not bind to murine IL-13, IL-13 KI/KO mice were generated by replacing the first exon of the murine IL-13 gene with the cDNA encoding human IL-13, thereby allowing human IL-13 to be expressed under the murine IL-13 promoter and removing the expression of the endogenous murine IL-13 gene. Using these mice to establish an OVA-induced asthma model, it is herein shown that prophylactic administration of mAb 623 blocks airway hyperreactivity (AHR) and significantly suppresses mucus hyperplasia. Furthermore, in a house dust mite-induced asthma model, prophylactic or therapeutic administration of mAb 623 inhibits AHR, mucus hyperplasia and eosinophil infiltration in the airways.

Additionally, mAb 623 also inhibits OVA-induced elevation of TARC and eotaxin-1 serum levels, demonstrating that these compounds can be useful as biomarkers. Additionally, these data show that mAb 623 and other antibodies can effectively neutralize IL-13 in vitro and in vivo. The antibodies disclosed herein, as well as those created from the disclosed methods, can also be used and can exhibit similar properties.

Methods for screening and verifying the particular properties of the antibodies are provided herein.

The nucleic acids described herein, and fragments and variants thereof, may be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully below.

In some aspects, methods of identifying these antibodies are provided. In one embodiment, the method involves an eotaxin release assay.

In some aspects, antibodies that bind to a variant of IL-13 are also provided. Especially relevant are those antibodies that bind to an IL-13 variant with a Glutamine at position 110 of the endogenous IL-13 polypeptide.

In some aspects, a mouse that is genetically altered to produce only human IL-13 is provided. This mouse is useful for providing a test subject for airway hyperresponsiveness and inhibition of mucus production.

In some aspects, the antibodies can be used for the prophylactic treatment or prevention of asthma or any of the herein disclosed disorders. For example, in some embodiments, the antibody can be used to prophylactically treat any of the following: inflammatory diseases, cancer, fibrotic disease and diseases characterized by non-malignant cell proliferation; inflammatory diseases or disorders such as asthma, including both allergic (atopic) and non-allergic (non-atopic), bronchial asthma, chronic bronchitis, emphysema, chronic obstructive pulmonary disease (COPD), hay fever, rhinitis, urticaria, angioedema, allergic dermatitis, including contact dermatitis, Stevens-Johnson syndrome, anaphylactic shock, food allergies, keratitis, conjunctivitis, steroid-resistant nephritic syndrome; mastocytosis; fibrotic disease such as lung fibrosis, including idiopathic pulmonary fibrosis, cystic fibrosis, bleomycin-induced fibrosis, hepatic fibrosis and systemic sclerosis. In further embodiments the anti-IL-13 antibodies are used to treat cancers, such as Hodgkin's disease, B-cell proliferative disorders such as B-cell lymphoma, particularly mediastinal large B-cell lymphoma, B-cell leukemias, ovarian carcinoma. The antibody can be administered before or during any risk of the disease. In some embodiments, the antibody is given in a single dose or multiple doses. In some embodiments, the antibody is administered continuously. In chronic conditions, the antibody can be administered in larger doses and/or continuously. In acute conditions, the antibody can be administered in a single or low dose, or relatively infrequently.

In some embodiments, the methods disclosed herein can be used for identifying biomarkers for a disease or biological events relating to or impacting IL-13. In some embodiments, the biomarker is selected from the group consisting of: C10, TARC, eotaxin, and some combination thereof. In some embodiments, one monitors the level of C10, TARC and/or eotaxin in a subject that can benefit from the monitoring of a biomarker relating to IL-13. In some embodiments, one administers the antibody to a patient, e.g., mAb 623, and then monitors the level of the biomarker to verify the effectiveness of the antibody. In some embodiments, one then adjusts the amount of antibody administered to the patient. In some embodiments, molecules that bind to and detect these biomarkers ("biomarker detectors"), and their use to detect the biomarkers, in connection with determining the effectiveness of treating an IL-13 related disorder is contemplated. For example, antibodies to these markers are also useful for the detection of the biomarkers.

Definitions:

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art, as described in various general and more specific references such as those that are cited and discussed throughout the present specification. See e.g. Singleton et al., *Dictionary of Microbiology and Molecular Biology* $2^{nd}$ ed., J. Wiley & Sons (New York, N.Y. 1994); Sambrook et al. Molecular Cloning: A Laboratory Manual (2d ed., Cold Spring Harbor Laboratory Press, Cold Spring Harbor, N.Y. (1989)), which is incorporated herein by reference. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. Standard techniques are also used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

"Polymerase chain reaction" or "PCR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Pres, NY, 1989). A used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985); Novotny and Haber, *Proc. Natl. Acad. Sci. U.S.A.* 82:4592 (1985); Chothia et al., *Nature* 342:877-883 (1989)).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments including Fab and F(ab)'2, so long as they exhibit the desired biological activity. The "light chains" of antibodies (immunoglobulins) from any vertebrate species can be assigned to one of two clearly distinct types, called κ and λ, based on the amino acid sequences of their constant domains. Binding fragments are produced by recombinant DNA techniques, or by enzymatic or chemical cleavage of intact antibodies. Binding fragments include Fab, Fab', $F(ab')_2$, Fv, and single-chain antibodies, as described in more detail below. An antibody other than a "bispecific" or "bifunctional" antibody is understood to have each of its binding sites identical.

Preferred antibodies are neutralizing and inhibit binding of IL-13 to a signaling receptor, such as IL-13 receptor alpha-1 (IL-13Rα1) by at least about 20%, 40%, 60% or 80%, and more usually greater than about 85% (as measured in an in vitro competitive binding assay). In some embodiments the antibodies also inhibit binding to the decoy receptor IL-13Rα2, while in other embodiments the ability of IL-13 to bind IL-13Rα2 is maintained upon antibody binding to IL-13.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and terminal or internal amino acid sequence by use of a spinning cup sequenator, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "neutralizing antibody" is an antibody molecule that is able to eliminate or significantly reduce an effector function of a target antigen to which it binds. Accordingly, a "neutralizing" IL-13 antibody is capable of eliminating or significantly reducing an effector function, such as IL-13 signaling activity through the IL-13 receptor. In one embodiment, a neutralizing antibody will reduce an effector function by 1-10, 10-20, 20-30, 30-50, 50-70, 70-80, 80-90, 90-95, 95-99, 99-100%.

"Antibody-dependent cell-mediated cytotoxicity" and "ADCC" refer to a cell-mediated reaction in which non-specific cytotoxic cells that express Ig Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarized in Table 3 on page 464 of Ravetch and Kinet, *Annu. Rev. Immunol.* 9:457-492 (1991). To assess ADCC activity of a molecule of interest, an in vitro ADCC assay, such as that described in U.S. Pat. No. 5,500,362, or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1988).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the Ig light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991)). The constant domains are not involved directly in binding an antibody to an antigen, but exhibit various effector functions, such as participation of the antibody in antibody-dependent cellular toxicity.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

"Fv" is the minimum antibody fragment that contains a complete antigen-binding recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain Kabat et al., *Sequences of Proteins of Immunological Interest*, 5$^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "complementarity determining regions" or "CDRs" when used herein refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for antibodies on protein antigens. Epitopic determinants usually consist of chemically active surface groupings of molecules such as amino acids or sugar side chains and usually have specific three dimensional structural characteristics, as well as specific charge characteristics. An antibody is said to bind an antigen when the dissociation constant is ≦1 µM, preferably ≦100 nM and most preferably ≦10 nM. An increased or greater equilibrium constant ("$K_D$") means that there is less affinity between the epitope and the antibody. In other words, that the antibody and the epitope are less favorable to bind or stay bound together. A decreased or lower equilibrium constant means that there is a higher affinity between the epitope and the antibody. In other words, it is more likely that the antibody and the epitope will bind or stay bound together. An antibody with a $K_D$ of "no more than" a certain amount means that the antibody will bind to the epitope with the given $K_D$, or more strongly (or tightly). In some embodiments, the antibody binds with a $K_D$ of no more than 200 pm, for example, 200-180, 180-170, 170-60, 160-150, 150-140, 140-130, 130-120, 12-100, 100-80, 80-60, 60-50, 50-40, 40-30, 30-20, 20-10, 10-1,1-0.1 pM or less.

While $K_D$ describes the binding characteristics of an epitope and an antibody, "potency" describes the effectiveness of the antibody itself for a function of the antibody. A relatively low $K_D$ does not automatically mean a high potency. Thus, antibodies can have a relatively low $K_D$ and a high potency (e.g., they bind well and alter the function strongly), a relatively high $K_D$ and a high potency (e.g., they don't bind well but have a strong impact on function), a relatively low $K_D$ and a low potency (e.g., they bind well, but not in a manner effective to alter a particular function) or a relatively high $K_D$ and a low potency (e.g., they simply do not bind to the target well). In one embodiment, high potency means that there is a high level of inhibition with a low concentration of antibody. In one embodiment, an antibody is potent or has a high potency when its $IC_{50}$ is a small value, for example, 130-110, 110-90, 90-60, 60-30, 30-25, 25-20, 20-15, or less pM.

"Substantially," unless otherwise specified in conjunction with another term, means that the value can vary within the any amount that is contributable to errors in measurement that may occur during the creation or practice of the embodiments. "Significant" means that the value can vary as long as it is sufficient to allow the claimed invention to function for its intended use.

The term "selectively bind" in reference to an antibody does not mean that the antibody only binds to a single substance. Rather, it denotes that the $K_D$ of the antibody to a first substance is less than the $K_D$ of the antibody to a second substance. Antibodies that exclusively bind to an epitope only bind to that single epitope.

The term "amino acid" or "amino acid residue," as used herein, refers to naturally occurring L amino acids or to D amino acids as described further below with respect to variants. The commonly used one and three-letter abbreviations for amino acids are used herein (Bruce Alberts et al., *Molecular Biology of the Cell*, Garland Publishing, Inc., New York (3d ed. 1994)).

The term "and/or" denotes 1) including all of the relevant options, 2) including only one (or a subset) of a number of alternative options, 3) including both of the previous descriptions (1) or 2)), and 4) including only one of the previous descriptions (1) or 2)).

The term "mAb" refers to monoclonal antibody.

The term "XENOMOUSE®" refers to strains of mice which have been engineered to contain 245 kb and 190 kb-sized germline configuration fragments of the human heavy chain locus and kappa light chain locus, as described in Green et al. *Nature Genetics* 7:13-21 (1994), incorporated herein by reference. The XENOMOUSE® strains are available from Abgenix, Inc. (Fremont, Calif.).

The term "XENOMAX®" refers use of to the use of the "Selected Lymphocyte Antibody Method" (Babcook et al., *Proc. Natl. Acad. Sci. USA*, 93:7843-7848 (1996)), when used with XENOMOUSE® animals.

The term "SLAM®" refers to the "Selected Lymphocyte Antibody Method" (Babcook et al., *Proc. Natl. Acad. Sci. USA*, 93:7843-7848 (1996), and Schrader, U.S. Pat. No. 5,627,052), both of which are incorporated by reference in their entireties.

The terms "disease," "disease state" and "disorder" refer to a physiological state of a cell or of a whole mammal in which an interruption, cessation, or disorder of cellular or body functions, systems, or organs has occurred.

The term "symptom" means any physical or observable manifestation of a disorder, whether it is generally characteristic of that disorder or not. The term "symptoms" can mean all such manifestations or any subset thereof.

The term "treat" or "treatment" refer to both therapeutic treatment and prophylactic or preventative measures, wherein the object is to prevent or slow down (lessen) an undesired physiological change or disorder, such as the development or spread of cancer or asthma. "Prophylactic treatment" includes occurrences when a treatment decreases the likelihood a subject will become sick or increases the amount of time required for the subject to become sick or exhibit symptoms or conditions associated with the disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The term "inhibit," when used in conjunction with a disease or symptom can mean that the antibody can reduce or eliminate the disease or symptom. Prophylactic treatment need not completely prevent the disease or symptoms. In some embodiments, it delays the onset of the disease. In other embodiments, it reduces the intensity of the disease or symptoms. In some embodiments, the reduction can be any amount, for example, 1-10, 10-20, 20-30, 30-40, 40-50, 50-60, 60-70, 70-80, 80-90, 90-95, 95-99, 99-100% reduction. The term treatment can include similar amounts of improvement or recovery as well.

The term "patient" includes human and veterinary subjects.

"Administer," for purposes of treatment, means to deliver to a patient. For example and without limitation, such delivery can be intravenous, intraperitoneal, by inhalation, intramuscular, subcutaneous, oral, topical, transdermal, or surgical.

"Therapeutically effective amount," for purposes of treatment, means an amount such that an observable change in the patient's condition and/or symptoms could result from its administration, either alone or in combination with other treatment. As discussed herein, and as will be appreciated by one of skill in the art, there are a variety of ways in which an effective amount can be determined. For example, an effective amount can be an amount required to reduce the amount of a biomarker by any significant amount, including, for example, 0-1, 1-5, 5-10, 10-20, 20-30, 30-40, 40-50, 505-60, 60-70, 70-80, 80-90, 90-95, 95-99, 99-100% of a reduction in the biomarker. Alternatively, the amount can be an amount required to reduce a similar percent of the amount of IL-13 present in a subject.

An "IL-13 related disorder" is any disease, disorder, or similar such term in which IL-13 regulates or influences the disease, optionally including the symptoms of the disease.

Examples include inflammatory diseases, cancer, fibrotic disease diseases characterized by non-malignant cell proliferation, asthma, including both allergic (atopic) and non-allergic (non-atopic), bronchial asthma, chronic bronchitis, emphysema, chronic obstructive pulmonary disease (COPD), hay fever, rhinitis, urticaria, angioedema, allergic dermatitis, including contact dermatitis, Stevens-Johnson syndrome, anaphylactic shock, food allergies, keratitis, conjunctivitis, steroid-resistant nephritic syndrome, mastocytosis fibrotic disease such as lung fibrosis, including idiopathic pulmonary fibrosis, cystic fibrosis, bleomycin-induced fibrosis, hepatic fibrosis and systemic sclerosis, cancers, such as Hodgkin's disease, B-cell proliferative disorders such as B-cell lymphoma, particularly mediastinal large B-cell lymphoma, B-cell leukemias, ovarian carcinoma, diseases characterized by non-malignant B-cell proliferation such as systemic lupus erythematosus, rheumatoid arthritis, chronic active hepatitis and cryoglobulinemias; disease characterized by high levels of autoantibodies, such as hemolytic anemia, thrombocytopenia, phospholipids syndrome and pemphigus; inflammatory bowel disease; and graft-versus-host disease. In some embodiments, an "IL-13 ligand dependent disorder" is any of the above that can be directly influenced by the binding of an antibody to IL-13. In other words, the disorder is directly the result of excessive amounts of IL-13. In some embodiments, an IL-13 antibody treatable disorder is any of the above that can be effectively treated by the addition of one of the presently disclosed antibodies. Altering "IL-13 related activity" can include treating any of the above disorders with an antibody; it can also include other, nontherapeutic or prophylactic uses of the antibody which may alter the activity of IL-13. In some embodiments, "IL-13 related disorder" can encompass any disorder in which an elevated level of IL-13 is present in the patient. In some embodiments, "IL-13 related disorder" can encompass any disorder that has a phenotype that is characteristic of IL-13. Phenotypes that are characteristic of a patient with an IL-13 related disorder can be determined and observed by administering an amount of IL-13 to a patient to induce various phenotypes. The amount of IL-13 administered can vary and can be routinely determined by one of skill in the art. In some embodiments, and IL-13 related disorder is one which is a TH2 cytokine mediated or related disorder.

As used herein, the term "biomarker" can encompass any molecule that can track or follow the level of IL-13 related activity or concentration in a sample. Examples of IL-13 biomarkers include C10, TARC, and eotaxin. A "biomarker detector" is any molecule or technique, which allows one to determine the amount, and in some embodiments, the change in the amount, of the biomarker in a sample. For example, antibodies to the biomarker, ligands or receptors to the biomarker, various small peptides that bind to the receptor would all be included as types of biomarker detectors.

A "pharmaceutically acceptable vehicle," for the purposes of treatment, is a physical embodiment that can be administered to a patient. Pharmaceutically acceptable vehicles can be, but are not limited to, pills, capsules, caplets, tablets, orally administered fluids, injectable fluids, sprays, aerosols, lozenges, neutraceuticals, creams, lotions, oils, solutions, pastes, powders, vapors, or liquids. One example of a pharmaceutically acceptable vehicle is a buffered isotonic solution, such as phosphate buffered saline (PBS).

"Neutralize," for purposes of treatment, means to partially or completely suppress chemical and/or biological activity.

"Down-regulate," for purposes of treatment, means to lower the level of a particular target composition.

"Mammal" for purposes of treatment refers to any animal classified as a mammal, including humans, domestic and farm animals, and zoo, sports, or pet animals, such as monkeys, dogs, horses, cats, cows, etc.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a gene mutant. Oligonucleotides can be either sense or antisense oligonucleotides.

The term "naturally occurring nucleotide" as used herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach,* pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

The term "control sequence" as used herein refers to polynucleotide sequences which are necessary to effect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules represented by SEQ ID NOs: 2, 6, 10, 14, 18, 22, 26, 30, 34, 38, 42, 46, 50, 54, 58, and 81-88, for example, and the human kappa light chain immunoglobulin molecules represented by SEQ ID NOs 4, 8, 12, 16, 20, 24, 28, 32, 36, 40, 44, 48, 52, 56, 60, and 89-94, for example, as well as antibody molecules formed by combinations comprising the heavy chain immunoglobulin molecules with light chain immunoglobulin molecules, such as the kappa light chain immunoglobulin molecules, and vice versa, as well as fragments and analogs thereof. In some embodiments, the antibody has a sequence from the heavy chain CDR1, CDR2, CDR3, FR1, FR2, FR3, and/or FR4 or any of the sequences listed in Table 18. In some embodiments, the antibody has a sequence from the light chain CDR1, CDR2, CDR3, FR1, FR2, FR3, and/or J or any of the sequences listed in tables 19 and 20.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as alpha-, alpha-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are among those used to describe the sequence relationships between two or more polynucleotide or amino acid sequences: "reference sequence", "comparison window", "sequence identity", "percentage of sequence identity", "substantial identity", and "homology." A "reference sequence" is a defined sequence used as a basis for a sequence comparison. A reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity.

A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window may include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

Two amino acid sequences or polynucleotide sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family.

For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein.

Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). The foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physiocochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long. In other embodiments polypeptide fragments are at least 25 amino acids long, more preferably at least 50 amino acids long, and even more preferably at least 70 amino acids long.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger TINS p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human-antibody, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), incorporated herein by reference.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. (See generally, *Fundamental Immunology* Ch. 7 (Paul, W., ed., 2nd ed. Raven Press, N.Y. (1989)), incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. (See, e.g., Songsivilai & Lachmann *Clin. Exp. Immunol.* 79: 315-321 (1990), Kostelny et al. *J. Immunol.* 148:1547-1553 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies. Unless specifically identified herein, "human" and "fully human" antibodies can be used interchangeably herein. The term "fully human" can be useful when distinguishing antibodies that are only partially human from those that are completely, or fully human.

One method for generating fully human antibodies is through the use of XENOMOUSE® strains of mice which have been engineered to contain 245 kb and 190 kb-sized germline configuration fragments of the human heavy chain locus and kappa light chain locus. See Green et al. *Nature Genetics* 7:13-21 (1994). The XENOMOUSE® strains are available from Abgenix, Inc. (Fremont, Calif.).

The production of the XENOMOUSE® is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146-156 (1997) and Green and Jakobovits *J. Exp. Med.* 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, 5,814,318, 5,877,397, 5,874,299, and 6,255,458 each to Lonberg and Kay, U.S. Pat. Nos. 5,591, 669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053, 131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference in their entireties.

Human anti-mouse antibody (HAMA) responses have also led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against multimeric enzymes in order to vitiate concerns and/or effects of HAMA or HACA response.

Preparation of Antibodies

Antibodies, as described herein, were prepared using the XENOMOUSE® technology, as described below. Such mice are capable of producing human immunoglobulin molecules and antibodies and are deficient in the production of murine immunoglobulin molecules and antibodies. Technologies utilized for achieving the same are disclosed in the patents, applications, and references referred to herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through use of such technology, fully human monoclonal antibodies to IL-13 were produced, as described in detail below. Essentially, XENOMOUSE® lines of mice were immunized with human IL-13, lymphatic cells (such as B-cells) were recovered from mice that expressed antibodies, and the recovered cell lines were fused with a myeloid-type cell line to prepare immortal hybridoma cell lines. These hybridoma cell lines were screened and selected to identify hybridoma cell lines that produced antibodies specific to the IL-13. Further, provided herein are characterization of the antibodies produced by such cell lines, including nucleotide and amino acid sequence analyses of the heavy and light chains of such antibodies.

Alternatively, instead of being fused to myeloma cells to generate hybridomas, the recovered cells, isolated from immunized XENOMOUSE® lines of mice, can be screened further for reactivity against the initial antigen, preferably human IL-13. Such screening includes an ELISA with the desired IL-13 protein and functional assays such as IL-13-induced eotaxin-1 production. Single B cells secreting antibodies that specifically bind to IL-13 can then be isolated using a desired IL-13-specific hemolytic plaque assay (Babcook et al., *Proc. Natl. Acad. Sci. USA*, i93:7843-7848 (1996)). Cells targeted for lysis are preferably sheep red blood cells (SRBCs) coated with IL-13. In the presence of a B cell culture secreting the immunoglobulin of interest and complement, the formation of a plaque indicates specific IL-13-mediated lysis of the target cells.

The single antigen-specific plasma cell in the center of the plaque can be isolated and the genetic information that encodes the specificity of the antibody isolated from the single plasma cell. Using reverse-transcriptase PCR, the DNA encoding the variable region of the antibody secreted can be cloned. Such cloned DNA can then be further inserted into a suitable expression vector, preferably a vector cassette such as a pcDNA (Invitrogen, Carlsbad, Calif.), more preferably such a pcDNA vector containing the constant domains of immunoglobulin heavy and light chain. The generated vector can then be transfected into host cells, preferably CHO cells, and cultured in conventional nutrient media modified as appropriate for inducing promoters, selecting transformants, or amplifying the genes encoding the desired sequences.

Herein, is described the isolation of multiple single plasma cells that produce antibodies specific to IL-13. Further, the genetic material that encoded an antibody that specifically bound IL-13 was isolated, and that material was introduced into a suitable expression vector and thereafter transfected into host cells.

In general, antibodies produced by the above-mentioned cell lines possessed fully human IgG1 or IgG2 heavy chains with human kappa light chains. The antibodies possessed high affinities, typically possessing KD's of from about $10^{-9}$ through about $10^{-13}$ M, when measured by either solid phase and solution phase.

As mentioned above, anti-IL-13 antibodies can be expressed in cell lines other than hybridoma cell lines. Sequences encoding particular antibodies can be used for transformation of a suitable mammalian host cell, such as a CHO cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with IL-13 binding properties.

Antibody Sequences

The heavy chain and light chain variable region nucleotide and amino acid sequences of representative human anti-IL-13 antibodies are provided in the sequence listing, the contents of which are summarized in Table 1 below.

TABLE 1

| mAb ID No.: | Sequence | SEQ ID NO: |
|---|---|---|
| 11.18 | Amino acid sequence encoding the variable region of the heavy chain | 2 |
|  | Nucleotide sequence encoding the variable region of the heavy chain | 1 |
|  | Amino acid sequence encoding the variable region of the light chain | 4 |
|  | Nucleotide sequence encoding the variable region of the light chain | 3 |
| 353 | Amino acid sequence encoding the variable region of the heavy chain | 6 |
|  | Nucleotide sequence encoding the variable region of the heavy chain | 5 |
|  | Amino acid sequence encoding the variable region of the light chain | 8 |
|  | Nucleotide sequence encoding the variable region of the light chain | 7 |
| 356 | Amino acid sequence encoding the variable region of the heavy chain | 10 |
|  | Nucleotide sequence encoding the variable region of the heavy chain | 9 |
|  | Amino acid sequence encoding the variable region of the light chain | 12 |
|  | Nucleotide sequence encoding the variable region of the light chain | 11 |
| 264 | Amino acid sequence encoding the variable region of the heavy chain | 14 |
|  | Nucleotide sequence encoding the variable region of the heavy chain | 13 |
|  | Amino acid sequence encoding the variable region of the light chain | 16 |
|  | Nucleotide sequence encoding the variable region of the light chain | 15 |
| 243 | Amino acid sequence encoding the variable region of the heavy chain | 18 |
|  | Nucleotide sequence encoding the variable region of the heavy chain | 17 |
|  | Amino acid sequence encoding the variable region of the light chain | 20 |
|  | Nucleotide sequence encoding the variable region of the light chain | 19 |
| 157 | Amino acid sequence encoding the variable region of the heavy chain | 22 |
|  | Nucleotide sequence encoding the variable region of the heavy chain | 21 |
|  | Amino acid sequence encoding the variable region of the light chain | 24 |
|  | Nucleotide sequence encoding the variable region of the light chain | 23 |

TABLE 1-continued

| mAb ID No.: | Sequence | SEQ ID NO: |
|---|---|---|
| 176 | Amino acid sequence encoding the variable region of the heavy chain | 26 |
| | Nucleotide sequence encoding the variable region of the heavy chain | 25 |
| | Amino acid sequence encoding the variable region of the light chain | 28 |
| | Nucleotide sequence encoding the variable region of the light chain | 27 |
| 183 | Amino acid sequence encoding the variable region of the heavy chain | 30 |
| | Nucleotide sequence encoding the variable region of the heavy chain | 29 |
| | Amino acid sequence encoding the variable region of the light chain | 32 |
| | Nucleotide sequence encoding the variable region of the light chain | 31 |
| 713 | Amino acid sequence encoding the variable region of the heavy chain | 34 |
| | Nucleotide sequence encoding the variable region of the heavy chain | 33 |
| | Amino acid sequence encoding the variable region of the light chain | 36 |
| | Nucleotide sequence encoding the variable region of the light chain | 35 |
| 731 | Amino acid sequence encoding the variable region of the heavy chain | 38 |
| | Nucleotide sequence encoding the variable region of the heavy chain | 37 |
| | Amino acid sequence encoding the variable region of the light chain | 40 |
| | Nucleotide sequence encoding the variable region of the light chain | 39 |
| 693 | Amino acid sequence encoding the variable region of the heavy chain | 42 |
| | Nucleotide sequence encoding the variable region of the heavy chain | 41 |
| | Amino acid sequence encoding the variable region of the light chain | 44 |
| | Nucleotide sequence encoding the variable region of the light chain | 43 |
| 643 | Amino acid sequence encoding the variable region of the heavy chain | 46 |
| | Nucleotide sequence encoding the variable region of the heavy chain | 45 |
| | Amino acid sequence encoding the variable region of the light chain | 48 |
| | Nucleotide sequence encoding the variable region of the light chain | 47 |
| 623 | Amino acid sequence encoding the variable region of the heavy chain | 50 |
| | Nucleotide sequence encoding the variable region of the heavy chain | 49 |
| | Amino acid sequence encoding the variable region of the light chain | 52 |
| | Nucleotide sequence encoding the variable region of the light chain | 51 |
| 602 | Amino acid sequence encoding the variable region of the heavy chain | 54 |
| | Nucleotide sequence encoding the variable region of the heavy chain | 53 |
| | Amino acid sequence encoding the variable region of the light chain | 56 |
| | Nucleotide sequence encoding the variable region of the light chain | 55 |
| 785 | Amino acid sequence encoding the variable region of the heavy chain | 58 |
| | Nucleotide sequence encoding the variable region of the heavy chain | 57 |
| | Amino acid sequence encoding the variable region of the light chain | 60 |
| | Nucleotide sequence encoding the variable region of the light chain | 59 |

Antibody Therapeutics

Anti-IL-13 antibodies have therapeutic value for treating symptoms and conditions related to IL-13 activity (e.g., an IL-13 related disorder). IL-13 has been implicated in a wide variety of diseases and disorders, including inflammatory diseases, cancer, fibrotic disease and diseases characterized by non-malignant cell proliferation. In specific embodiments, the anti-IL-13 antibodies disclosed herein are used in the treatment of inflammatory diseases or disorders such as asthma, including both allergic (atopic) and non-allergic (non-atopic), bronchial asthma, chronic bronchitis, emphysema, chronic obstructive pulmonary disease (COPD), hay fever, rhinitis, urticaria, angioedema, allergic dermatitis, including contact dermatitis, Stevens-Johnson syndrome, anaphylactic shock, food allergies, keratitis, conjunctivitis, steroid-resistant nephritic syndrome. In other embodiments they are used to treat mastocytosis. In still other embodiments they are used to treat fibrotic disease such as lung fibrosis, including idiopathic pulmonary fibrosis, cystic fibrosis, bleomycin-induced fibrosis, hepatic fibrosis and systemic sclerosis. In further embodiments the anti-IL-13 antibodies are used to treat cancers, such as Hodgkin's disease, B-cell proliferative disorders such as B-cell lymphoma, particularly mediastinal large B-cell lymphoma, B-cell leukemias, ovarian carcinoma.

In still further embodiments the anti-IL-13 antibodies are used to treat diseases characterized by non-malignant B-cell proliferation such as systemic lupus erythematosus, rheumatoid arthritis, chronic active hepatitis and cryoglobulinemias; disease characterized by high levels of autoantibodies, such as hemolytic anemia, thrombocytopenia, phospholipids syndrome and pemphigus; inflammatory bowel disease; and graft-versus-host disease. In some embodiments, the antibodies are used for the treatment or prevention of asthma in humans, mice, or other animals.

In some embodiments, the use of the antibodies in a medicament for the treatment of an IL-13 related disorder (a disease, condition, etc., relating to IL-13) is contemplated. The medicament can contain a therapeutically effective amount of the antibody. In some embodiments, the amount of IL-13 in the medicament is sufficient so that at least one beneficial result is observed, e.g., a lessening of a symptom. In some embodiments, the amount that is administered removes all of the symptoms of the IL-13 related disorder. In some embodiments, the amount is sufficient so that the level of a biomarker decreases in a subject after the medicament has been administered. In some embodiments, the amount of the antibody administered is about 0.001 to 1000, 0.1 to 160, 0.5 to 50, 1 to 10, 1, 3, or 10 mg of antibody/kg of subject. As will be appreciated by one of skill in the art, the actual amount of the antibody can depend upon the particular disorder (e.g., asthma, is it acute or chronic), the method of administration, the frequency of administration, the desired result, the characteristics of the patient, and the characteristics of the antibody. The actual amount administered can be determined by one of skill in the art, through routine experimentation, in light of the present disclosure. In some embodiments, a single dose will be sufficient. In other embodiments, multiple or continuous doses can be beneficial. The actual amount and method of administration can be determined through the use of, among other techniques, the biomarkers and examples described herein. For example, eotaxin, C10, and/or TARC levels can be monitored to provide the optimal level of effectiveness in treatment of the IL-13 related disorder. As will be appreciated by one of skill in the art, the use of the antibody in the preparation or manufacture of a medicament can involve any of the disclosed antibodies in any amount, sufficient to treat the particular condition it is directed to. Any of the herein disclosed conditions, or any IL-13 related disorders, can be the condition to be treated. In some embodiments, the use of the antibody in the preparation of a medicament is with one of the particular antibodies, such as mAb 731, 643, or 623, or any of the antibodies listed in Table 1. In some embodiments, the antibody used has a $K_D$ of less than 50 or 10 pM. In some embodiments, the antibody used results in a decrease in mucus production of at least 30%. As will be appreciated by one of skill in the art, the presently disclosed methods of use can be employed to create a medicament for the use. In some embodiments, the medicament further comprises an antibody or biomarker detector, to a biomarker. In other aspects, the biomarker detector is used in the production of a medicament without the antibody to IL-13. The biomarker detector in the medicament can be an antibody or other protein that specifically binds to the biomarker.

As will be appreciated by one of skill in the art, the nature of the disorder can play a role in the amount, frequency, and method of administration. For example, in chronic disorders, relatively larger amounts, more potent antibodies, and/or more frequently administered doses of the antibody may be required. Similarly, in acute disorders, the amount of antibody required for treatment, including prophylaxis, can be relatively less. In subjects in which sensitization is initially required prior to the challenge, lower amounts of the antibody can be beneficial compared to the amount required for subjects that are naturally allergic. In such chronic systems, increased amounts of the antibody, as well as increased frequency of administration can be advantageous. The exact amount can readily be determined by one of skill in the art, in light of the present disclosure. One of skill in the art will further appreciate other factors and how to adjust the administration of the antibody accordingly.

If desired, the isotype of an anti-IL-13 antibody can be switched, for example to take advantage of a biological property of a different isotype. For example, in some circumstances it may be desirable for the therapeutic antibodies against IL-13 to be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

By way of example, the anti-IL-13 antibodies discussed herein are human antibodies. If an antibody possessed desired binding to IL-13, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Biologically active antibodies that bind IL-13 are preferably used in a sterile pharmaceutical preparation or formulation to reduce the activity of IL-13. Anti-IL-13 antibodies preferably possess adequate affinity to potently suppress IL-13 activity to within the target therapeutic range. The suppression preferably results from the ability of the antibody to interfere with the binding of IL-13 to a signaling receptor, such as IL-13Ra1 (also known as, IL-13 R$\alpha$1, R$\alpha$1, IL-13R alpha 1, IL-13 receptor alpha 1, or other similar terms). In other embodiments the antibody may suppress IL-13 activity by interfering with the ability of IL-13 to signal through the receptor, even if it is able to bind. For example, the antibody may prevent interaction of the IL-13Ra1 with a co-receptor that is necessary for signaling, such as the IL-4 receptor alpha chain. In some embodiments the antibody is able to prevent IL-13 activity through a signaling receptor while allowing for IL-13 binding to a decoy receptor, such as IL-13Ra2. In this case, binding to the decoy receptor may allow clearance of the bound IL-13 and enhance the ability of the antibody to suppress IL-13 activity.

When used for in vivo administration, the antibody formulation is preferably sterile. This is readily accomplished by any method know in the art, for example by filtration through sterile filtration membranes. The antibody ordinarily will be stored in lyophilized form or in solution. Sterile filtration may be performed prior to or following lyophilization and reconstitution.

Therapeutic antibody compositions generally are placed into a container having a sterile access port, for example, an intravenous solution bag or vial having an adapter that allows retrieval of the formulation, such as a stopper pierceable by a hypodermic injection needle.

The modality of antibody administration is in accord with known methods, e.g., injection or infusion by subcutaneous, intravenous, intraperitoneal, intracerebral, intradermic, intramuscular, intraocular, intraarterial, intrathecal, or intralesional routes, or by inhalation or by sustained release systems as noted below. In some situations the antibody is preferably administered by infusion or by bolus injection. In other situations a therapeutic composition comprising the antibody can be administered through the nose or lung, preferably as a liquid or powder aerosol (lyophilized). The composition may also be administered intravenously, parenterally or subcutaneously as desired. When administered systemically, the therapeutic composition should be sterile, pyrogen-free and in a parenterally acceptable solution having due regard for pH, isotonicity, and stability. These conditions are known to those skilled in the art.

Antibodies for therapeutic use, as described herein, are typically prepared with suitable carriers, excipients, and other agents that are incorporated into formulations to provide improved transfer, delivery, tolerance, and the like. Briefly, dosage formulations of the antibodies described herein are prepared for storage or administration by mixing the antibody having the desired degree of purity with one or more physiologically acceptable carriers, excipients, or stabilizers. These formulations may include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, carbowax (polyethylene glycols of various molecular weights), semi-solid gels, and semi-solid mixtures containing carbowax. The formulation may include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Other acceptable carriers, excipients and stabilizers are well known to those of skill in the art. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J. Pharm. Sci.* 89(8):967-78 (2000), Powell et al. "Compendium of excipients for parenteral formulations" *PDA J. Pharm. Sci. Technol.* 52:238-311 (1998) and the citations therein for additional information.

Sterile compositions for injection can be formulated according to conventional pharmaceutical practice as described in *Remington: The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The antibodies can also be administered in and released over time from sustained-release preparations. Suitable examples of sustained-release preparations include semipermeable matrices of solid hydrophobic polymers containing the polypeptide. The matrices may be in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544, 545; and EP 102,324.

The dosage of the antibody formulation for a given patient may be determined by the attending physician. In determining the appropriate dosage the physician may take into consideration various factors known to modify the action of therapeutics, including, for example, severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays.

It is expected that the antibodies described herein will have therapeutic effect in treatment of symptoms and conditions resulting from or related to the activity of IL-13.

One way that the actual dose administered (or used in a kit) can be determined or verified is through the identification and use of IL-13 dependent biomarkers. Such biomakers are outlined in the Examples below and FIGS. 23-28, as are methods of identifying the biomarkers and their use. Examples of relevant biomarkers include C10, eotaxin, and TARC. Generally, to identify a biomarker, one can measure the quantity of the candidate biomarker in a subject that has a healthy and/or IL-13 disordered state (e.g., OVA-induced asthma), and compare the level of the biomarker in the subject to the level of the biomarker when one of the effective antibodies is administered to the subject (e.g., mAb 623, 731, etc.). As the administration of the antibody can block the activity of IL-13, the level of the candidate biomarker should also decline (assuming it is an actual biomarker) due to the administration of the antibody to the subject.

The biomarker, and/or a method of testing for it, can be used in a variety of ways. For example, the level of the biomarker in a subject can be followed throughout the treatment of a subject with an antibody, or other therapeutic method or composition with a similar effect, to allow one to track the effectiveness of the treatment. One can determine the amount of the biomarker present in the subject initially and determine any change upon the addition of the antibody. If the level of the biomarker does not change upon the initial administration of the antibody, additional antibody can be applied to the subject, applied more frequently, or by an alternative route. One of skill in the art will appreciate that the level of the biomarker can be determined in a variety of ways and should not unduly limit the technique. Any technique that can determine the amount of a protein (or mRNA, etc.) can be used, e.g., ELISA, or Biacore™ techniques. Additionally, in some embodiments, multiple biomarkers can be followed simultaneously. This can allow for more certainty about the IL-13 related aspect being monitored.

Of course, in some embodiments, the biomarkers are simply used to follow the progression of a disorder, without the additional variable of monitoring the treatment.

Additionally, the level of the biomarker in a subject can be used to determine if the subject has an IL-13 related disorder. Subjects with biomarker levels that are significantly above or below a standard level or range for a healthy individual(s) could be considered to suffer from an IL-13 related disorder.

The biomarker, or a method of testing for it, can be included in a kit for the treatment of an IL-13 related disorder.

As will be appreciated by one of skill in the art, while the present disclosure extensively discusses conditions or disorders involving excessive amounts of IL-13, the compositions and methods could also be applied to situations in which the effective level of IL-13 is too low. For example, the antibodies do not have to prevent the binding of IL-13 to its normal receptor and can instead prevent IL-13 binding to its decoy receptor, thereby effectively increasing the amount of IL-13 available in the system. However, in many embodiments, the antibodies will at least prevent IL-13 from binding to it signaling receptor.

Design and Generation of Other Therapeutics

In accordance with the present invention and based on the activity of the antibodies that are produced and characterized herein with respect to IL-13, advanced antibody therapeutics may be employed to treat specific diseases. These advanced therapeutics may include bispecific antibodies, immunotoxins, radiolabeled therapeutics, peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, bispecific antibodies can be generated that comprise (i) two antibodies, one with a specificity to IL-13 and another to a second molecule, that are conjugated together, (ii) a single antibody that has one chain specific to IL-13 and a second chain specific to a second molecule, or (iii) a single chain antibody that has specificity to both IL-13 and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer* (*Suppl.*) 7:51-52 (1992). In each case, the second specificity can be made as desired. For example, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)).

In some embodiments, an article of manufacture is provided comprising a container, comprising a composition containing an anti-IL-13 antibody, and a package insert or label indicating that the composition can be used to treat disease mediated by IL-13. Preferably a mammal and, more preferably, a human, receives the anti-IL-13 antibody. In preferred embodiments, the disease to be treated is selected from the group consisting of asthma, including both allergic (atopic) and non-allergic (non-atopic), bronchial asthma, chronic bronchitis, emphysema, chronic obstructive pulmonary disease (COPD), hay fever, rhinitis, urticaria, angioedema, allergic dermatitis, including contact dermatitis, Stevens-Johnson syndrome, anaphylatctic shock, food allergies, keratitis, conjunctivitis, steroid-resistant nephritic syndrome, mastocytosis, fibrotic disease such as lung fibrosis, including idiopathic pulmonary fibrosis, cystic fibrosis, bleomycin-induced fibrosis, hepatic fibrosis and systemic sclerosis, cancers, such as Hodgkin's disease, B-cell proliferative disorders such as B-cell lymphoma, particularly mediastinal large B-cell lymphoma, B-cell leukemias, ovarian carcinoma, diseases characterized by non-malignant B-cell proliferation such as systemic lupus erythematosus, rheumatoid arthritis, chronic active hepatitis and crioglobulnimias, high levels of autoantibodies, such as hemolytic anemia, thrombocytopenia, phospholipids syndrome and pemphigus, inflammatory bowel disease and graft-versus-host disease.

In some embodiments an anti-IL-13 antibody is used to treat asthma. In a particular embodiment the antibody is the 623 antibody or variants thereof described herein. In another particular embodiment the antibody is the 731 antibody or variants thereof described herein. Specific examples of how these antibodies can be used to treat asthma and other disorders are described below in the examples.

EXAMPLES

The following examples, including the experiments conducted and results achieved are provided for illustrative purposes only and are not to be construed as limiting upon the teachings herein.

Example 1

Antibody Generation

IL-13 and IL-13 Antigen Preparation

The following IL-13 peptides were used in the experiments described below.

Recombinant Human IL-13 (R & D 213-IL-005;
SEQ ID NO: 61):
GPVPPSTALRELIEELVNITQNQKAPLCNGSMVWSINLTAGMYCAALESL
INVSGCSAIEKTQRMLSGFCPHKVSAGQFSSLHVRDTKIEVAQFVKDLLL
HLKKLFREGQFN Recombinant Human IL-13 (Peprotech 200-13;
SEQ ID NO: 62):
SPGPVPPSTALRELIEELVNITQNQKAPLCNGSMVWSINLTAGMYCAALE
SLINVSGCSAIEKTQRMLSGFCPHKVSAGQFSSLHVRDTKIEVAQFVKDL
LLHLKKLFREGRFN Recombinant Human IL-13 (Peprotech 200-13A;
SEQ ID NO: 63):
MSPGPVPPSTALRELIEELVNITQNQKAPLCNGSMVWSINLTAGMYCAAL
ESLINVSGCSAIEKTQRMLSGFCPHKVSAGQFSSLHVRDTKIEVAQFVKD
LLLHLKKLFREGQFN -continued

```
Human IL-13-human Fc fusion protein (with leader
sequence; SEQ ID NO: 64):
MALLLTTVIALTCLGGFASPGPVPPSTALRELIEELVNITQNQKAPLCNG
SMVWSINLTAGMYCAALESLINVSGCSAIEKTQRMLSGFCPHKVSAGQFS
SLHVRDTKIEVAQFVKDLLLHLKKLFREGRFNEPKSCDKTHTCPPCPAPE
LLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALH
NHYTQKSLSLSPGK Human IL-13-rabbit Fc fusion protein (with leader
sequence; SEQ ID NO: 65):
MALLLTTVIALTCLGGFASPGPVPPSTALRELIEELVNITQNQKAPLCNG
SMVWSINLTAGMYCAALESLINVSGCSAIEKTQRMLSGFCPHKVSAGQFS
SLHVRDTKIEVAQFVKDLLLHLKKLFREGRFNRYLDKTVAPSTCSKPTCP
PPELLGGPSVFIFPPKPKDTLMISRTPEVTCVVVDVSQDDPEVQFTWYIN
NEQVRTARPPLREQQFNSTIRVVSTLPIAHQDWLRGKEFKCKVHNKALPA
PIEKTISKARGQPLEPKVYTMGPPREELSSRSVSLTCMINGFYPSDISVE
WEKNGKAEDNYKTTPAVLDSDGSYFLYNKLSVPTSEWQRGDVFTCSVMHE
ALHNHYTQKSISRSPGK Human IL-13-Mouse IL-13 Helix A (underlined;
SEQ ID NO: 66):
MHPLLNPLLLALGLMALLLTTVIALTCLGGFASPGPVPRSVSLPLTLKEL
IEELVNITQNQKAPLCNGSMVWSINLTAGMYCAALESLINVSGCSAIEKT
QRMLSGFCPHKVSAGQFSSLHVRDTKIEVAQFVKDLLLHLKKLFREGQFN Human IL-13-Mouse IL-13 Helix B (underlined;
SEQ ID NO: 67):
MHPLLNPLLLALGLMALLLTTVIALTCLGGFASPGPVPPSTALRELIEEL
VNITQNQKAPLCNGSMVWSINLTAGGFCVALDSLTNVSGCSAIEKTQRML
SGFCPHKVSAGQFSSLHVRDTKIEVAQFVKDLLLHLKKLFREGQFN Human IL-13-Mouse IL-13 Helix C (underlined;
SEQ ID NO: 68):
MHPLLNPLLLALGLMALLLTTVIALTCLGGFASPGPVPPSTALRELIEEL
VNITQNQKAPLCNGSMVWSINLTAGMYCAALESLINVSGCSAIYRTQRIL
HGLCPHKVSAGQFSSLHVRDTKIEVAQFVKDLLLHLKKLFREGQFN Human IL-13-Mouse IL-13 Helix D (underlined;
SEQ ID NO: 69):
MHPLLNPLLLALGLMALLLTTVIALTCLGGFASPGPVPPSTALRELIEEL
VNITQNQKAPLCNGSMVWSINLTAGMYCAALESLINVSGCSAIEKTQRML
SGFCPHKVSAGQFSSLHVRDTKIEVAHFITKLLSYTKQLFRHGQQFN
```

As will be appreciated by one of skill in the art, only a subset of the above residues may actually be involved in the formation of an epitope. For example, in SEQ ID NOs: 66-69 above, the epitopes may actually be the helix portion of each peptide (the underlined section). In one embodiment, the antibodies described herein are directed to any of the IL-13 epitopes or fragments thereof, including the helix portion of each peptide.

Immunization of Animals

Monoclonal antibodies against IL-13 were developed by immunizing XenoMouse® mice (XenoMouse® XMG2L3 and XenoMouse® XMG2, Abgenix, Inc. Fremont, Calif.). The human IL-13-human Fc fusion protein (SEQ ID NO: 64) or human IL-13-rabbit Fc fusion protein (SEQ ID NO: 65) was used as the immunogen for antibody generation. Each mouse was immunized via the footpad route of administration. The animals were immunized on days 0, 4, 7, 11, 14, 18, 21 and 25. The initial immunization was with 10 ug of antigen in CpG/Alum per mouse. Subsequent boosts were with 5 ug of antigen in CpG/Alum per mouse. The final boost on day 25 was with 5 ug of antigen in PBS without adjuvant per mouse. The animals were bled on day 20 to obtain sera for determination of titer as described below.

Titer Analysis

Titer was determined using a standard protocol. Briefly, Costar 3368 plates were coated with either IL-13 rabbit Fc fusion protein (SEQ ID NO: 65) or full length rabbit antibody overnight at 4° C. The plates were washed using Titertek Program ADG9, dried, and blocked with 250 μl 1% no fat skim milk/1×PBS. Following blocking, the plates were washed again using Titertek Program ADGP and dried. The sera to be tested was titrated vertically 1:2 in duplicate from a 1:100 initial dilution. The samples were run in 1% non fat skim milk/1×PBS at 50 ul/well and incubated for 1 h at room temperature.

After washing using Titertek Program ADG9 and drying, the plates were incubated for 1 hour at room temperature with a secondary rabbit anti-human Fc antibody conjugated to POD (1:8000 dilution; 50 μL/well) with minimal cross-reactivity to rabbit Fc in 1% no fat skim milk/1×PBS. Plates were then washed a final time using Titertek Program ADG9 and dried. POD substrate one-step TMB solution (50 μl/well) was added and allowed to develop for 30 minutes at room temperature. The reaction was stopped with 1 N HCL (50 μ/well) and the optical density was read immediately with a Titertek Plate reader.

Three animals with high titers for the IL-13 immunogen, as shown in Table 2, were selected for harvest.

TABLE 2

| Mouse | Coating | |
|---|---|---|
|  | IL-13 Rb Fc | RbIgG |
| 1 | 3855 | <100 |
| 2 | 5444 | <100 |
| 3 | >6400 | 268 |
| naive | <100 | <100 |

Primary Screen

The hyperimmune animals were harvested and CD19+ B-cells were isolated for subsequent B cell culture. The cells were induced to proliferate and terminally differentiate into plasma cells. Supernatants from these plasma cells were screened by ELISA to identify primary wells containing anti-IL-13-specific antibodies. The cultures were commonly run with 50 to 500 CD19+ B cells per well to allow the identification of monoclonal antigen-specific B cell cultures.

Briefly, IL-13-RbFc was coated onto Costar 3368 96 well plates at 1 ug/mL overnight. Each plate was washed 5 times with dH$_2$O and 40 μL of 1% milk in PBS were added to the plate. Subsequently, 10 μL of B cell supernatant was added to each well. After an hour at room temperature, the plates were again washed 5 times with dH$_2$O. To each well was added 50 μL of Rabbit anti-Human Fc-HRP with minimum anti-rabbit cross-reactivity (Jackson Laboratories; 1:8000 dilution). After 1 hour at room temperature, the plates were again washed 5 times with dH$_2$O and 50 μL of TMB substrate (Neogen) were added to each well. The reaction was stopped after 30 minutes by the addition of 50 μL of 1 N hydrochloric acid to each well and the plates were read at wavelength 450 nm.

Representative data resulting from the primary screen is shown below in Table 3. Positive wells were identified as those that were found to have a signal at least three times that of a control well. A total of 968 positive antigen-specific B cell wells were identified in the primary screen. All of these wells were taken forward for screening in a functional assay, as described below.

TABLE 3

| Plate | Well | Primary O.D. |
|---|---|---|
| 2357 | G11 | 2.598 |
| 2361 | G5 | 3.218 |
| 2372 | B8 | 2.308 |
| 2383 | H5 | 3.05 |
| 2398 | C5 | 2.203 |
| 2401 | G12 | 3.566 |
| 2413 | G11 | 3.347 |
| 2384 | G12 | 4.057 |
| 2388 | A10 | 4.219 |
| 2407 | G11 | 3.448 |

IL-13-Induced Eotaxin Production Assay

All of the 968 ELISA positive wells were screened twice in an IL-13-induced Eotaxin-1 release assay. The assay was performed such that only wells containing a high concentration of antibodies or wells containing high affinity antibody were identified as neutralizing. A total of 78 neutralizing antibodies were identified as neutralizing in this assay. The specific data from several wells of interest are also shown for illustrative purposes in Table 4.

For the assay, half of the area of 96-well assay plates was seeded with 4000 HDFa cells/well in 50 µL of Medium 106 supplemented with low serum growth supplement (Cascade). The plates were then incubated overnight at 37° C. in 5% $CO_2$ In a separate plate, 12.5 µL sample antibody, negative control or positive control was aliquoted into sterile 96-well assay plates. Approximately 600 µM of IL-13 was prepared in Medium 106 (4× final concentration) and approximately 100 ng/mL TNF-alpha was prepared in Medium 106 (2× final concentration).

To begin the assay, 12.5 µL of IL-13 or media alone was added to each well and allowed to incubate 37° C. in 5% $CO_2$ for 1 hr. Following the 1 hr incubation, the media of the HDFa cell was carefully removed using a multichannel pipette. 25 µL of TNF-alpha was added to each well. 25 µL sample/IL-13 was transferred to HDFa/TNF-alpha wells and cells were incubated at 37° C. in 5% $CO_2$ for 48 hrs.

Following 48 hrs of incubation, supernatant from HFDa assay wells was collected into 96-well VEE bottom plate. Samples were centrifuged at 1500 rpm for 5 min.

30 µL of sample was assayed for Eotaxin-1 release in an assay kit (R&D systems) according to standard protocol with the following modifications. (1) 50 µL Capture Ab was coated at 2 µg/mL; (2) 50 µL sample or standard was used (30 µL sample+20 µL media for a final volume of 50 µL); (3) 50 µL of detection Ab was used at 0.1 µg/mL; (4) 50 µL Streptavidin-HRP was used at 0.5 µg/mL; and (5) 50 µL Substrate Solution was used.

High Antigen (HA) Analysis of Anti-IL-13 Specific B Cell Culture Wells

Using an ELISA method, supernatants for concentration of antigen specific antibody were normalized. Using an anti-target (IL-13) antibody of known concentration titrated in parallel, a standard curve was generated and the amount of antigen specific antibody in the supernatant was compared to the standard and its concentration determined, see Table 5 below.

TABLE 5

| Plate | Well | ELISA OD determined at different antibody dilutions | | | | Ab Concentration (ng/ml) Based on an anti-IL-13 Standard Curve |
|---|---|---|---|---|---|---|
| 2357 | G11 | 3.944 | 1.769 | 0.708 | 0.424 | 386 |
| 2361 | G5 | 4.483 | 2.345 | 0.794 | 0.438 | 532 |
| 2372 | B8 | 3.209 | 1.238 | 0.552 | 0.373 | 240 |
| 2383 | H5 | 4.389 | 2.361 | 0.768 | 0.438 | 523 |
| 2398 | C5 | 2.057 | 0.752 | 0.383 | 0.324 | 114 |
| 2401 | G12 | 4.312 | 2.285 | 0.796 | 0.441 | 521 |
| 2413 | G11 | 3.977 | 1.783 | 0.648 | 0.415 | 360 |
| 2384 | G12 | 4.639 | 3.132 | 1.072 | 0.528 | 856 |
| 2388 | A10 | 4.689 | 3.23 | 1.261 | 0.612 | 1049 |
| 2407 | G11 | 4.891 | 2.9 | 1.072 | 0.537 | 824 |

The amount of antigen-specific antibody in each well was quantitated and plotted against the neutralization data for that well to identify the highest potency wells (FIG. 1). The wells containing the highest potency antibodies are those with the best inhibition with the lowest concentration of antibody (upper left quadrant of the graph).

Limited Antigen (LA) Analysis of Anti-IL-13 Specific B Cell Culture Wells

The limited antigen analysis is a method that affinity ranks the antigen-specific antibodies prepared in B-cell culture supernatants relative to all other antigen-specific antibodies. In the presence of a very low coating of antigen, only the highest affinity antibodies should be able to bind to any detectable level at equilibrium. (See, e.g., PCT Publication WO03/048730A2, incorporated herein by reference).

Here, biotinylated IL-13 was bound to streptavidin plates at four concentrations (250 ng/mL; 125 ng/mL; 62 ng/mL; and 31 ng/mL) for 1 hour at room temperature on 96-well culture plates. Each plate was washed 5 times with $dH_2O$ and 45 µL of 1% milk in PBS with 0.05% sodium azide was added to the plate. This was followed by the addition of 5 µL of B cell supernatant to each well. After 18 hours at room temperature on a shaker, the plates were again washed 5 times with $dH_2O$. To each well was added 50 µL of Gt anti-Human

TABLE 4

| Plate | Well | ELISA O.D. | Eotaxin Concentration (pg/mL) | % Inhibition | ELISA O.D. | Eotaxin Concentration (pg/mL) | % Inhibition |
|---|---|---|---|---|---|---|---|
| 2357 | G11 | 0.429 | 25 | 79 | 0.283 | 13 | 80 |
| 2361 | G05 | 0.393 | 19 | 85 | 0.295 | 15 | 76 |
| 2372 | B08 | 0.532 | 41 | 72 | 0.282 | 13 | 80 |
| 2383 | H05 | 0.42 | 23 | 84 | 0.247 | 6 | 90 |
| 2398 | C05 | 0.34 | 11 | 90 | 0.228 | 3 | 96 |
| 2401 | G12 | 0.564 | 46 | 70 | 0.384 | 31 | 57 |
| 2413 | G11 | 0.401 | 20 | 84 | 0.283 | 13 | 82 |
| 2384 | G12 | 0.517 | 38 | 73 | 0.297 | 15 | 76 |
| 2388 | A10 | 0.459 | 29 | 78 | 0.274 | 11 | 82 |
| 2407 | G11 | 0.469 | 31 | 78 | 0.278 | 12 | 84 |

(Fc)-HRP at 1 μg/mL. After 1 hour at room temperature, the plates were again washed 5 times with dH$_2$O and 50 μL of TMB substrate were added to each well. The reaction was stopped by the addition of 50 μL of 1M phosphoric acid to each well and the plates were read at wavelength 450 nm.

Figure 2:
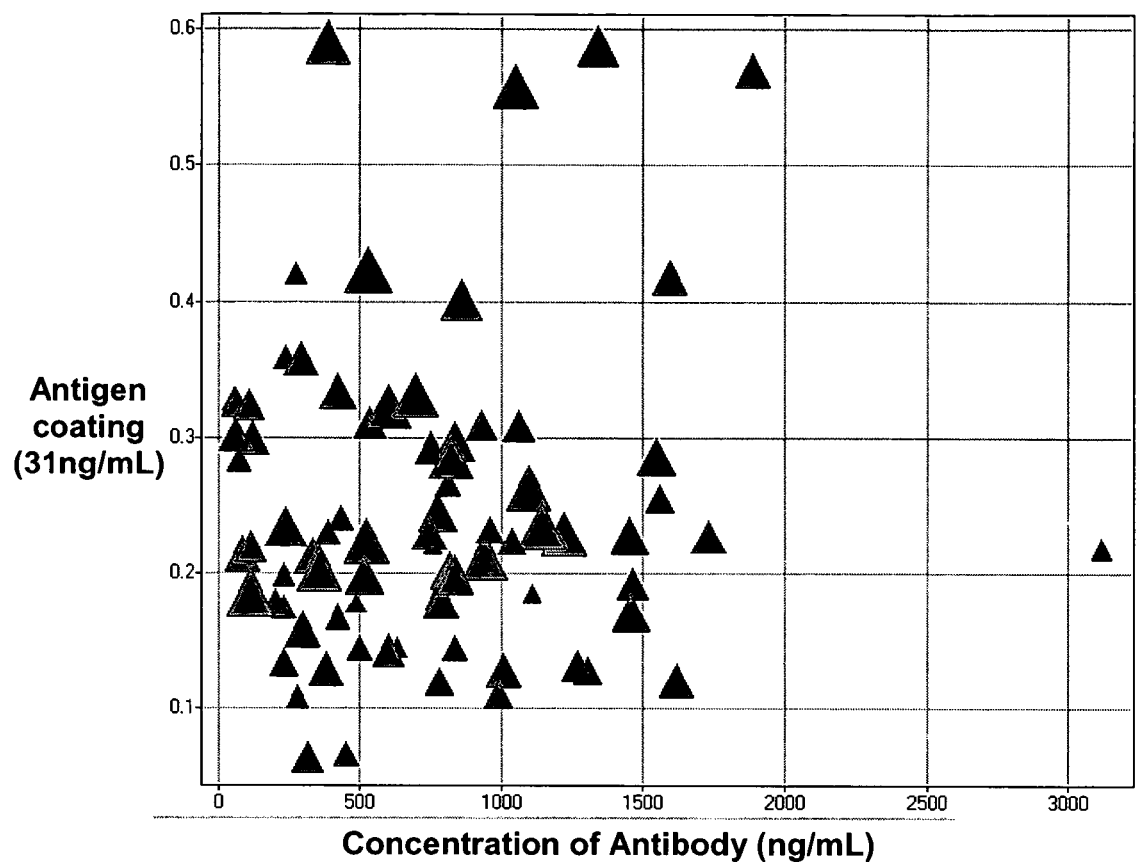
FIG. 2 is a plot depicting the relationship of ELISA OD of each antibody versus antibody concentration at an antigen coating of 31 ng/mL.

However, a number of wells including 2388A10 and 2357G11 were clearly superior as measured by OD at the lowest antigen coating, as illustrated in FIG. 2. The results presented in FIG. 2 demonstrate the ability of the different antibodies to bind at low concentration of antigen coating. The antibodies giving the highest OD signals have the highest affinity under the conditions of this assay. The remaining clones were further analyzed by combining the high antigen data which measures specific antibody concentration and the limited antigen output. In this way it was possible to compare the affinity of antibodies at different concentrations in B-cell culture supernatants. The wells containing the highest affinity antibodies are those with the highest ELISA OD in the context of lowest concentration of Ag-specific antibody.

Based on all of the screening data, the wells listed in Table 6 were identified for further analysis (plaque assay and micromanipulation, single cell PCR and recombinant expression). Five wells were selected based on potency (inhibition/total specific Ab): 2372B8, 2398 C5, 2401G12 and 2413G11. Three wells were selected based on affinity and inhibition: 2357G11, 2361G5 and 2384G12, and two wells were selected based on neutralization data alone: 2388A10 and 2407G11.

TABLE 6

| | | ELISA OD determined at different antigen coatings | | | |
|---|---|---|---|---|---|
| Plate | Well | 250 ng/ml | 125 ng/ml | 62 ng/ml | 31 ng/ml |
| 2357 | G11 | 2.582 | 1.553 | 1.066 | 0.59 |
| 2361 | G5 | 2.582 | 1.505 | 1.075 | 0.423 |
| 2372 | B8 | 1.616 | 0.79 | 0.506 | 0.234 |
| 2383 | H5 | 1.533 | 0.817 | 0.459 | 0.224 |
| 2398 | C5 | 1.187 | 0.694 | 0.425 | 0.186 |
| 2401 | G12 | 1.295 | 0.827 | 0.407 | 0.198 |
| 2413 | G11 | 1.274 | 0.783 | 0.449 | 0.203 |
| 2384 | G12 | 2.056 | 1.161 | 0.759 | 0.401 |
| 2388 | A10 | 2.637 | 1.76 | 1.152 | 0.558 |
| 2407 | G11 | 1.627 | 0.887 | 0.583 | 0.285 |

IL-13-Specific Hemolytic Plaque Assay

Cells secreting IL-13-specific antibodies of interest were isolated utilizing an IL-13 specific hemolytic plaque assay generally as described in Babcook et al. (*Proc. Natl. Acad. Sci. USA*, 93:7843-7848 (1996), incorporated herein by reference). The cells that were isolated are identified in Table 7 below.

Biotinylation of Sheep Red Blood Cells (SRBC)

SRBC were stored in RPMI media as a 25% stock. A 250 μl SRBC packed-cell pellet was obtained by aliquoting 1.0 ml of the stock into an eppendorf tube, spinning down the cells (pulse spin at 8000 rpm (6800 rcf) in microfuge) and removing the supernatant. The cells were then washed twice with 1 ml of PBS pH 8.6. The cell pellet was then re-suspended in 4.75 ml PBS at pH 8.6 in a 15 ml tube. In a separate 50 ml tube, 2.5 mg of Sulfo-NHS biotin was added to 45 ml of PBS at pH 8.6. Once the biotin had completely dissolved, the 5 ml of SRBCs were added and the tube rotated at RT for 1 hour. The SRBCs were centrifuged at 3000 g for 5 min, the supernatant drawn off and the SRBCs resuspended in 1 ml PBS at pH 7.4 in an Eppendorf tube. SRBCs were washed 3 times with 1 ml PBS at pH 7.4. The SRBCs were then resuspended in 4.75 ml immune cell media (RPMI 1640 with 10% FCS) in a 15 ml tube (5% B-SRBC stock). Stock was stored at 4° C. until needed.

Streptavidin (SA) Coating of B-SRBC

One ml of the 5% B-SRBC stock was transferred into to a fresh eppendorf tube. The B-SRBCs were pelleted, the supernatant drawn off, the pellet re-suspended in 1.0 ml PBS at pH 7.4, and the centrifugation repeated. The wash cycle was repeated 2 times, and then the B-SRBC pellet was resuspended in 1.0 ml of PBS at pH 7.4 to give a final concentration of 5% (v/v). 10 μL of a 10 mg/ml streptavidin (CalBiochem, San Diego, Calif.) stock solution was added and the tube mixed and rotated at RT for 20 min. The washing steps were repeated and the SA-SRBC were re-suspended in 1 ml PBS pH 7.4 (5% (v/v)).

Human IL-13 Coating of SA-SRBC

The SA-SRBC were coated with photobiotinylated-Human IL-13-RbFc fusion at 100 ug/ml, then mixed and rotated at RT for 20 min. The SRBC were washed twice with 1.0 ml of PBS at pH 7.4 as above. The IL-13-coated SRBC were re-suspended in RPMI (+10% FCS) to a final concentration of 5% (v/v).

Determination of the Quality of IL-13-SRBC by Immunofluorescence (IF)

Approximately 10 μl of 5% SA-SRBC and 10 μl of 5% IL-13-coated SRBC were each added to separate fresh 1.5 ml eppendorf tube containing 40 μl of PBS. A control human anti-IL-13 antibody was added to each sample of SRBCs at 45 μg/ml. The tubes were rotated at RT for 20 min, and the cells were then washed three times with 100 ul of PBS. The cells were re-suspended in 50 μl of PBS and incubated with 20 μg/mL Gt-anti Human IgG Fc antibody conjugated to Alexa488 (Molecular Probes, Eugene, Oreg.). The tubes were rotated at RT for 20 min, and then washed with 100 μl PBS and the cells re-suspended in 10 μl PBS. 10 μl of the stained cells were spotted onto a clean glass microscope slide, covered with a glass cover slip, observed under fluorescent light, and scored on an arbitrary scale of 0-4.

Preparation of Plasma Cells

The contents of a single B cell culture well previously identified by the various assays described above as containing a B cell clone secreting the immunoglobulin of interest were harvested. Using a 100-1000 μL pipetteman, the contents of the well were recovered by adding 37C RPMI (+10% FCS). The cells were re-suspended by pipetting and then transferred to a fresh 1.5 ml Eppendorf tube (final vol. approx 700-1000 μl). The cells were centrifuged in a microfuge at 2500 rpm for 1 minute at room temperature. The tube was then rotated 180 degrees and spun again for 1 minute at 2500 rpm. The freeze media was drawn off and the immune cells resuspended in 100 μL RPMI (10% FCS), then centrifuged. This washing with RPMI (+10% FCS) was repeated and the cells re-suspended in 75 μL RPMI (+10% FCS) and stored on ice until ready to use.

Plaque Assay

To a 75 μL sample of cells was added 75 uL each of IL-13-coated SRBC (5% (v/v) stock, diluted as necessary if the SRBC lawn was too thick), 4× guinea pig complement (Sigma, Oakville, ON) stock prepared in RPMI (+10% FCS), and 4× enhancing sera stock (1:900 in RPMI (+10% FCS)). The mixture (3-5 μL) was spotted onto TC plate lids (BD Biosciences, San Jose, Calif.) and the spots covered with undiluted paraffin oil. The slides were incubated at 37° C. for a minimum of 1 hour.

TABLE 7

| Plate | Well | Single Cell (SC) Numbers |
|---|---|---|
| 2407 | G11 | SC-IL-13-557-576 |
| 2388 | A10 | SC-IL-13-577-596 |
| 2401 | G12 | SC-IL-13-597-616 |
| 2372 | B8 | SC-IL-13-617-636 |
| 2413 | G11 | SC-IL-13-637-657 |
| 2398 | C5 | SC-IL-13-658-670 |
| 2383 | H5 | SC-IL-13-671-690 |
| 2384 | G12 | SC-IL-13-691-710 |
| 2357 | G11 | SC-IL-13-711-730 |
| 2361 | G5 | SC-IL-13-731-750 |

Cloning and Expression

After isolation of the single plasma cells, mRNA was extracted and reverse transcriptase PCR was conducted to generate cDNA encoding the variable heavy and light chains of the antibody secreted by each cell. The human variable heavy chain region was cloned into an IgG2 expression vector. This vector was generated by cloning the constant domain of human IgG2 into the multiple cloning site of pcDNA3.1+/Hygro (Invitrogen, Burlington, ON). The human variable light chain region was cloned into an IgK or IgL expression vector. These vectors were generated by cloning the constant domain of human IgK or human IgL into the multiple cloning site of pcDNA3.1+/Neo (Invitrogen, Burlington, ON).

The heavy chain and the light chain expression vectors were then co-transfected using lipofectamine into a 60 mm dish of 70% confluent human embryonal kidney (HEK) 293 cells. The transfected cells secreted a recombinant antibody with the identical specificity as the original plasma cell for 24-72 hours. 3 mL of supernatant was harvested from the HEK 293 cells and the secretion of an intact antibody was demonstrated with a sandwich ELISA to specifically detect human IgG. Specificity was confirmed through binding of the recombinant antibody to IL-13 using ELISA.

The secretion ELISA tests were performed as follows. Control plates were coated with 2 mg/mL goat anti-human IgG H+L overnight as for binding plates, IL-13 was coated onto Costar Labcoat Universal Binding Polystyrene 96 well plates and held overnight at 4° C. The plates were washed five times with dH$_2$O. Recombinant antibodies were titrated 1:2 for 7 wells from the undiluted lipofection supernatant. The plates were washed five times with dH$_2$O. A goat anti-human IgG Fc-specific HRP-conjugated antibody was added at a final concentration of 1 μg/mL for 1 hour at RT for the secretion and the two binding assays. The plates were washed five times with dH$_2$O. The plates were developed with the addition of TMB for 30 minutes and the ELISA was stopped by the addition of 1 M phosphoric acid. Each ELISA plate was analyzed to determine the optical density of each well at 450 nm.

Purification of Recombinant Anti-IL-13 Antibodies

For larger scale production, heavy and light chain expression vectors (2.5 μg of each chain/dish) were lipofected into HEK293 cells in ten 100 mm dishes that were 70% confluent. The transfected cells were incubated at 37° C. for 4 days, at which time the supernatant (6 mL) was harvested and replaced with 6 mL of fresh media. At day 7, the supernatant was removed and pooled with the initial harvest (120 mL total from 10 plates).

Each antibody was purified from the supernatant using Protein-A Sepharose (Amersham Biosciences, Piscataway, N.J.) affinity chromatography (1 mL). The antibodies were eluted from the Protein-A column with 500 mL of 0.1 M Glycine (pH 2.5). The eluates were dialyzed in PBS (pH 7.4) and filter sterilized. The antibodies were analyzed by non-reducing SDS-PAGE to assess purity and yield. Concentration was also measured by UV analysis at OD 280.

Example 2

Recombinant Antibody Characterization

Figure 3:
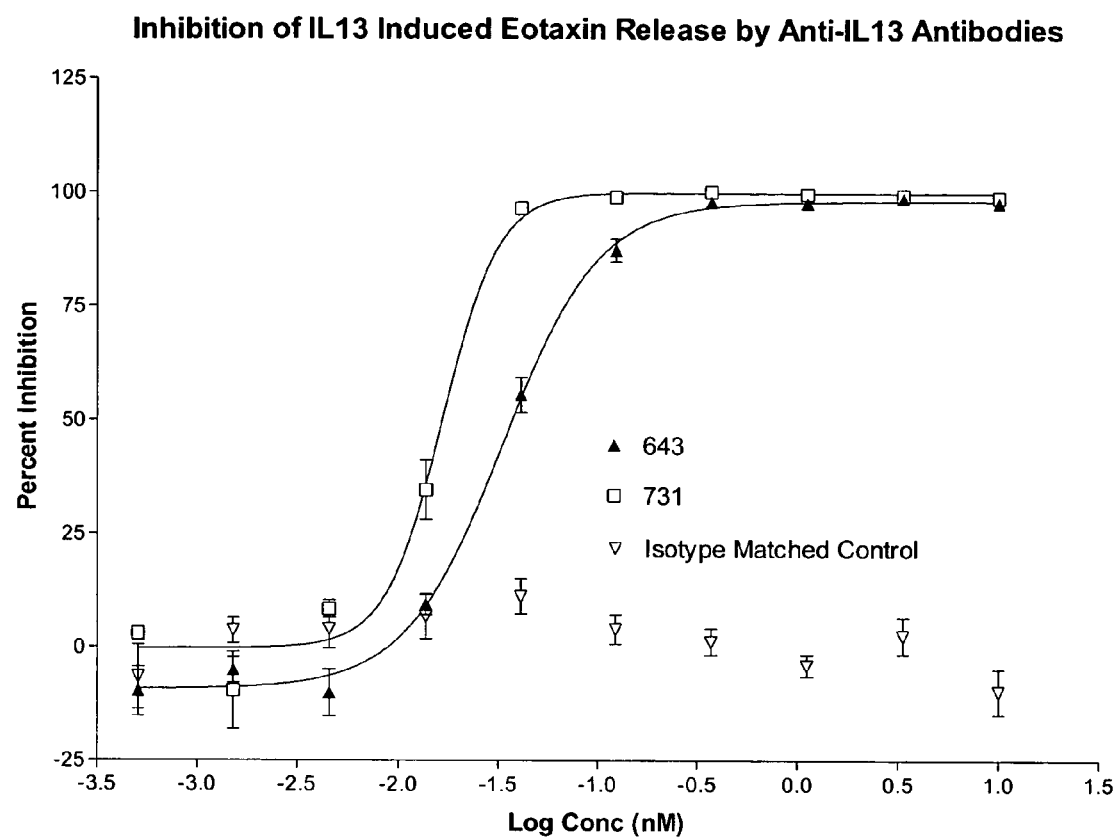
FIG. 3 is a graph showing the percent inhibition of IL-13 induced eotaxin release by recombinant antibodies 643 and 731 compared to an isotype matched control.

Recombinant antibodies were analyzed for potency in the eotaxin assay as described above. The results are presented in Table 8 below. Also included are the measured IC$_{50}$'s in this assay for murine IL-13 receptor α2/FC and human IL-13 receptor α2/Fc. FIG. 3 shows the percent inhibition of IL-13 induced eotaxin release by recombinant antibodies 643 and 731 compared to an isotype matched control, e.g., an irrelevant IgG2 monoclonal antibody.

TABLE 8

| | IC50 (pM) | | | | |
|---|---|---|---|---|---|
| mAb ID | n = 1 | n = 2 | n = 3 | Average | Standard Dev |
| 731 | 11 | 19 | 17 | 16 | 4 |
| 713 | 21 | 21 | 19 | 21 | 1 |
| mIL-13Ralpha2/Fc | 29 | 39 | 29 | 32 | 6 |
| 643 | 44 | 28 | 33 | 35 | 8 |
| 623 | 31 | 40 | 35 | 36 | 4 |
| 693 | 38 | 69 | 53 | 54 | 16 |
| 602 | 80 | 53 | ND | 66 | NA |
| 353 | 99 | 123 | 80 | 101 | 22 |
| hIL-13Ralpha2/Fc | 128 | 147 | 119 | 131 | 14 |
| 785 | 223 | 144 | 160 | 176 | 42 |
| 11.18.3 | 213 | 304 | 217 | 245 | 51 |
| 157 | 260 | 207 | 306 | 258 | 50 |
| 176 | 233 | ND | ND | 233 | NA |
| 183 | 1040 | 1842 | ND | 1441 | NA |
| 264 | 293 | 313 | 284 | 297 | 15 |
| 243 | 253 | ND | ND | 253 | NA |
| 356 | 1087 | 913 | ND | 1000 | NA |

BiaCore Affinity

Affinity to human IL-13 (R&D) was investigated by BiaCore assay for six of the antibodies (602, 623, 643, 693rep1, 693rep2 and 7310). First, two high-density goat α-human antibody surfaces were prepared on a CM5 Biacore chip using routine amine coupling for the capture of the mAbs three at a time. All mAbs were diluted to ~5 μg/Ml using HBS-P running buffer containing 100 μg/ml BSA. Each purified mAb was captured for one minute on a different flow cell surface for every IL-13 injection cycle using a Biacore 2000 instrument.

IL-13 (R&D) was injected using the KINJECT command at concentrations of 100.9, 50.4, 25.2, 12.6, 6.30, 3.15, 1.58 and 0.788 nM for mAbs 693, 713 and 731 and 25.2, 12.6, 6.30, 3.15, 1.58, 0.788, and 0.394 nM for mAbs 602, 623, and 643, over all surfaces for 1.5 min., followed by a twenty minute dissociation. The IL-13 samples were prepared in HBS-P running buffer containing 100 μg/ml BSA. All samples were randomly injected in duplicate with several mAb capture/buffer KINJECT cycles interspersed for double referencing.

The high-density goat α-human antibody surfaces were regenerated with a 12-second pulse of 1/100 diluted concentrated phosphoric acid (146 mM, pH 1.5) after each cycle. mAb 693 was run twice because there was an extra flow cell available on the instrument during the last series of medium resolution experiments.

The data was fit to a 1:1 interaction model with a term for mass transport using CLAMP. The data for the six antibodies are shown in Table 9.

TABLE 9

| Antibody | $k_a$ (M$^{-1}$s$^{-1}$) | $k_d$ (s$^{-1}$) | $K_D$ (pM) |
|---|---|---|---|
| 602 | $3.0 \times 10^6$ | $5.1 \times 10^{-4}$ | 172 |
| 623 | $4.9 \times 10^6$ | $2.5 \times 10^{-4}$ | 52 |
| 643 | $4.4 \times 10^6$ | $2.9 \times 10^{-4}$ | 66 |
| 693 rep 1 | $2.0 \times 10^6$ | $3.8 \times 10^{-4}$ | 189 |
| 693 rep 2 | $2.5 \times 10^6$ | $2.7 \times 10^{-4}$ | 109 |
| 713 | $2.9 \times 10^6$ | $3.4 \times 10^{-5}$ | 12 |
| 731 | $3.9 \times 10^6$ | $3.5 \times 10^{-5}$ | 9 |

Kinetic Analysis

Kinetic measurements of several of the antibodies were evaluated using the KinExA® method. This method involves solution-based determination of formal affinity measurements at equilibrium.

One hundred μg of each mAb was coupled to CNBr-activated Sepharose 4B or Azlactone beads. The remaining active groups on the beads were blocked as recommended by the manufacturer. The beads were then blocked with 10 mg/ml BSA in 1 M Tris and stored in the blocking solution. For some experiments the mAb was directly absorption coated to PMMA beads as recommended by the manufacturer and blocked with 10 mg/ml BSA in PBS and stored in the blocking solution.

KinExA experiments were performed using an automated flow immunoassay system, KinExA 3000, in which beads coupled with the relevant mAbs served as the solid phase. Briefly, a constant amount of native human or macaque monkey IL-13 (10-650 pM), prepared by purifying and stimulating PBMCs according to standard protocols, was incubated with titrating concentrations of anti-h-IL-13 mAbs starting at 25 nM in sample buffer (PBS with 0.1% BSA to reduce nonspecific binding). Antigen/antibody complexes were incubated at RT for 48 hrs to 168 hrs to allow equilibrium to be reached. The mixture was drawn through the corresponding antibody-coupled beads to accumulate unbound antigen. The volumes and flow rates of the mixture were varied depending upon the specific signal obtained in each experiment.

The captured IL-13 was detected using solutions containing a secondary Ab (either a polyclonal anti-IL-13 Ab or a monoclonal Ab that binds to another epitope) and Cy5-conjugated anti-species Ig to the secondary antibody in sample buffer. In some cases the bead bound IL-13 was detected using a mixture of SA-Cy5 and a biotinylated antibody that binds to an epitope other than that bound by the bead immobilized Ab.

The concentrations, volumes, and flow rates of the secondary antibody solutions were varied to optimize the signal to noise ratio in each experiment. The bound signals were converted into relative values as a proportion of control in the absence of hIL-13. Three replicates of each sample were measured for all equilibrium experiments. The equilibrium dissociation constant ($K_D$) was obtained from nonlinear regression analysis of the data using a one-site homogeneous binding model contained within the KinExA software. The software calculates the $K_D$ and determines the 95% confidence interval by fitting the data points to a theoretical $K_D$ curve. The 95% confidence interval is given as $K_D$ low and $K_D$ high. The affinities are summarized in Tables 10 for native human IL-13 and 11 for native macaque IL-13.

TABLE 10

| Antibody | $K_D$ | $K_D$ low | $K_D$ high |
|---|---|---|---|
| 623 | 24 pM | 6.6 pM | 60 pM |
| 643 | 13 pM | 6.2 pM | 25 pM |
| 713 | 3.6 pM | 1.1 pM | 7.3 pM |
| 731 | 8.9 pM | 6.2 pM | 12 pM |

TABLE 11

| Antibody | $K_D$ | $K_D$ low | $K_D$ high |
|---|---|---|---|
| 623 | 37 pM | 18 pM | 64 pM |
| 731 | 1.6 nM | 880 pM | 2.2 nM |

The association rate constant was investigated using KinExA for two of the antibodies 623 and 731. The same IL-13 coupled beads were used as the probe and the "direct" "injection" methods were used. These methods are identical to the KinExA equilibrium assays with respect to antigen capture, antigen concentration and antigen detection. In the direct method, the antigen and antibody are mixed in advance and then run on the KinExA. In the injection method, the antibody and a titration of antigen are mixed together for a set time before reading. Briefly, hIL-13 was mixed with an amount of mAb that would bind approximately 80% of the antigen based on the equilibrium experiments. The free antigen present in the sample was probed repeatedly, pre-equilibrium. Since the binding signals are proportional to the concentration of free antigen in the solution, the signals decreased over time until the solution reached equilibrium. The volumes and flow rats of the antigen-mAb mixtures and the Cy5-labeled secondary antibody were varied depending upon the mAb tested. Data was analyzed utilizing the KinExA analysis software. This software graphically represents the decrease in binding signals over time, and fits the collected data points to an exact solution of the kinetic differential equations for binding. From this curve, an optimal solution for the $k_{on}$ was determined (Table 12). The $k_{off}$ was indirectly calculated from solutions for the $k_{on}$ and $K_D$.

TABLE 12

| Antibody | Method | KD (pM) | $k_{on}$ (M$^{-1}$·s$^{-1}$) | $k_{on}$ High | $k_{on}$ Low | $k_{off}$(s$^{-1}$) | % Error |
|---|---|---|---|---|---|---|---|
| 623 | Kinetic Direct | 24 | 1.1E+07 | 1.4E+07 | 5.1E+06 | 2.7E−04 | 1.37 |
| 623 | Kinetic inject | 24 | 1.5E+07 | 2.1E+07 | 1.1E+07 | 3.6E−04 | 5.46 |
| 731 | Kinetic inject | 8.9 | 4.7E+06 | 6.3E+06 | 3.4E+06 | 4.2E−05 | 4.96 |

Binding to the IL-13 Variant Protein

The ability of antibodies 623 and 731 to bind to an IL-13 variant protein in which the wildtype arginine 110 is replaced with glutamine (IL-13Q110R) was investigated.

Briefly, plates were coated in IL-13RbFc (50 µL of 2.5 µg/mL) by incubation in 1×PBS (pH7.4) and 0.05% azide overnight at 4° C. The plates were then washed with 1×PBS and blocked for 30 minutes with 100 µL of 1% no fat skim milk/1×PBS at room temperature.

IL-13 or IL-13Q110R was pre-incubated with anti-IL-13 antibodies for 1 hr at room temperature. Titrated IL-13 vertically from 2000 ng/ml with final volume of 30 µl/well. 30 µl of mAb was added per well at 40 ng/ml (sc731, 623) and 80 ng/ml (sc693), resulting in a final concentration of IL-13 at the first point in the titration of 1000 ng/ml, a final concentration of antibodies 623 and 731 at the first point in the titration of 20 ng/ml and final concentration of antibody 693 at the first point in the titration of 40 ng/ml.

After pre-incubation, 50 µl/well was transferred from the pre-incubation solution to a plate pre-coated with IL-13RbFc and incubated for 30 minutes at room temperature. Plates were washed and rabbit anti Hu IgG Fc HRP was added at a concentration of 200 ng/ml. Following a further 30 minutes incubation and subsequent wash, TMB was added and incubated for an additional 30 minutes. Reactions were stopped with 1N HCL and plates were read as soon as possible on a Powerwave X340 96 well microplate reader (Biotek).

Figure 4:
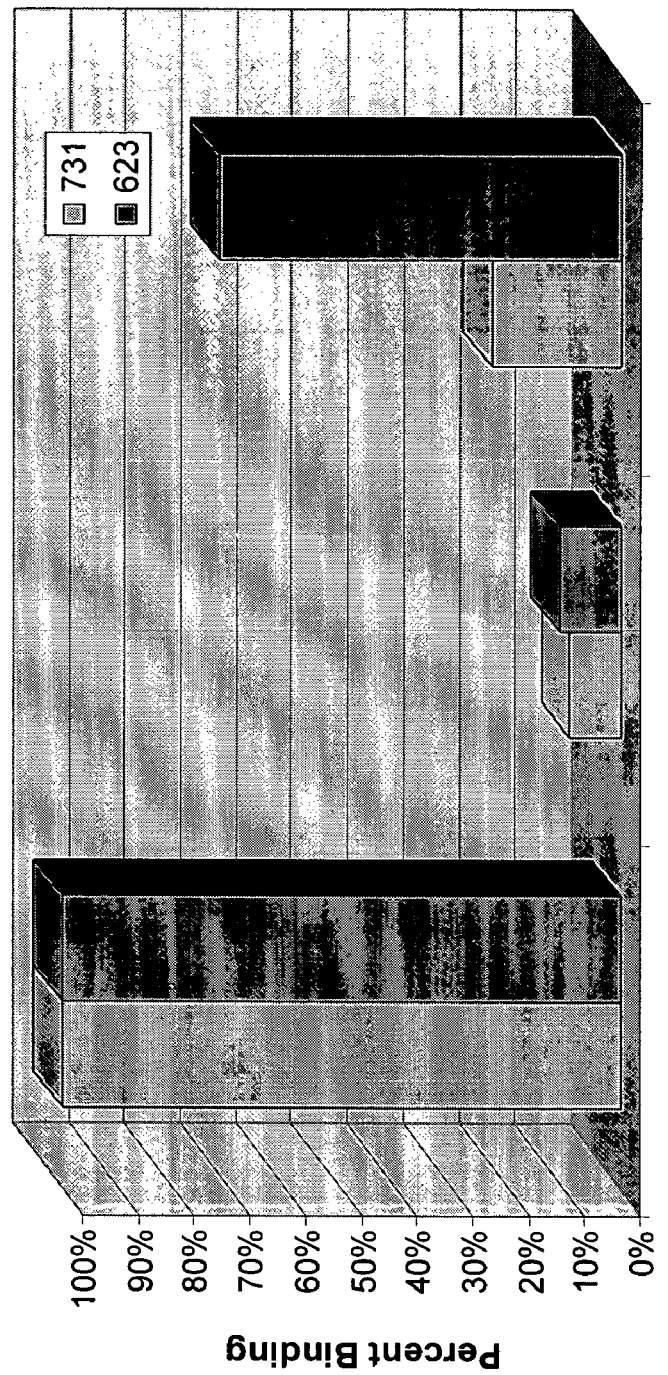
FIG. 4 is a bar graph comparing the ability of IL-13 or IL-13Q110R to inhibit binding of 731 or 623 to IL-13 coated ELISA plates.

As can be seen in FIG. 4, pre-incubation with IL-13 inhibited binding of both antibodies 623 and 731 to IL-13 coated ELISA plates, while pre-incubation with IL-13 variant IL-13Q110R inhibited binding of 731 to a much greater extent than binding of 623.

It is noted that antibodies to this particular variant can be particularly useful in treating certain diseases. For example, as noted in U.S. Pat. Pub. No. 2005/0065327, a number of genetic polymorphisms in the IL-13 gene have been linked to allergic disease. In particular, a variant of the IL-13 gene in which the arginine residue at amino acid 130 is substituted with glutamine (Q130R) has been associated with bronchial asthma, atopic dermatitis and raised serum IgE levels (See, e.g., Heinzmann, A., et al. Hum Mol Genet, 2000. 9(4): p. 549-59; Howard, T. D., et al. Am J Hum Genet, 2002. 70(1): p. 230-6; Kauppi, P., et al. Genomics, 2001. 77(1-2): p. 35-42; and Graves, P. E., et al. J Allergy Clin Immunol, 2000. 105(3): p. 506-13). This particular IL-13 variant is referred to herein as the Q110R variant (arginine residue at amino acid 110 is substituted with glutamine) because a 20 amino acid signal sequence has been removed from the amino acid count. Arima et al., (J Allergy Clin Immunol, 2002. 109(6): p. 980-7) report that this variant is associated with raised levels of IL-13 in serum. The IL-13 variant (Q110R) and antibodies to this variant are discussed in WO 01/62933. An IL-13 promoter polymorphism, which alters IL-13 production, has also been associated with allergic asthma (van der Pouw Kraan, T. C., et al. Genes Immun, 1999. 1(1): p. 61-5). It is believed that the variant induces an increase in the incidence of asthma through increasing the effective half-life of the IL-13 ligand. It is believed that IL-13Q110R can have a lower affinity for the decoy IL-13 receptor.

As will be appreciated by one of skill in the art, in light of the present disclosure, in some embodiments, the antibodies can bind to both IL-13 and an IL-13 variant with approximately equal affinities or $K_D$s. This can allow one to treat patients with both forms of IL-13 (wild-type and a variant) with a single antibody. Thus, in some embodiments, an antibody that can bind to IL-13 and an IL-13 variant with a same or similar $K_D$ can be useful. In some embodiments, there is less than a 20% difference in the $K_D$ of the fully human mAb for IL-13 and IL-13Q110R, for example, less than 20-15, 15-10, 10-8, 8-6, 6-4, 4-2, 2-1, 1-0 percent difference in the $K_D$s of the antibody. In some embodiments, the $K_D$s between the wild-type and IL-13Q110R variant differ by less than 1000 fold, 1000-100, 100-10, 10-1, or 1-0.2 fold. Similarities for other variants of IL-13 can also be used in selecting or using antibodies.

Receptor Chain Competition

The ability of anti-IL-13 antibodies to block IL-13 binding to the receptors IL-13Rα1 and IL-13Rα2 was investigated. Samples were analyzed using the flow cytometer. The results are presented in FIG. 5A and FIG. 5B. The data demonstrated the ability of Ab 643 (FIG. 5A) and of Ab 731 (FIG. 5B) or an isotype control antibody to bind to IL-13 and the receptors involved in the binding process. The particular receptor (e.g., IL-13Ra2, IL-13Ra1, or IL-4R) that was binding IL-13 and allowing the antibody to interact with the cells was determined using neutralizing antibodies against all possible IL-13 receptors expressed on HDFa cells. A summary of the various experiments and predicted results is displayed in FIG. 5C and FIG. 5D.

Briefly, HDFa cells were resuspended in FACS buffer to yield about 200 000 cells/well/100 µL and 100 µL of cells were aliquoted into 96-well VEE bottom plates. Neutralizing anti-receptor antibodies (anti human IL-13Ra1 (R&D Systems), anti human IL-13Ra2 (R&D Systems) or anti human IL-4R(R&D Systems)) were diluted in FACS buffer at twice the final concentration (10 µg/mL FINAL). Anti-IL-13 and Control Ab's were also diluted in FACS buffer at 2× final concentration (1 µg/mL), as was IL-13 (human R&D; 10 ng/mL FINAL).

A VEE bottom plate of HDFa cells was centrifuged at 180×g for 7 min and the supernatant removed by inversion (PLATE #1). Cells were resuspended in 50 µL FACS buffer and an additional 50 µL of anti human IL-13Ra1, anti human IL-13Ra2, anti human IL-4R or FACS buffer (No Receptor Ab Control) was added to appropriate wells. The cells and antibodies were then incubated on ICE for about 1.5 hrs.

A second VEE bottom plate was used for Ab/IL-13 pre-incubation (PLATE #2). 60 µL of the test antibody was aliquoted into a VEE bottom plate. 60 µL of IL-13 added to appropriate wells and the mixture was incubated on ice for about 1.5 hrs.

After the incubation HDFa cells were centrifuged at 180×g for 7 min and the supernatant was removed by inversion. The cells in PLATE #1 were resuspended in 100 µL FACS buffer or 100 µL of Ab/IL-13 and incubated for a further 1.5 hrs.

Following the second incubation the cells were centrifuged, washed 1× with FACS buffer and 100 µL of FACS buffer, 7AAD or 2 µg/mL goat anti Hu IgG-Fc-Cy5 was added to appropriate wells.

The cells and secondary antibody were incubated on ice for 20 minutes, followed by a wash with FACS buffer. Cells were then resuspended in 100 µL FACS buffer and aliquoted into pre-labeled FACS tubes containing 300 µL cold FACS buffer.

Figure 5A:
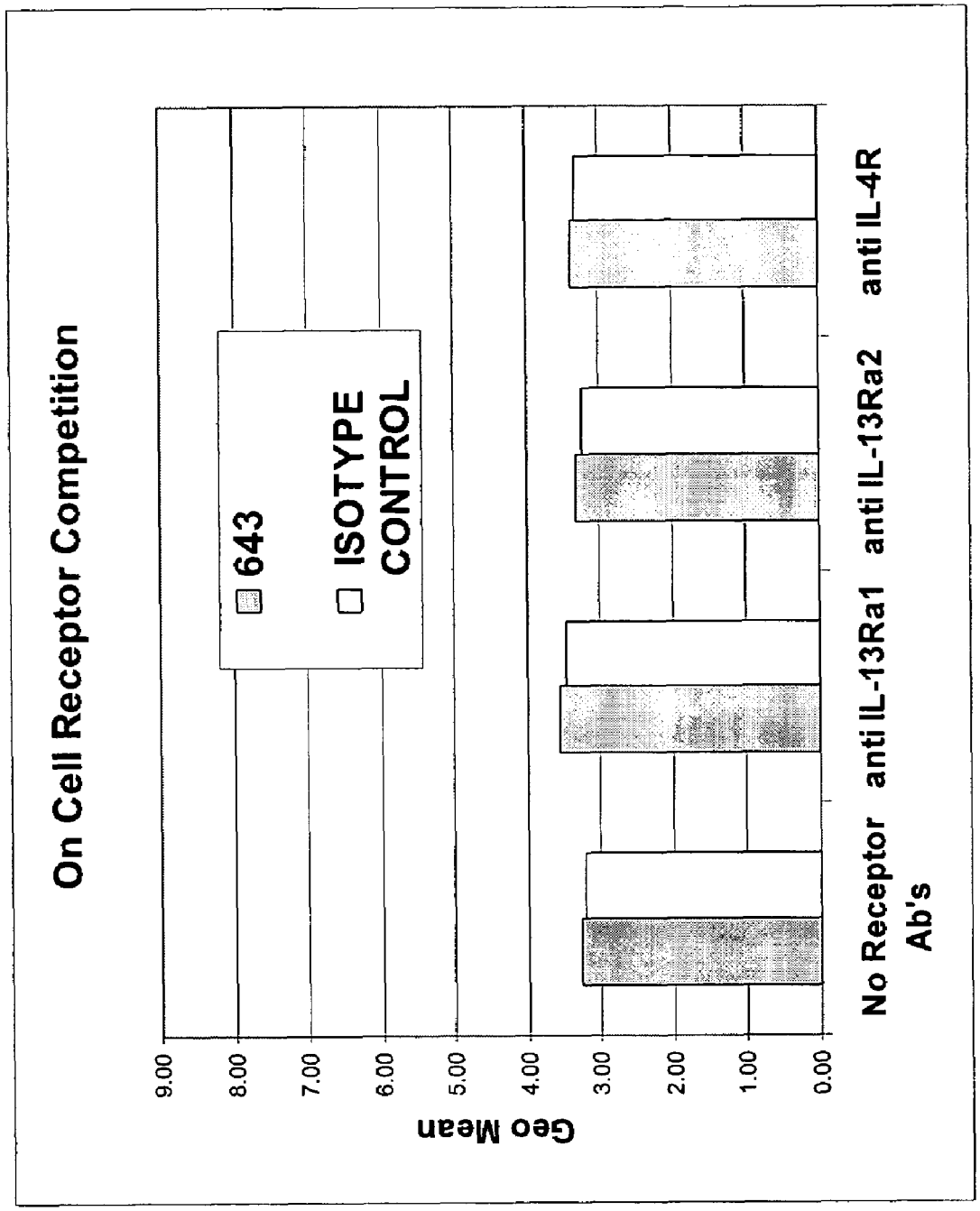
FIG. 5A is a bar graph comparing on cell receptor competition between antibody 643 and an isotype control.
Figure 5B:
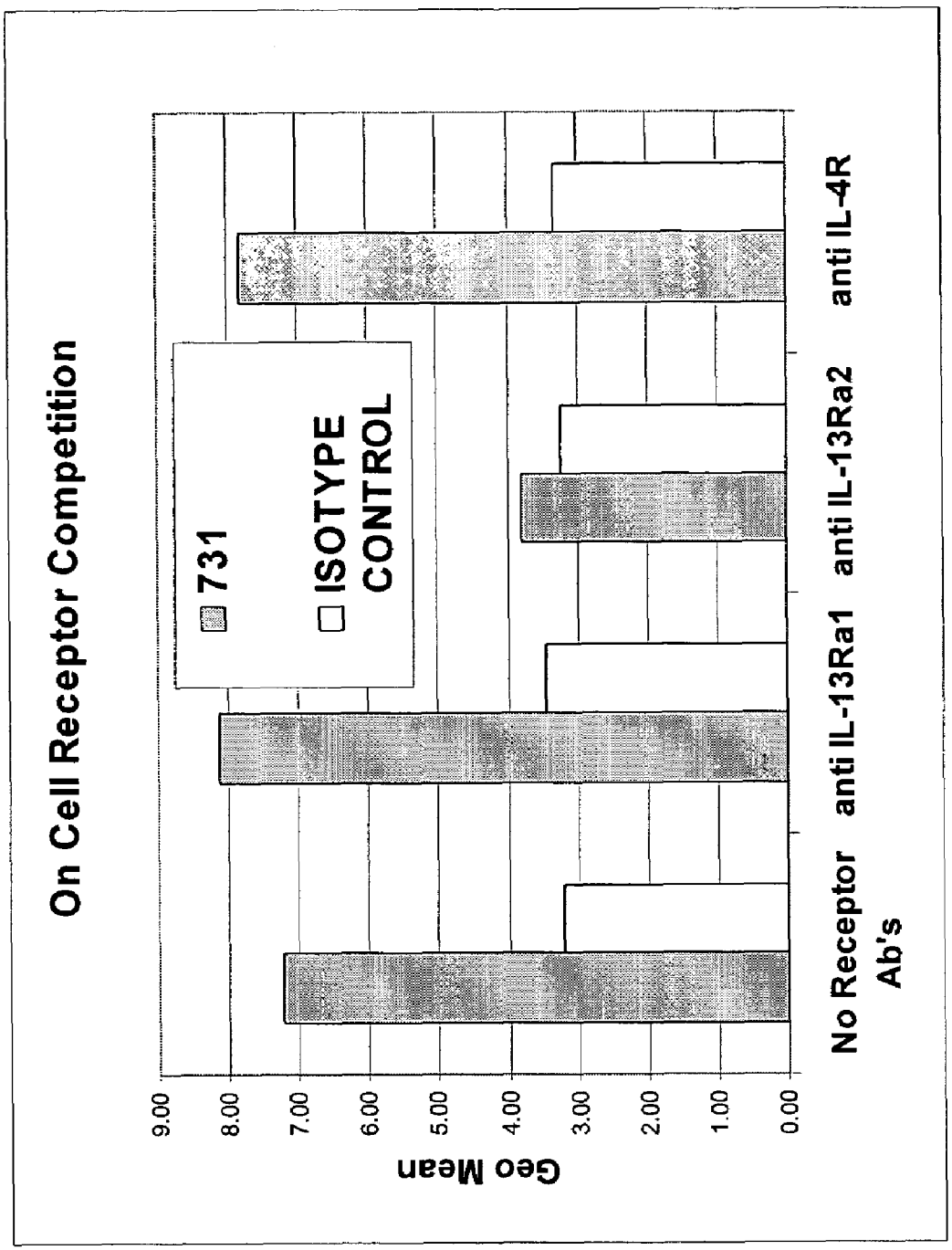
FIG. 5B is a bar graph comparing on cell receptor competition between antibody 731 and an isotype control.
Figure 5C:
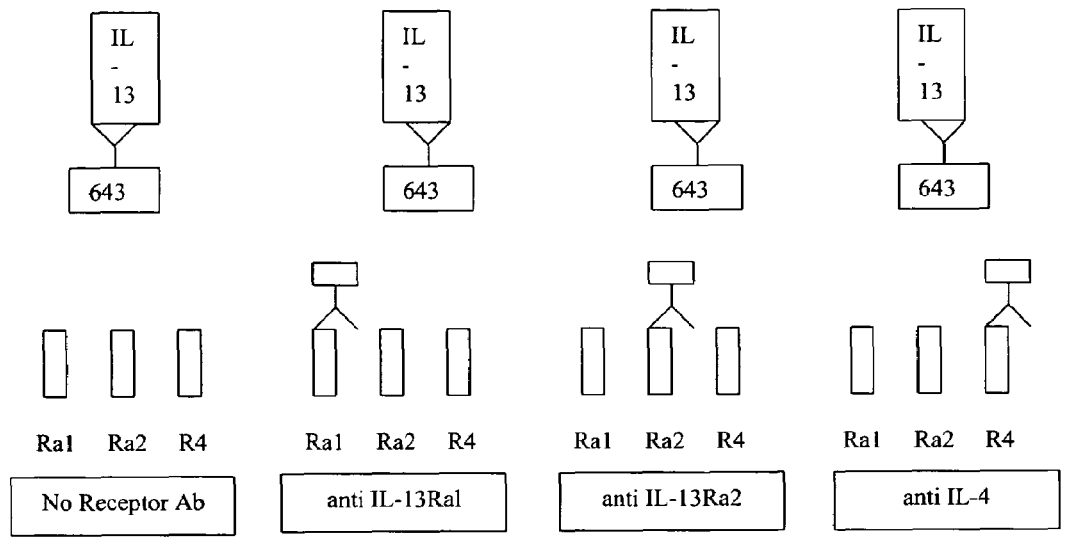
FIG. 5C is a cartoon depicting the protocol and various predicted results from FIG. 5A and FIG. 5E.
Figure 5D:
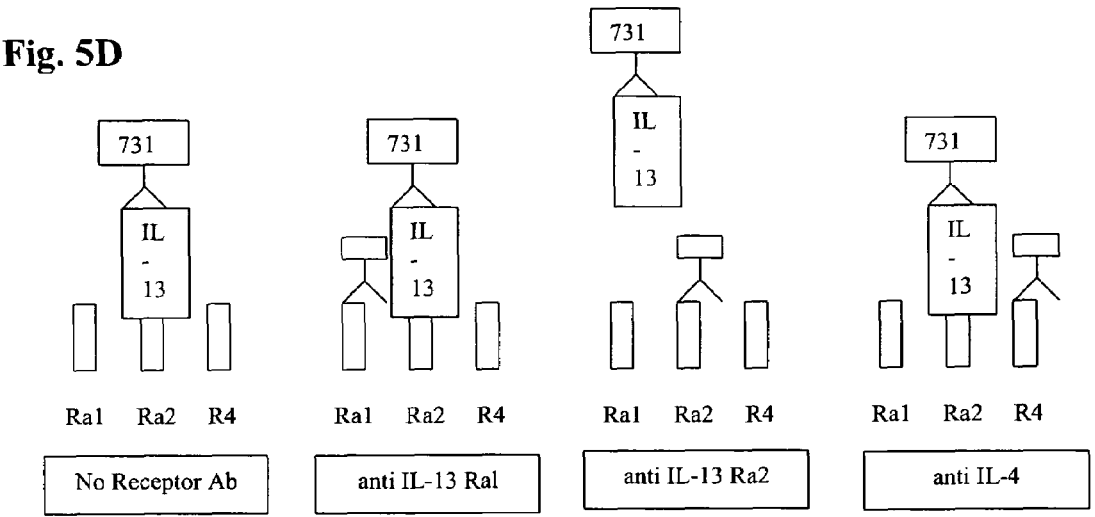
FIG. 5D is a cartoon depicting the protocol and various predicted results from FIG. 5B.

Samples were analyzed using the flow cytometer. The results are presented in FIG. 5A and FIG. 5B. A summary of the above protocol and predicted results for each of the antibodies is shown in FIG. 5C and FIG. 5D. As shown by FIG. 5A, IL-13 does not bind to HDFa cells in the presence of Ab 643. It appears that Ab 643 prevents IL-13 from binding to its receptors on HDFa cells, as shown in each of the panels of FIG. 5C. As can be seen in FIG. 5B, this is not the case for Ab 731. IL-13 allows Ab731 to bind to HDFa cells. This binding is not blocked by Abs against IL-13Ralpha1 or IL-4R but is blocked by antibodies against IL-13Ralpha2, indicating that Ab 731 prevents IL-13 from binding to IL-13Ralpha1 or IL-4R but not to IL-13Ralpha2, as displayed in FIG. 5D. Results for mAb 623, an antibody that is similar to mAb 643, are also presented below.

The amount of IL-13 Ra1, IL-13 Ra2 and IL-4R surface expression on HDFa cells was determined by FACS analysis using anti Receptor antibodies. HDFa cells prepared as described above were incubated with anti receptor antibodies at a concentration of 5 μg/ml on ice for 1 hr. Cells were washed with FACS buffer and incubated with Cy5 secondary (anti-hum) antibody at 2 μg/ml. on ice for 30 min. After washing, samples were analyzed by flow cytometry. The results are presented in Table 13 below.

TABLE 13

| Antibody Target | FACS Geometric Mean Average |
|---|---|
| IL13 Receptor Alpha 1 | 8.39 |
| IL13 Receptor Alpha 2 | 9.4 |
| IL4 Receptor Alpha 1 | 9.15 |
| Negative Control | 3.8 |

Figure 5E:
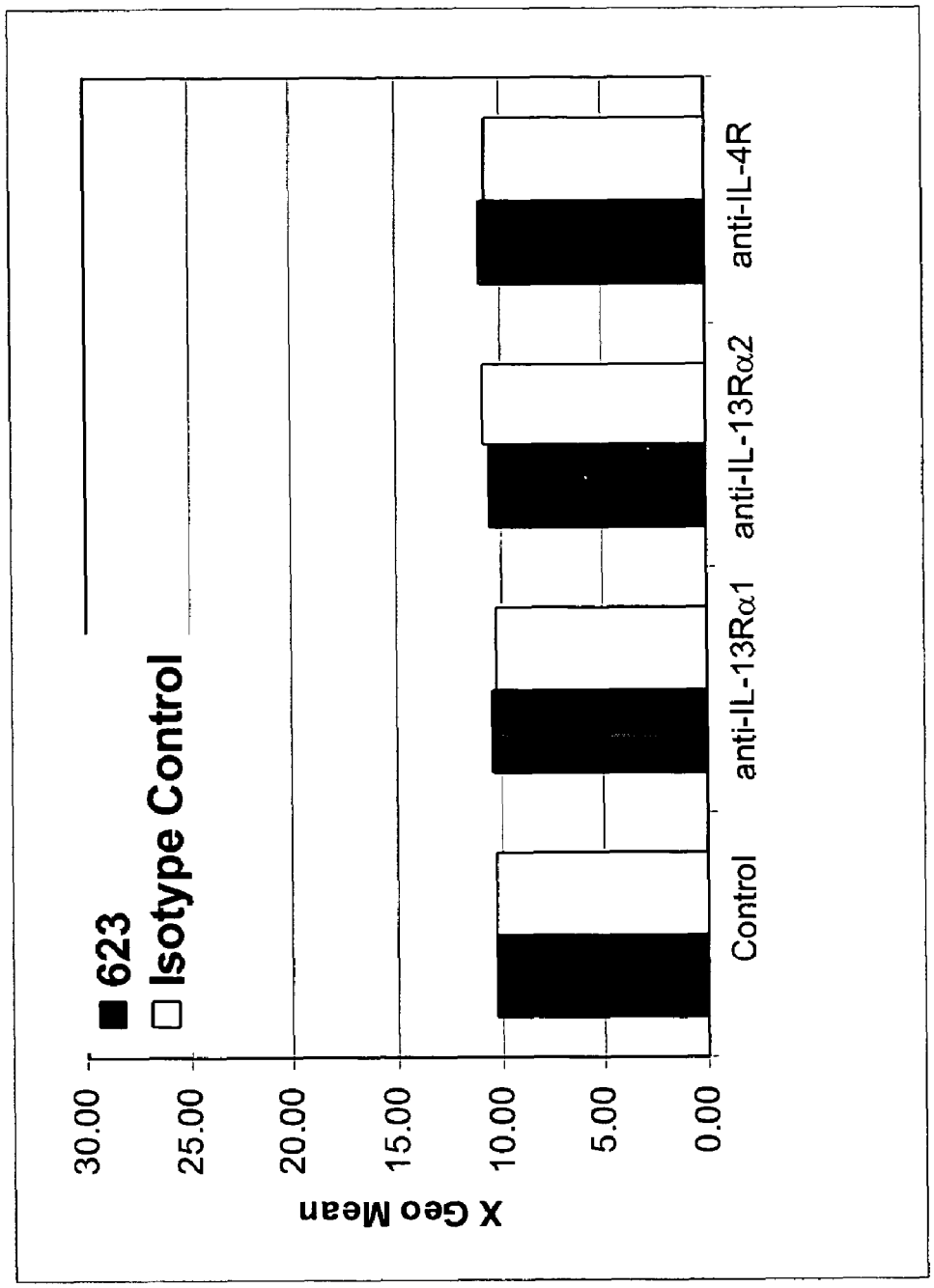
FIG. 5E is a bar graph comparing cell receptor competition between antibody 623 and an isotype control.

In addition to the above results for mAb 643 and mAb 731, a similar experiment was performed for mAb 623. The results are shown in FIG. 5E. The results for mAb 623 are similar to those for mAb 643, suggesting an interaction depicted in FIG. 5C, rather than that depicted for mAb 731 in FIG. 5D.

Epitope Mapping

The epitopes for the antibody-IL-13 complexes were analyzed by three methods, 1) SELDI, 2) Screening of Random peptide phage display libraries, and 3) expression of Chimeric Human/Mouse IL-13 molecules. These three techniques combined with knowledge of the structure of IL-13 produced a coherent view of the relative binding sites and antigenic regions of these mAbs. This has permitted the identification of functional epitopes, particularly for the regions involved in binding to the signaling receptor.

Figure 6A:
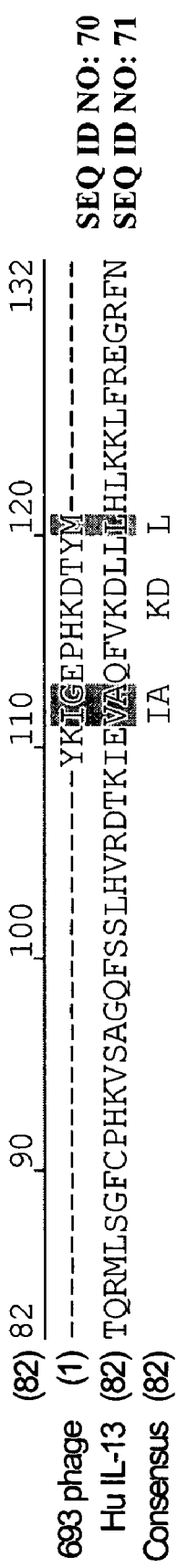
FIG. 6A shows the alignment of a phage-display derived peptide recognized by antibody 693 and part of IL-13 sequence.

As an initial examination, dot blot analysis of mAb binding to IL-13 purified protein revealed which antibodies bound to which form (linear or conformational) of the epitope. mAbs 693 and 785 bound to the reduced denatured antigen, the linear epitope. mAbs 602, 623, 643, and 713, bound to the non reduced (conformational epitope) IL-13 but not to the reduced denatured antigen. mAb 763 displayed no binding. Following this, the linear epitopes were mapped using random peptide phage display library. After two rounds of panning mAb 693 against a 12-mer random peptide library expressed on phage, a single specific binder was sequenced and aligned to residues 109-120 (Helix D) of IL-13. (FIG. 6A). IL-13 antibodies were grouped in 3 different bins, although bins do not always correlate with epitopes determined by other means. One antibody from each bin was picked for mapping by SELDI. Table 14 demonstrates the binning results of the IL-13 antibodies.

TABLE 14

| Mab | VH | VL | Bin |
|---|---|---|---|
| 353 | VH4-59/D2-21/JH3b | A30/JK3 | 1 |
| 713 | VH3-23/D6-19/JH6b | V2-1/JL1 | 1 |
| 731 | VH3-23/D6-19/JH6b | V2-1/JL1 | 1 |
| 602 | VH3-15/D1-26/JH6b | V2-7/JL3 | 2 |
| 623 | VH3-15/D1-26/JH6b | V2-7/JL3 | 2 |
| 643 | VH3-15/D1-26/JH6b | V2-7/JL3 | 2 |
| 693 | VH4-4/D5-5/JH6B | V2-14/JL2 | 3 |

Mapping of Epitopes Using SELDI

The antibody-antigen complex was digested with a high concentration of Lys-C and Asp-N. The epitope was then determined by SELDI and identified by the mass of the fragment. Table 15 displays the predicted masses for the peptides derived by digestion of IL-13 digested with endoproteinase Lys-C.

TABLE 15

| Mass | Position | Mis. Cut | IL-13 Peptide Sequence | SEQ ID NO: |
|---|---|---|---|---|
| 9442.7 | 21-108 | 3 | GPVPPSTALRELIEELVNIT QNQKAPLCNGSMVWSINLTA GMYCAALES LINVSGCSAIEKTQRMLSGFCPHKVSAGQFS SLHVRDTK | 73 |
| 7829.9 | 21-93 | 2 | GPVPPSTALRELIEELVNIT QNQKAPLCNGSMVWSINLTA GMYCAALESLINVSGCSAIE KTQRMLSGFCPHK | 74 |
| 7729.8 | 45-116 | 3 | APLCNGSMVWSINLTAGMYC AALESLINVSGCSAIEKTQR MLSGFCPHKVSAGQFSSLHV RDTKIEVAQFVK | 75 |
| 6815.3 | 45-108 | 2 | APLCNGSMVWSINLTAGMYC AALESLINVSGCSAIEKTQR MLSGFCPHKVSAGQFSSLHV RDTK | 76 |

The masses identified following cleavage were 6842.8 (for peptide fragment 45-108), 7733.7 (for peptide fragment 45-116), and 9461.4 (for peptide fragment 21-108). Thus, the binding site for mAb 713 was determined to be within residues 45-108 of IL-13.

Peptide Array for Mapping Conformational Epitopes

A peptide array of 101, 12-mer peptides, spanning residues 21-132 of the IL-13 sequence was generated (SIGMA-Genosys). Each consecutive peptide was offset by one amino acid from the previous one, yielding a nested, overlapping library. The array was probed with mAb 713 and binding of mAb 713 to the peptides was detected by incubating the PVDF membranes with HRP-conjugated secondary antibody followed by enhanced chemiluminescence. Two consecutive spots, corresponding to amino acids 70 to 80 of IL-13 and three consecutive spots, corresponding to amino acids 83 to 92 of IL-13 were observed. The array was also probed with mAb 731. One spot, corresponding to amino acids 70 to 80 of IL-13 was observed. A similar experiment was also performed to determine the epitope for mAb 623, and is described in Example 10 below. The results indicated that mAb 623 binds to residues 21-29.

Epitope Mapping Using Mouse IL-13 Chimeric Molecules

Figure 6B:
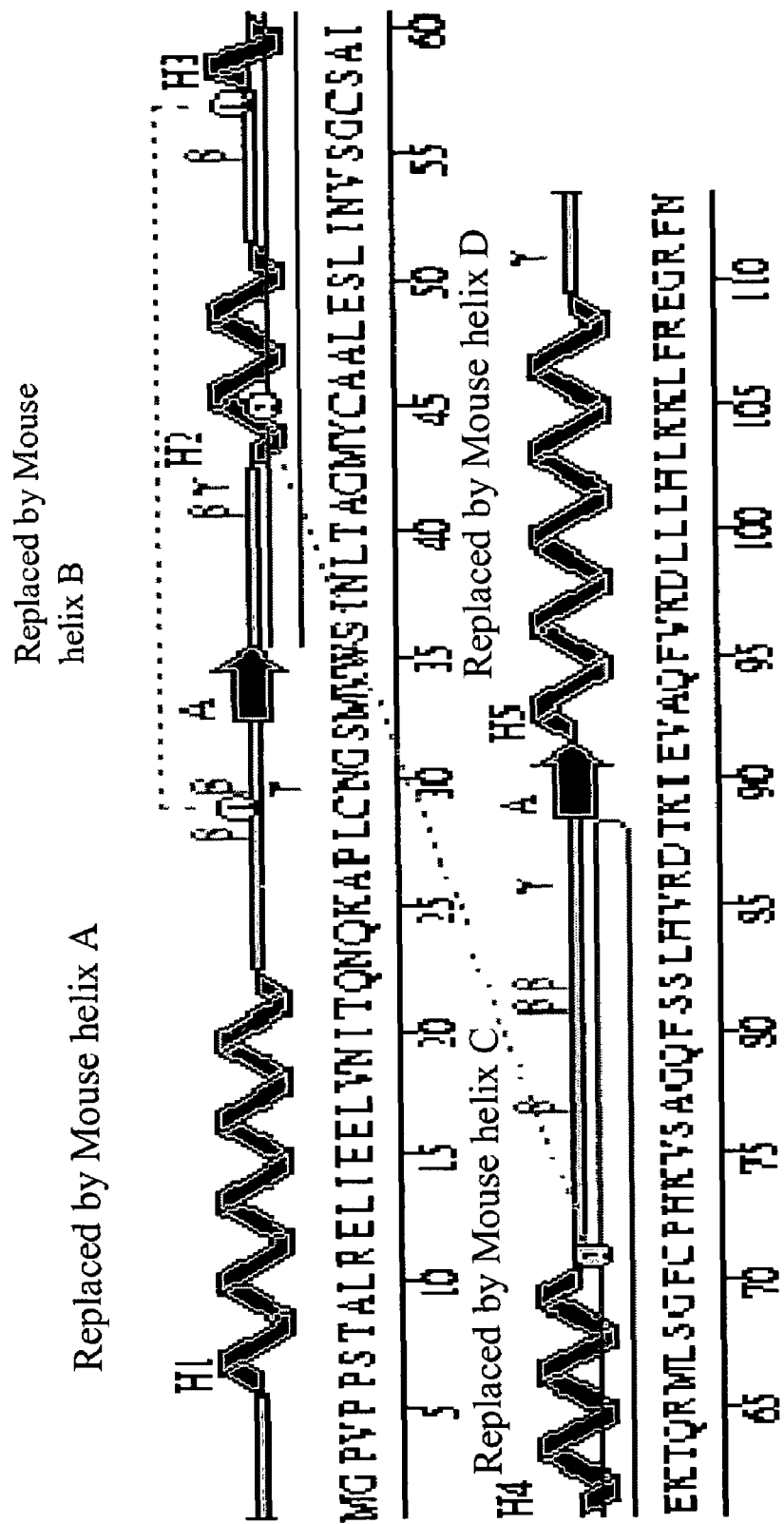
FIG. 6B is a chart showing the secondary structure of IL-13 (SEQ ID NO: 72) and indicates which regions of human IL-13 were replaced with mouse IL-13 for the construction of the chimeric proteins.

Mouse sequences of Helix A, Helix B, Helix C, and Helix D were shuffled with human sequences generating four new mouse chimeras. A representation of the location of the helices is shown in FIG. 6B. None of the mAbs bound to the mouse IL-13. The four chimeras are as follows:

```
                                          (SEQ ID NO: 77)
MHPLLNPLLLALGLMALLLTTVIALTCLGGFASPGPVPRSVSLPLTKEL
IEELVNITQNQKAPLCNGSMVWSINLTAGMYCAALESLINVSGCSAIEKT
QRMLSGFCPHKVSAGQFSSLHVRDTKIEVAQFVKDLLLHLKKLFREG
QFN;

(SEQ ID NO: 78)
MHPLLNPLLLALGLMALLLTTVIALTCLGGFASPGPVPPSTALRELIEEL
VNITQNQKAPLCNGSMVWSINLTAGGFCVALDSLTNVSGCSAIEKTQRML
SGFCPHKVSAGQFSSLHVRDTKIEVAQFVKDLLLHLKKLFREGQFN;

(SEQ ID NO: 79)
MHPLLNPLLLALGLMALLLTTVIALTCLGGFASPGPVPPSTALRELIEEL
VNITQNQKAPLCNGSMVWSINLTAGMYCAALESLINVSGCSAIYRTQRI
LHGLCPHKVSAGQFSSLHVRDTKIEVAQFVKDLLLHLKKLFREGQFN;

-continued
                                          (SEQ ID NO: 80)
MHPLLNPLLLALGLMALLLTTVIALTCLGGFASPGPVPPSTALRELIEEL
VNITQNQKAPLCNGSMVWSINLTAGMYCAALESLINVSGCSAIEKTQRML
SGFCPHKVSAGQFSSLHVRDTKIEVAHFITKLLSYTKQLFRHGQQFN.
```

The chimeras were then expressed and secreted IL-13 chimeric proteins were detected in an ELISA assay. The results are summarized in Table 16, the "*" denotes that the binding was weak in the sandwich ELISA.

TABLE 16

| mAb | Hu IL-13 | Mo HelixA | Mo HelixB | Mo HelixC | Mo HelixD | Epitope | Bin |
|---|---|---|---|---|---|---|---|
| 693 | Yes | Yes | Yes | Yes | No | HelixD | 3 |
| 785 | Yes | Yes | Yes | Yes | No | HelixD | |
| 713* | Yes | Yes | Yes | No | Yes | HelixC | 1 |
| 731* | Yes | Yes | Yes | No | Yes | HelixC | 1 |
| 602 | Yes | Yes | Yes | Yes | Yes | | 2 |
| 623 | Yes | Yes | Yes | Yes | Yes | | 2 |
| 643 | Yes | Yes | Yes | Yes | Yes | | 2 |

The results of the above three studies of the epitopes of IL-13 are summarized in Table 17.1.

TABLE 17.1

| mAb | Phage Display | SELDI | Spots | Chimera | Bin |
|---|---|---|---|---|---|
| 3.1.2.4 | 21-33 | | | HelixA | |
| 693 | 109-121 | | | HelixD | 3 |
| 785 | 111-128 | | | HelixD | |
| 713 | | 45-108 | 70-80 and 83-92 | HelixC | 1 |
| 731 | | | 70-80 | HelixC | 1 |
| 602 | | | | | 2 |
| 623 | | | 21-29 | | 2 |
| 643 | | | | | 2 |

Thus, it appears that a number of different possible epitope positions are used by the various antibodies disclosed herein.

Antibody Binning Analysis

Anti-IL-13 antibodies were grouped in three different bins by measuring the ability of two antibodies to bind to antigen at the same time (one antibody capturing the antigen on a bead and the other antibody used for detection). The signal on the beads in the absence of antigen was subtracted from the signal obtained in the presence of antigen. The signal of each detection antibody was divided by the signal of the capture antibody to determine the fold increase in binding as shown in Table 17.2. The antibodies were then binned based on similar binding patterns on the capture antibodies. The data identified the presence of three bins of antibody binding for the nine detection antibodies tested (Table 17.2).

TABLE 17.2

| | | Ab used for Detection | | | | | | | | |
|---|---|---|---|---|---|---|---|---|---|---|
| | | 353 | 11.18 | 713 | 731 | 693 | 623 | 602 | 643 | 785 | G2 |
| Ab on Beads | 353 | 1.0 | 2.3 | 0.6 | 0.6 | 2.5 | 3.1 | 2.9 | 3.0 | 3.3 | 0.2 |
| | 11.18 | 4.2 | 1.0 | 6.6 | 6.9 | 2.3 | 0.9 | 0.8 | 0.9 | 0.7 | 0.5 |
| | BIN: | 1 | 2 | 1 | 1 | 3 | 2 | 2 | 2 | 2 | N/A |

Briefly, mouse anti-human IgG1, 2, 3, 4 (BD Pharmingen 555784) conjugated beads were added to capture antibody (353 & 11.18; 5 ug/mL) in individual darkened eppendorf tubes. The tubes were rotated in the dark at 4° overnight. Beads were aliquoted to each well of a filter plate (2500 of each bead/well) and washed.

IL-13-RbIg (5 µg/ml) and controls (media only) were added to the filter plate 60 µl/well, which was then incubated in the dark at room temperature for 1 hour on a shaker and subsequently washed 2 times.

Secondary antibodies diluted in media at 60 µl/well (1 antibody per well) were added. The antibodies were used at the following concentrations (353B-5 g/ml; 11.18.31-5 µg/ml; 713-0.56 µg/ml; 731-1.28 µg/ml; 693-2.7 µg/ml; 623-5.7 µg/ml; 602-11 g/ml; 643-4.3 µg/ml; 785-5.5 µg/ml; 763-5.7 µg/ml; G2 control-5 µg/ml). Plates were then incubated for two hours at room temperature and washed.

Biotinylated Mo-anti-HuIg G1, 2, 3, 4 (BD Pharmingen # 555785) diluted in medium at 5 µg/ml was added to each well (60 µl/well) and the plates were incubated in the dark for 1 hour on a shaker at room temperature. After washing 60 µl/well Streptavidin-PE (5 ug/mL; Pharm # 554061) diluted in medium was added. Plates were incubated in the dark for 20 min on the shaker at room temperature and washed 2 times.

Each well was resuspended in 80 µl storage/blocking buffer (PBS, 10 mg/ml BSA, 0.05% w/v sodium azide) by carefully pipette up and down several times to resuspend beads. Each well was analyzed by reading on Luminex with the gate set between 8,400 and 14,500.

The Luminex platform is a fluorescence bead based technology which enables one to run multiple assays at once. The Luminex reader is able to ascertain positive signaling events on different coded microspheres. This allows one to coat each bead separately, then mix the differentially coated microspheres together and then in one step assay antibody binding to each of the different microspheres. For isotyping antibodies, microspheres were coated in such a manner in that each bead was able to specifically bind a particular heavy chain or light chain isotype. The microspheres were then mixed together and hybridoma supernatant for each antibody was added. After a 20 minute incubation, the microspheres were washed, and the bound antibody was detected using a fluorescently labeled secondary antibody. The microspheres were then read using the Luminex reader.

Example 3

In Vivo Data

Humanized IL-13 Mice

Humanized IL-13 mice, in which the gene encoding murine IL-13 was disrupted by the insertion of a cDNA encoding human IL-13, were generated at Lexicon (The Woodlands, Tex.). Mice were backcrossed onto the A/J strain to ensure that the mice were susceptible to allergen-induced airway hyper-reactivity as previously described (Ewert et al., (2000) Am. J. Respir. Cell. Mol. Biol.).

To demonstrate that humanized IL-13 mice produce only human IL-13 and no murine IL-13, cytokine production from OVA-specific CD4+ T cells derived from humanized IL-13 mice (6-8 wk of age) were compared with CD4+ T cells derived from WT mice. Mice were sensitized by i.p. injection with 50 µg OVA/1 mg Imject Alum (Pierce, Rockford, Ill.) in 0.9% sterile saline or with PBS (3 mice per treatment). Seven days after sensitization, mice were sacrificed, and single-cell suspensions of the spleens were prepared. Erythrocytes were lysed, and the washed splenocytes were resuspended at $5\times10^6$ cells/ml in complete medium consisting of HL-1 (BioWhittaker, Walkersville, Md.) with 10% heat-inactivated FCS, 2 mM L-glutamine, and 50 mg/L neomycin sulfate. Splenocytes were then cultured for 4 days at 37° C. in the presence of 200 µg/ml OVA to generate Ag-reactive CD4+ T cells. CD4+ T cells ($5\times10^5$ cells/well) were isolated and then incubated with freshly isolated mitomycin C (25 µg/ml)-treated splenocytes ($5\times10^5$ cells/well) from WT mice in complete medium in the presence of 200 µg/ml OVA in 96-well plates (250 µl/well) for 96 hours.

Figure 7:
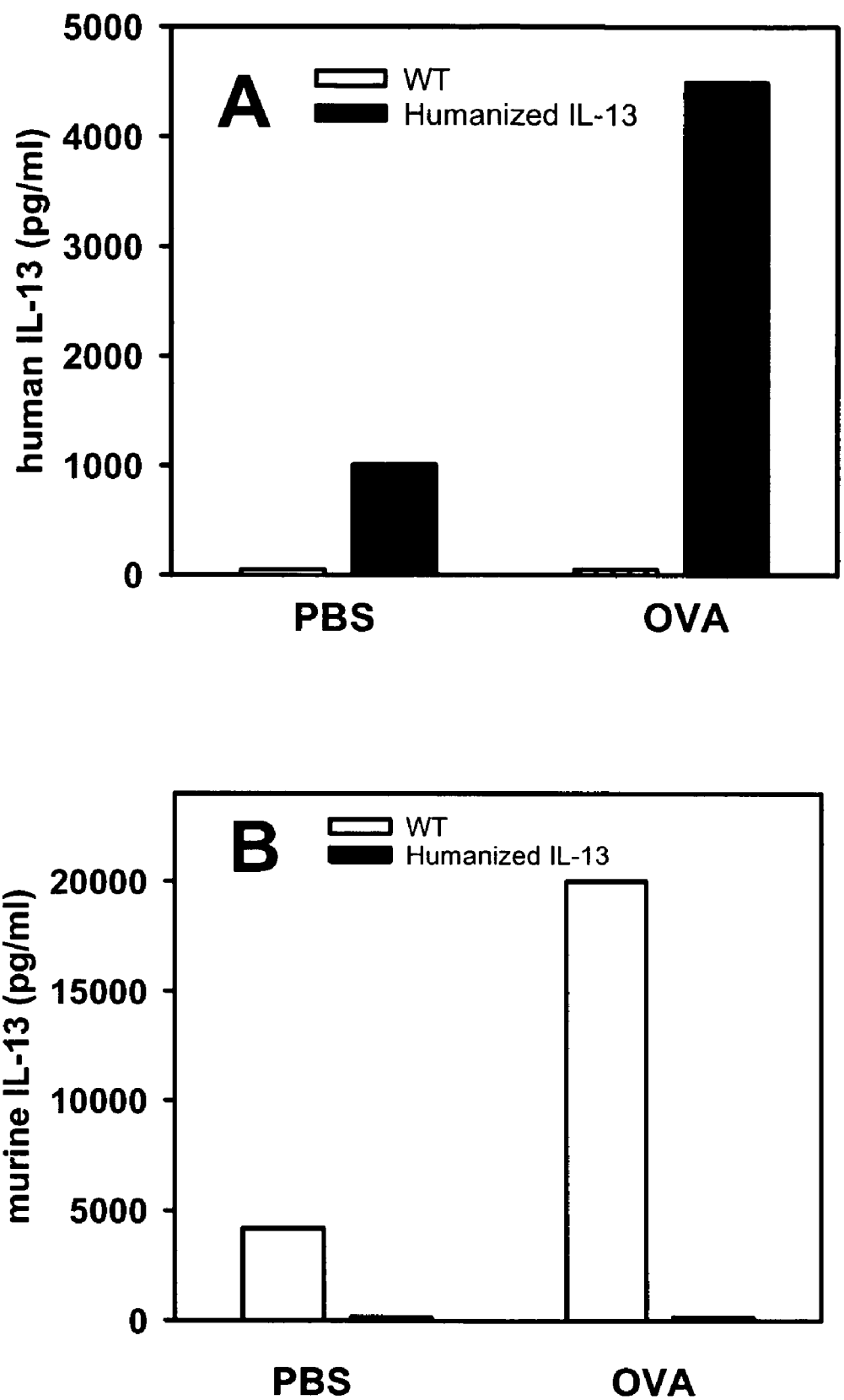
FIG. 7A and FIG. 7B are bar graphs showing that $CD4^+$ T cells from humanized IL-13 mice produce human IL-13 but not murine IL-13.

Cell-free culture supernatants were collected and tested for cytokine production. Human and murine IL-13 (DuoSet, R&D Systems, Minneapolis, Minn.) concentrations were determined by ELISA according to the manufacturer's protocol. As expected, CD4+ T cells derived from humanized IL-13 mice after in vitro OVA restimulation produced human IL-13 and no murine IL-13 (FIG. 7A). In contrast, CD4+ T cells derived from WT mice produced murine IL-13 and no murine IL-13 (FIG. 7 B).

Airway Hyper-Reactivity

The anti-IL-13 antibodies 731 and 623 were tested in OVA-induced asthma models using the humanized IL-13 mice described above. For the measurement of airway reactivity to the intravenous administration of acetylcholine, a 24 day protocol was used. Briefly, mice were immunized by an intraperitoneal injection of OVA (10 µg; crude grade IV; Sigma) in PBS (0.2 ml). PBS alone was used as a control. Fourteen days after immunization, mice were anesthetized with a mixture of ketamine and xylazine [45 and 8 mg per kilogram of body weight (mg/kg), respectively] and challenged intratracheally with 50 µl of a 1.5% solution of OVA or an equivalent volume of PBS as a control.

Figure 8:
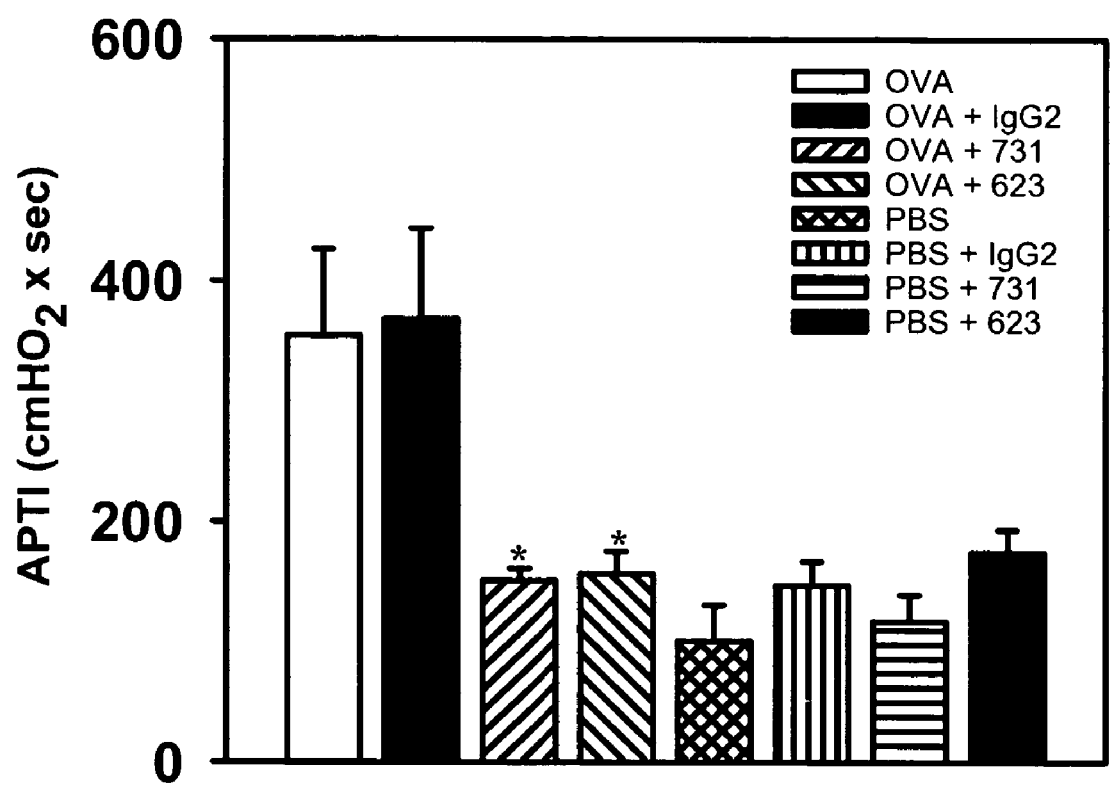
FIG. 8 is a graph demonstrating that anti-IL-13 antibodies 731 and 623 inhibit airway hyperresponsiveness.

Seven days after the first antigen challenge, mice were challenged again intratracheally with either OVA or PBS. The 731 and 623 antibodies were administered intraperitoneally at a dose of 100 µg/mouse one day before each challenge (days 13 and 20). Control mice received PBS or an irrelevant IgG2 as isotype control. Three days after the final intratracheal challenge, mice were anesthetized with sodium pentobarbital (90 mg/kg), intubated, ventilated at a rate of 120 breaths/min with a constant tidal volume of air (0.2 ml), and paralyzed with decamethonium bromide (25 mg/kg). After a stable airway pressure was established, acetylcholine was injected intravenously (50 µg/kg), and the dynamic airway pressure was measured for 5 min. The airway hyperresponsiveness (AHR) to the acetylcholine challenge was measured. The airway hyperresponsiveness to acetylcholine challenge is defined by the time-integrated rise in peak airway pressure [airway-pressure-time index (APTI) in centimeters of $H_2O\times$ seconds]. * P<0.05, compared to the OVA+IgG2 control group [one-way analysis of variance (ANOVA) followed by Fisher's least significant difference test for multiple comparisons]. Treatment with 731 or 623 resulted in a complete reversal of OVA-induced AHR (FIG. 8). In this example, complete reversal means that the addition of the antibody with OVA results in an effect similar to one in which there is no OVA and only antibodies are added (e.g., IgG2). n=4 mice/group in the PBS, PBS+IgG2, PBS+731 and OVA groups; n=5 mice/group in the OVA+IgG2 group; n=6 mice/group in the PBS+623 and OVA+731 group; n=8 mice/group in the OVA+623 group. Data are mean±SE.

OVA-Induced Mucus Production

An 18 day protocol was used for the measurement of OVA-induced mucus production. After subcutaneous priming with Ovalbumin (OVA, 25 µg; crude grade IV) (Sigma) in 2 mg Imject Alum on days 0 and 7, mice were anesthetized with isofluorane and challenged intranasally with 50 µl of a 1.5% solution of OVA in PBS on days 14, 15, and 17. Control mice received alum as priming or PBS as challenge.

The 731 and 623 antibodies were administered intraperitoneally at a dose of 100 µg/mouse on days 13, 15, and 17.

Figure 9:
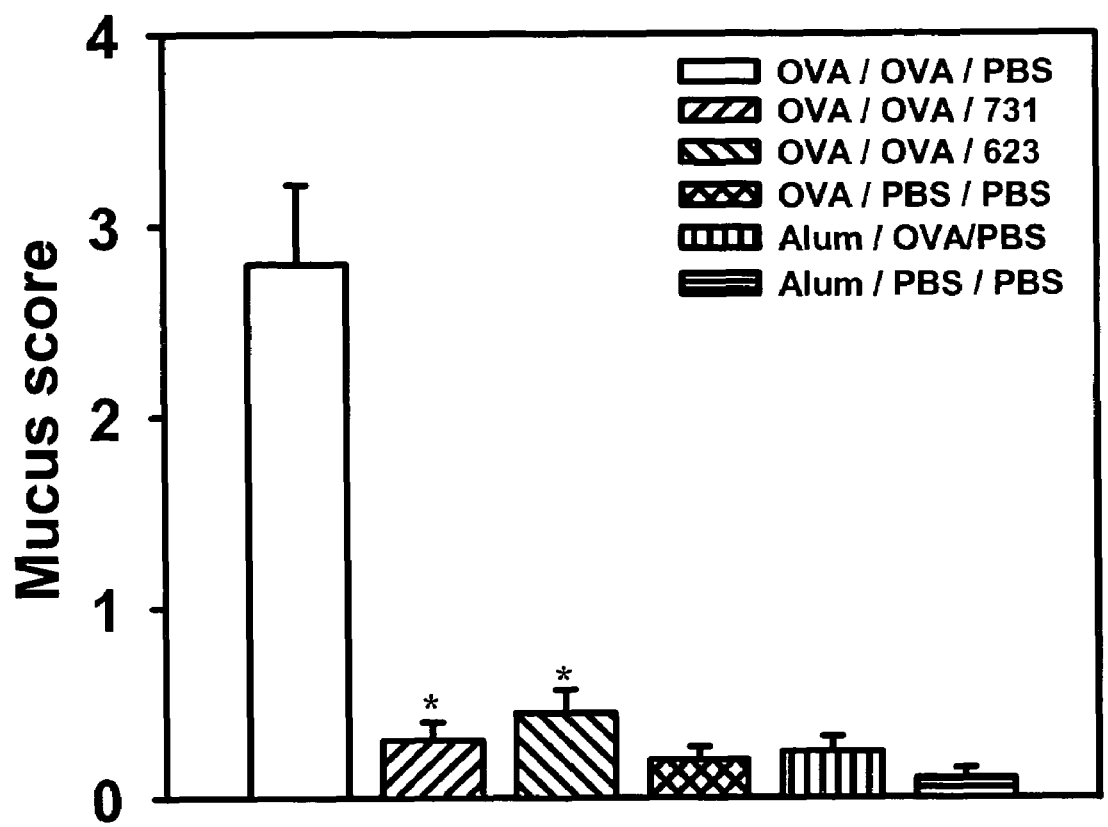
FIG. 9 is a bar graph demonstrating that 731 and 623 inhibit mucus production.
Figure 11:
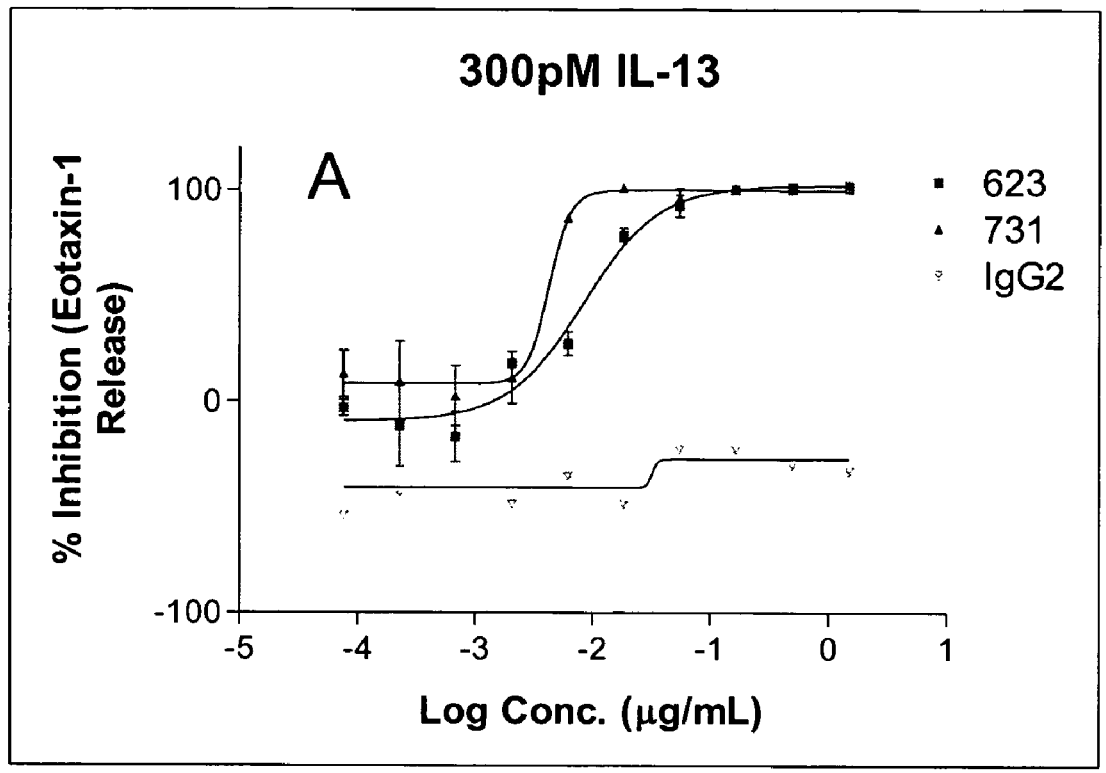
FIGS. 11A-D are graphs displaying the percent inhibition of the eotaxin release induced by IL-13 or IL-13Q110R variant by recombinant antibodies 623 and 731 compared to an isotype matched control.
Figure 11:
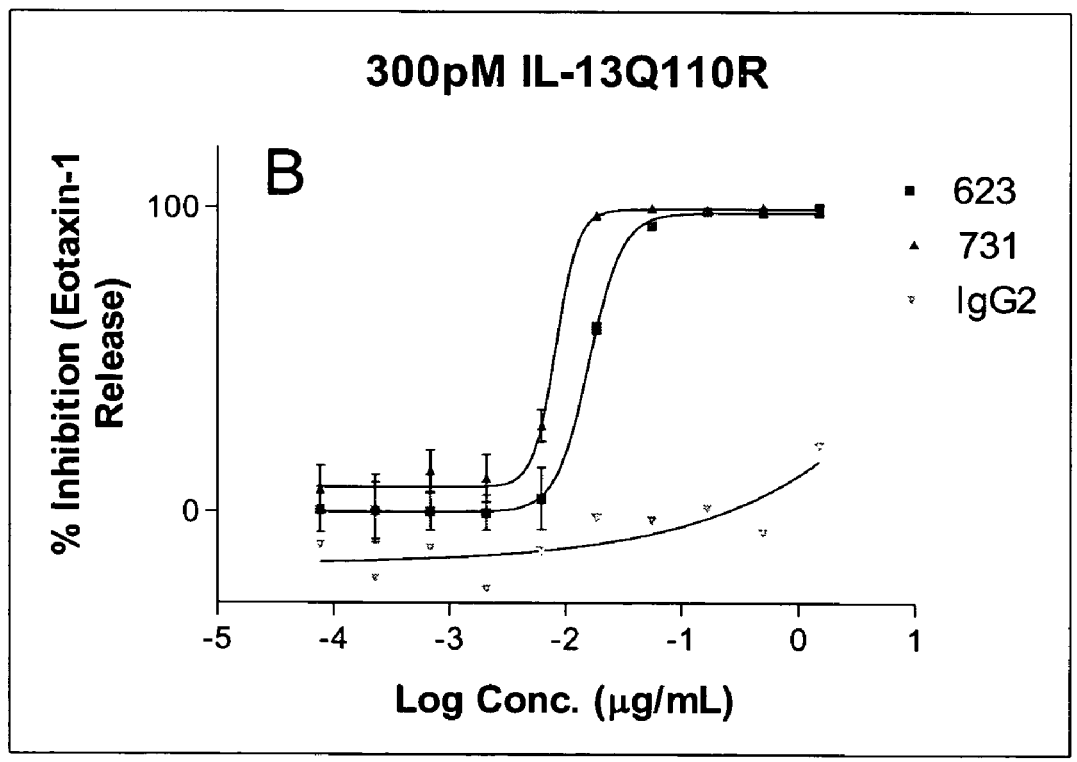
Figure 11:
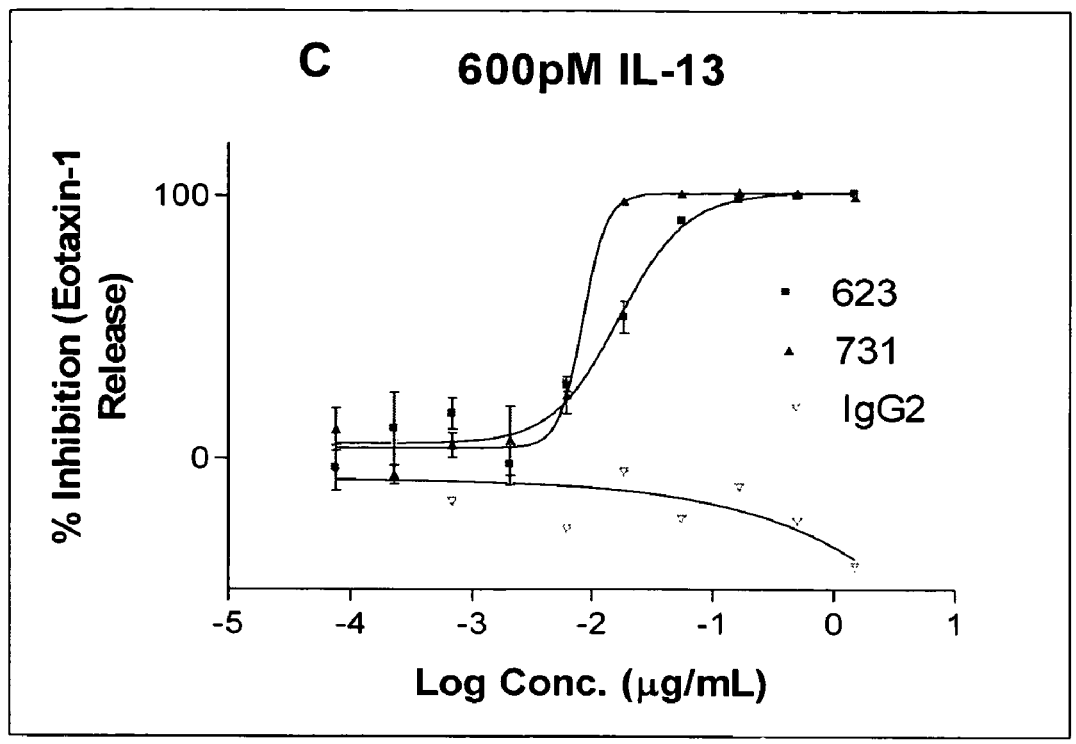
Figure 11:
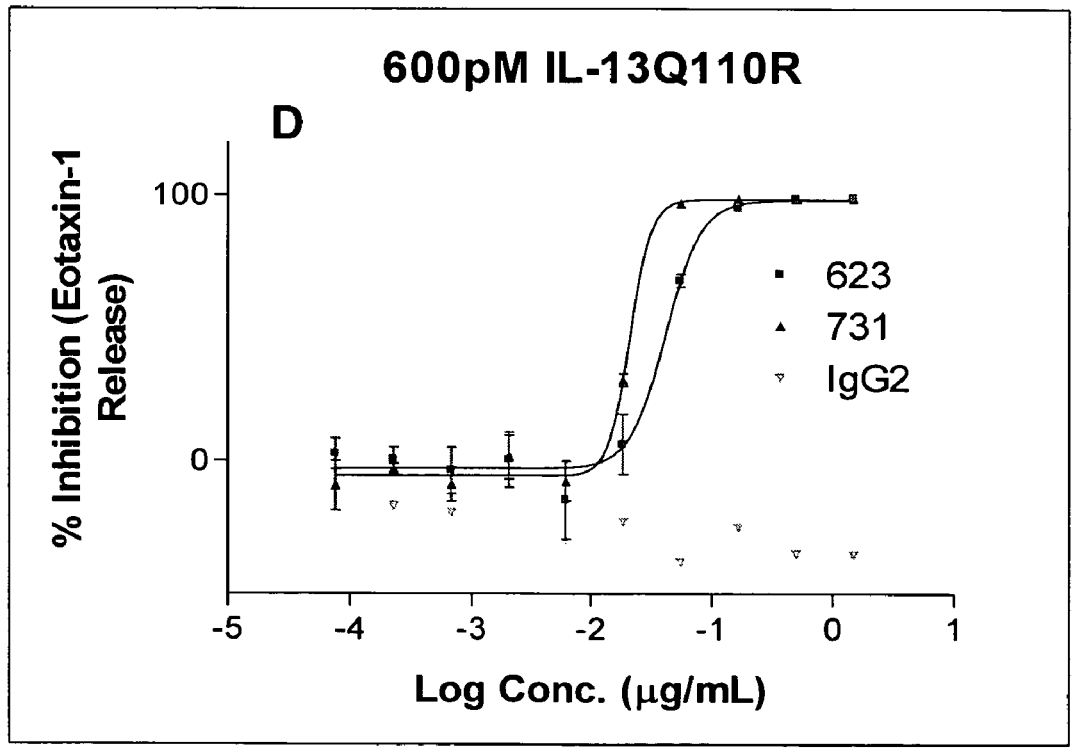

Control mice received PBS. On day 18 mice were sacrificed and lungs were collected after being perfused. Lung tissue, including central and peripheral airways, was fixed in 10% formalin, washed in 70% ethanol, dehydrated, embedded in glycol methacrylate, cut into 4-µM sections, mounted on slides, and stained with hematoxylin and eosin, plus Periodic acid-Schiff (PAS). Lung sections (one section per animal) were examined at 20× magnification. Five fields were selected randomly and for each section the number of bronchi was counted in each field. Sections were scored on a scale from 0 to 4 (0: <5% PAS+ goblet cells; 1: 5 to 25%; 2: 25 to 50%; 3: 50 to 75%; 4: >75%). To obtain the histologic goblet cell score (expressed as arbitrary units; U) the sum of the airway scores from each lung was divided by the number of bronchi examined. Five out of eight mice died in the OVA treated group. No mice died in the other groups. Administration of 731 and 623 effectively reversed OVA-induced increase in mucus-containing cells in the airways (FIG. 9) Data are mean±SE. n=3 for OVA/OVA/PBS group (initially n=8); n=8 for OVA/OVA/731 group, n=4 for OVA/OVA/623 group; n=4 for OVA/PBS/PBS group, n=5 for Alum/OVA/PBS, and Alum/PBS/PBS groups. *$p<0.01$ vs OVA/OVA/PBS group by unpaired Student t-test.

The above use of the murine models and mucus and AHR measurements for testing asthma is an accurate and scientifically accepted model for testing for the effectiveness of a drug for treating asthma. (Willis-Karp M., Murine models of asthma in understanding dysregulation in human asthma, *Immunopharmacology,* 25:48:263-8 (2000)). Moreover, the model is predicted to be reliable for those IL-13 related disorders that share symptoms that are similar to at least one of the symptoms shown in these mouse models. As such, this and similar such animal models will be sufficient for similarly testing the other identified IL-13 related disorders.

Example 4

Structural Analysis of Antibodies

The variable heavy chains and the variable light chains for the antibodies shown in Table 1 were sequenced to determine their DNA sequences. The complete sequence information for all anti-IL-13 antibodies are shown in the sequence listing submitted herewith, including nucleotide and amino acid sequences.

Table 18 shows the amino acid sequences of the heavy chain genes for a variety of the IL-13 antibodies described herein. Table 18 also shows the amino acid sequences corresponding to the CDRs and framework regions for each antibody, along with a comparison to its germline sequence.

Table 19 shows the amino acid sequences of the kappa light chain genes for a variety of the IL-13 antibodies described herein. Table 19 also shows the amino acid sequences corresponding to the CDRs and framework regions for each antibody, along with a comparison to its germline sequence.

Table 20 shows the amino acid sequences of the lambda light chain genes for a variety of the IL-13 antibodies described herein. Table 20 also shows the amino acid sequences corresponding to the CDRs and framework regions for each antibody, along with a comparison to its germline sequence.

TABLE 18

| Single Cell | SEQ ID NO | V Heavy/D/J | FR1 | CDR1 | FR2 |
|---|---|---|---|---|---|
| — | 81 | Germline | EVQLVESGGGLVKPGGSLRLSCAAS | GFTFSSYSMN | WVRQAPGKGLEWVS |
| 157 | 22 | VH3-21/D1-26/JH3b | EVQLVESGGGLVKPGGSLRLSCAAS | GFTFSSYSMN | WVRQAPGKGLEWVS |
| 183 | 30 | | EVQLVESGGGLVKPGGSLRLSCAAS | GFTFSSYSMN | WVRQAPGKGLEWVS |
| 176 | 26 | | EVQLVESGGGLVKPGGSLRLSCAAS | GFTFSSYSMN | WVRQAPGKCLEWVS |
| 243 | 18 | | EVQLVESGGGLVKPGGSLRLSCAAS | GFTFSSYSMN | WVRQAPGKCLEWVS |
| 264 | 14 | | EVQLVESGGGLVKPGGSLRLSCAAS | GFTFSSYSMN | WVRQAPGKGLEWVS |
| — | 82 | Germline | QVQLQESGPGLVKPSETLSLTCTVS | GGSISSYYWS | WIRQPPGKGLEWIG |
| 353 | 6 | VH4-59/D2-21/JH3B | QVQLQESGPGLVKPSETLSLTCTVS | GGSISTYYWS | WIRQPPGKGLEWIG |
| — | 83 | Germline | EVQLLESGGGLVQPGGSLRLSCAAS | GFTFSSYAMS | WVRQAPGKGLEWVS |
| 713 | 34 | VH3-23/D6-19/JH6B | EVQLLESGGGLVQPGGSLRLSCAAS | GFTFSSYAMS | WVRQAPGKGLEWVS |
| 731 | 38 | | EVQLLESGGGLVQPGGSLRLSCAAS | GFTFSSYAMS | WVRQAPGKGLEWVS |
| — | 84 | Germline | EVQLLESGGGLVQPGGSLRLSCAAS | GFTFSSYAMS | WVRQAPGKGLEWVS |
| 785 | 58 | VH3-23/D3-3/JH4B | EVQLLESGGGLVQPGGSLRLSCAAS | GFTFSSYAMS | WVRQAPGKGLEWVS |
| — | 85 | Germline | QVQLQESGPGLVKPSETLSLTCTVS | GGSTSSYYWS | WIRQPAGKGLEWIG |
| 693 | 42 | VH4-4/D5-5/JH4B | QVQLQESGPGLVKPSETLSLTCSVS | GGSISSYYWS | WIRQPAGKGLEWIG |
| — | 86 | Germline | EVQLVESGGGLVKPGGSLRLSCAAS | GFTFSNAWMS | WVRQAPGKGLEWVG |
| 623 | 50 | VH3-15/D1-26/JH6B | EVQLVESGGGLVKPGGSLRLSCAAS | GFTFSNAWMS | WVRQAPGKGLEWVG |
| 643 | 46 | | EVQLVESGGGLVKPGGSLRLSCAAS | GFTFSNAWMS | WVRQAPGKGLEWVG |
| 602 | 54 | | EVQLVESGGGLVKPGGSLRLSCAAS | GFTFSNAWMS | WVRQAPGKGLEWVG |
| — | 87 | Germline | QVQLVESGGGVVQPGRSLRLSCAAS | GFTFSSYGMH | WVRQAPGKGLEWVA |
| 11.18 | 2 | VH3-33/D6-19/JH5B | QVQLVESGGGVVQPGRSLRLSCVAS | GFTFSSYDMH | WVRQAPGKGLEWVA |
| — | 88 | Germline | EVQLVESGGGLVKPGGSLRLSCAAS | GFTFSSYSMN | WVRQAPGKGLEWVS |
| 356 | 10 | VH3-21/NA/JH6B | EVQLVESGGGLVKPGGSLRLSCAAS | GFTFSDYNMH | WVRQAPGKGLEWVS |

TABLE 18-continued

| Single Cell | SEQ ID NO | CDR2 | FR3 | CDR3 | FR4 |
|---|---|---|---|---|---|
| — | 81 | SISSSSSYIYYADSVKG | RFTISRDNAKNSLYLQMNSLRAEDTAVYYCAR | | WGQGTMVTVSS |
| 157 | 22 | YISTSYNYIYYADSVKG | RFTISRDNAKNSLYLQMNSLPAEDTAVYYCAR | DQVGATLDAFDI | WGQGTMVTVSS |
| 183 | 30 | YISSSYNYIYYGDSVKG | RFTISRDNAKNSLYLQMNSLRAEDTAVYYCAR | DQVGATLDAFDI | WGQGTMVTVSS |
| 176 | 26 | YTSTSNSYIYYADSVKG | RFTISRDNAKNSLYLQMNSLRAEDTAVYYCAR | DQVGATLDAFDI | WGQGTMVTVSS |
| 243 | 18 | YISTSNSYIYYADSVKG | RFTISRDNAKNSLYLQMNSLRAEDTAVYYCAR | DQVGATLDAFDI | WGQGTMVTVSS |
| 264 | 14 | YISTSNSYIYYADSVKG | RFTISRDNAKNSLYLQMNSLRAEDTAVYYCAR | DQVGATLDAFDI | WGQGTMVTVSS |
| | 82 | YIYYSGSTNYNPSLKS | RVTISVDTSKNQFSLKLSSVTAADTAVYYCAR | | WGQGTMVTVSS |
| 353 | 6 | YIYYSGSTNYNPSLKS | RVTISVDTSKNQFSLKLSSVTAADTAVYYCAR | DGGHYWDDAFDI | WGQGTMVTVSS |
| — | 83 | AISGSGGSTYYADSVKG | RFTISRDNSKNTLYLQMNSLRAEDTAVYYCAK | | WGQGTTVTVSS |
| 713 | 34 | AFSGSGGSTYYADSVKG | RFTISRDNSKNTLYLQMNSLRAEDTAVYYCVQ | DGLGPYFYNYGMDV | WGQGTTVTVSS |
| 731 | 38 | AFSGSGGSTYYADSVKG | RFTISRDNSKNTLYLQMNSLRAEDTAVYYCVQ | DGLGPYFYNYGMDV | WGQGTTVTVSS |
| — | 84 | AISGSGGSTYYADSVKG | RFTISRDNSKNTLYLQMNSLRAEDTAVYYCAK | | WGQGTLVTVSS |
| 785 | 58 | AISGSGGSTYYADSVKG | RFTISRDNSKNTLYLQMNSLRAEDTAVYYCAK | ADFWSGTLWGFDY | WGQGTLVTVSS |
| — | 85 | RIYTSGSTNYNPSLKS | RVTMSVDTSKNQFSLKLSSVTAADTAVYYCAR | | WGQGTLVTVSS |
| 693 | 42 | RIYMTGRTNYNSSLKS | RVTMSIDTSKNQLSLKLSFMTAADTAVYYCAR | ESGSSYSYDY | WGQGTLVTVSS |
| — | 86 | RIKSKTDGGTTDYAAPVKG | RFTTSRDDSKNTLYLQMNSLKTEDTAVYYCTT | | WGQGTLVTVSS |
| 623 | 50 | RIRSEIDGGTTNYAAPVKG | RFTISRDDSKNTLYLQMNSLKTEDTAVYYCAT | DQVGAYYGDYYGMDV | WGQGTLVTVSS |
| 643 | 46 | RIRSEIDGGTTNYAAPVKG | RFTISRDDSKNTLYLQMNSLRTEDTAVYYCAT | DQVGAYYGDYYGMDV | WGQGTLVTVSS |
| 602 | 54 | RIRSKTDGGTINYAAPVKG | RFTISRDDSKNTLYLQMNSLKTEDTAVYYCAT | DQVGAYYGDYYGMDV | WGQGTLVTVSS |
| — | 87 | VTWYDGSNKYYADSVKG | RFTISRDNSKNTLYLQMNSLRAEDTAVYYCAR | | WGQGTLVTVSS |
| 11.18 | 2 | VIWYDGSNKYYADSVQG | RFTISRDNSKNTLYLQMNSLRAEDTAVYYCTS | EDSSGWYDGWFDP | WGQGTLVTVSS |
| — | 88 | SISSSSSYIYYADSVKG | RFTISRDNAKNSLYLQMNSLPAEDTAVYYCAR | | WGQGTTVTVSS |
| 356 | 10 | STSYSSTYIYYADSVRG | RFTISRDNAKNSLYLQMNSLRAEDTAVFYCAR | EDYYYYGLDV | WGQGTTVTVSS |

TABLE 19

| Single Cell | SEQ ID NO | Light--V Kappa/J | FR1 | CDR1 | FR2 |
|---|---|---|---|---|---|
| | 89 | Germline | DIQMTQSPSSLSASVGDRVTITC | RASQGIRNDLG | WYQQKPGKAPKRLIY |
| 157 | 24 | A30(Vk1)/JK3 | DIQMTQSPSSLSASVGDRVTITC | RASQGIGDDLG | WYQQKPGKAPKRLIY |
| 183 | 32 | | DIQMTQSPSSLSASVGDRVTITC | RASQGIGDDLG | WYQQKPGKAPKRLIY |
| 176 | 28 | | DIQMTQSPSSLSASVGDRVTFTC | RASQDITDDLG | WYQQKPGKAPKRLIY |
| 243 | 20 | | DIQMTQSPSSLSASVGDRVTFTC | RASQDITDDLG | WYQQKPGKAPKRLIY |
| 264 | 16 | | DIQMTQSPSSLSASVGDRVTFTC | RASQDITDDLG | WYQQKPGKAPKRLIY |
| 353 | 8 | | DIQMTQSPSSLSASVGDRVTITC | RASQGIRNDLD | WYQQKPGKAPKRLIY |
| — | 90 | Germline | DIQMTQSPSSLSASVGDRVTITC | RASQGISNYLA | WYQQKPGKVPKLLIY |
| 11.18 | 4 | A20/JK3 | DIQMTQSPSSLSASVGDRVTITC | RASQGISNYLA | WYQQKPGKVPKVLIY |
| — | 91 | Germline | DIQMTQSPSSLSASVGDRVTITC | RASQGTRNDLG | WYQQKPGKAPKRLIY |
| 356 | 12 | A20/JK2 | DIQMTQSPSSLSASVGDRVTTTC | RASQGIRNDLG | WYQQKPGKAPKRLIY |

| Single Cell | SEQ ID NO | CDR2 | FR3 | CDR3 | J |
|---|---|---|---|---|---|
| | 89 | AASSLQS | GVPSRFSGSGSGTEFTLTISSLQPEDFATYYC | | FGPGTKVDIK |
| 157 | 24 | AASSLQS | GVPSRFSGSGSGTEFTLTISSLQPEDFATYYC | LQHNSYPFT | FGPGTRVDIK |
| 183 | 32 | AASSLQS | GVPSRFSGSGSGTEFTLTISSLQPEDFATYYC | LQHNSYPFT | FGPGTRVDIK |
| 176 | 28 | AASSLQS | GVPPRFSGSGSGTEFTLTISSLQPEDFATYYC | LQHNSYPFT | FGPGTKVDIR |
| 243 | 20 | AASSLQS | GVPSRFSGSGSGTEFTLTISSLQPEDFATYYC | LQHNSYPFT | FGPGTKVDIR |
| 264 | 16 | AASSLQS | GVPSRFSGSGSGTEFTLTISSLQPEDFATYYC | LQHNSYPFT | FGPGTKVDIR |
| 353 | 8 | DASSLQS | GVPSRFSGSGSGTEFTLTISSLQPEDFATYYC | LQHDSYPFT | FGPGTKVDIK |
| — | 90 | AASTLQS | GVPSRFSGSGSGTDFTLTISSLQPEDVATYYC | | FGPGTKVDIK |
| 11.18 | 4 | AASTLQS | GVPSRFSGSGSGTDFTLTISSLQPEDVATYYC | QKYNSAPFT | FGPGTKVDIK |
| — | 91 | AASSLQS | GVPSRFSGSGSGTEFTLTISSLQPEDPATYYC | | FGQGTKLEIK |
| 356 | 12 | AASSLQS | GVPSRFSGSGSGTEFTLTISSLQPEDPATYYC | LQHNSYPWT | FGQGTKVEIK |

TABLE 20

| Single Cell | SEQ ID NO | Light-V Lambda/J | FR1 | CDR1 | FR2 |
|---|---|---|---|---|---|
| — | 92 | Germline | SYELTQPPSVSVSPGQTASITC | SGDKLGDKYAC | WYQQKPGQSPVLVIY |
| 713 | 36 | V2-1/JL1 | SYELTQPPSVSVSPGQTASITC | SGDKLGDKYTC | WFQQKPGQSPVLVIY |
| 731 | 40 | | SYELTQPPSVSVSPGQTASITC | SGDKLGDKYAC | WFQQKPGQSPVLVIY |
| — | 93 | Germline | SYVLTQPPSVSVAPGQTARITC | GGNNIGSKSVH | WYQQKPGQAPVLVVY |
| 693 | 44 | V2-14/ JL2 | SYVLTQPPSVSVAPGQTARITC | GGNNIGSKGVH | WYQQKPGQAPVLVVY |
| 785 | 60 | | SYVLTQPPSVSVAPGQTARITC | GGNNIGNKIVH | WYQQKPGQAPVLVVY |
| — | 94 | Germline | SYELTQPPSVSVSPGQTARITC | SGDALPKKYAY | WYQQKSGQAPVLVIY |
| 623 | 52 | V2-7/JL3 | SYELTQPPSVSVSPGQTARITC | SGDALPEKYAY | WYQQKSGQAPVLVIY |
| 643 | 48 | | SYELTQPPSVSVSPGQTARITC | SGDALPEKYAY | WYQQKSGQAPVLVIY |
| 602 | 56 | | SYELTQPPSVSVSPGQTARITC | SGDALPEKYAY | WYQQKSGQAPVLVIY |

| Single Cell | SEQ ID NO | CDR2 | FR3 | CDR3 | J |
|---|---|---|---|---|---|
| — | 92 | QDSKRPS | GIPERFSGSNSGNTATLTISGTQAMDEADYYC | | FGTGTKVTVL |
| 713 | 36 | HDSKRPS | GIPERFSGSNSGDTATLTISGTQAMDEADYYC | QAWDSSTYV | FGTGTKVTVL |
| 731 | 40 | HDSKRPS | GIPERFSGSNSGDTATLTISGTQAMDEADYYC | QAWDSSTYV | FGTGTKVTVL |
| — | 93 | DDSDRPS | GIPERFSGSNSGNTATLTISRVEAGDEADYYC | | FGGGTKLTVL |
| 693 | 44 | DDSDRPS | GIPERFSGSNSGNTATLTISRVEAGDEADYYC | QVWVSSSDHHVV | FGGGTKLTVV |
| 785 | 60 | DDSDRPS | GIPERFSGSNSGNTATLTISRVEAGDEADYYC | QVWDSSSDHVV | FGGGTKLTVL |
| — | 94 | EDSKRPS | GIPERFSGSSSGTMATLTISGAQVEDEADYYC | | FGGGTKLTVL |
| 623 | 52 | EDSKRPS | GTPERFSGSSSGTMATLTTSGAQVEDEADYYC | HSTDSSGNHGV | FGGGTKLTVL |
| 643 | 48 | EDSKRPS | GIPERFSGSSSGTMATLTISGAQVEDEADYYC | HSTDSSGNHGV | FGGGTKLTVL |
| 602 | 56 | EDTKRPS | GIPERFSGSSSGTMATLTISGAQVEDEADYYC | YSTDSSGNHGV | FGGGTKLTVL |

In some embodiments, the above sequences are used to generate variants of the antibodies. For example, creating the variants can involve using the above sequences and structural breakdown (by sections or regions of the antibody) of the sequences to identify identical, similar, and nonconserved regions of the antibody. Sections of the antibody that are highly conserved or identical will be maintained in the variant, while sections that vary greatly between antibodies can be allowed to vary in the new variant. Thus, "conserved" variants can readily be created by using the above listing of antibody sequences. As will be appreciated by one of skill in the art, there are already many variants listed above, e.g., 713 and 731 or 623 and 643 which differ in their amino acid sequences. In some embodiments, no more than 40% of the amino acids in each of the above sections (e.g., CDR1, CDR2, CDR3, FR1, J, etc.) are allowed to differ, for example, 40-30, 30-20, 20-15, 15-10, 10-5, 5-2, 2-1, or 1% or less of the amino acids in each section are allowed to be changed to nonconservative amino acids for the resulting antibody to be considered a variant antibody. As is demonstrated herein, the variants appear to retain their various functions. Additional guidance can be found in identifying antibodies that bind to the same epitope and then analyzing the sequences for structural similarities (primary, secondary, tertiary, etc.) just between those antibodies.

In some embodiments, antibodies that bind to IL-13, with at least a subset of the above identified sequence are also contemplated. For example, an IL-13 fully human antibody with a CDR1 region as described above, or, more particularly, with a CDR1 region that has the sequence GFTF in it can be used. Similarly, an antibody with a light chain CDR2 region ending in Kn or a heavy chain CDR2 region ending in VKG, or a CDR3 region starting with GMDV can also be used. Any of the above sequences or subsequences can similarly be used, especially when the sequences are common across antibodies.

As noted herein, in some embodiments, the antibodies bind with the same affinity to IL-13 as they do to other variants of IL-13. In some embodiments, the other variants of IL-13 include the Q110R variant. Such antibodies, and variants thereof, can be created by the above disclosed methods. Additional guidance can be found by sequence comparisons to identify conserved regions in antibodies that bind with similar affinity to the wild-type and other IL-13 variants. IL-13 variants are known in the art and are readily identified by one of skill in the art. Examples of IL-13 variants can be found in Heinzmann et al., (Genentic variants of IL-13 signaling and human asthma and atopy, *Human Molecular Genetics,* 9:549-559 (2000)), incorporated by reference in its entirety.

Example 5

Use of Anti-IL-13 Antibodies as a Diagnostic Agents for Detection of IL-13 in a Sample An Enzyme-Linked Immunosorbent Assay (ELISA) for the detection of IL-13 in a sample may be developed. In the assay, wells of a microtiter plate, such as a 96-well microtiter plate or a 384-well microtiter plate, are adsorbed for several hours with a first fully human monoclonal antibody directed against IL-13. The immobilized antibody serves as a capture antibody for IL-13 that may be present in a test sample. The wells are rinsed and treated with a blocking agent such as milk protein or albumin to prevent nonspecific adsorption of the analyte.

Subsequently the wells are treated with a test sample suspected of containing IL-13, or with a solution containing a standard amount of the antigen.

After rinsing away the test sample or standard, the wells are treated with a second fully human monoclonal anti-IL-13 antibody that is labeled by conjugation with biotin. The labeled anti-IL-13 antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

Example 6

Treatment of COPD in Humans

A patient suffering from COPD is identified. A dosage of 5 mg/kg of the anti-IL-13 antibody 623 and/or 731 is administered by intravenous injection to the patient. The level of eotaxin, C10, and/or TARC in the patient is determined. If the level of eotaxin, C10, and/or TARC is too high, additional mAb is administered to the patient until a "normal" level of eotaxin, C10, and/or TARC is obtained. The anti-IL-13 antibody causes an inhibition in the production of mucous, the development of bronchial epithelium hyperplasia, and spasm of bronchial smooth muscle. This inhibition of mucous production and smooth muscle contraction reduces blockade of air passage with improved ventilation.

Example 7

Treatment of Chronic Bronchitis in Humans

A patient suffering from COPD characterized by chronic bronchitis is identified. A dosage of 5 mg/kg of an anti-IL-13 antibody disclosed herein, preferably 623 or 731, is administered by intravenous injection to the patient. The level of eotaxin, C10, and/or TARC in the patient is determined. If the level of eotaxin, C10, and/or TARC is too high, additional mAb is administered to the patient until a "normal" level of eotaxin, C10, and/or TARC is obtained. The anti-IL-13 antibody causes a partial or complete inhibition of mucous production and bronchial smooth muscle contraction in the inflamed respiratory tissues. This inhibition of mucous production and smooth muscle contraction reduces blockade of air passage with improved ventilation.

Example 8

Treatment of Emphysema in Humans

A patient suffering from emphysema is identified. A dosage of 5 mg/kg of the IL-13 antibody is administered by intravenous injection to the patient. The level of eotaxin, C10, and/or TARC in the patient is determined. If the level of eotaxin, C10, and/or TARC is too high, additional mAb is administered to the patient until a "normal" level of eotaxin, C10, and/or TARC is obtained. The anti-IL-13 antibody causes a partial or complete decrease in inflammatory cell infiltrate in the respiratory tissues. Additionally, the anti-IL-13 antibody may block the ability IL-13 has to induce tissue damaging proteases.

Example 9

Treatment of Asthma in Humans

A patient suffering from asthma is identified. A dosage of 5 mg/kg of an anti-IL-13 antibody described herein, preferably 623 or 731, is administered by intravenous injection to the patient. The level of eotaxin, C10, and/or TARC in the patient is determined. If the level of eotaxin, C10, and/or TARC is too high, additional mAb is administered to the patient until a "normal" level of eotaxin, C10, and/or TARC is obtained. A booster administration is given later. The anti-IL-13 antibody reduces the severity of tissue damage to the lungs and air passages caused by the patient's immune response.

Example 10

Mapping of Conformational IL-13 Epitope Recognized by MAB 623

An overlapping peptide array (similar to that described in Example 2) spanning the human IL-13 sequence was generated to determine with greater specificity where mAb 623 binds to IL-13. Because mapping was insufficient with standard procedures, an optimized protocol especially suited for the detection of conformational binding sites was used. Peptide scans containing 12-mer human IL-13-derived peptides shifted by one amino acid were probed with mAb 623. Binding of mAb 623 to these arrayed human IL-13 derived peptides was analyzed by electrochemical transfer of the peptide bound antibody onto PVDF membranes, followed by detection with a peroxides labeled anti-human IgG antibody and chemiluminescence. One binding region was identified. It appears that the epitope for mAb 623 for IL-13 includes TQNQKAPLCN (SEQ ID NO: 95) sequence (residues 20-29 in loop A, of SEQ ID NO: 96, FIG. 10).

Example 11

Human IL-13 High Resolution Screen with MAB 623

This example provides a further high-resolution assay and result for the binding characteristics of mAb 623 to human IL-13. A goat anti-human polyclonal Ab (Fc specific) was amine coupled to all four flow cells of a CM5 Biacore™ chip at high surface capacity (4800-5400 resonance units, RUs, of pAb) with a Biacore 2000™ instrument. The running buffer and sample preparation buffer for all experiments was degassed HBS-P containing 100 µg/mL BSA. mAb 623 was diluted to 10.1 µg/mL in HBS-P for capturing of the mAb on the biosensor surface. mAb 623 was captured on flow cells 1, 2, and 4. On average 552, 211, and 390 RUs of mAb were captured, respectively, on the three experimental flow cells for each cycle using flow rates varying between 10-50 µL/min to achieve contact times varying between 12-60 seconds. Flow cell three served as a control. All IL-13 antigen (R&D Systems) injections were at 23° C. with a flow rate of 100 µL/min. Serially diluted (2-fold) IL-13 samples from 12.6-0.394 nM were randomly injected in triplicate for 60 seconds with several buffer injections interspersed for double referencing. The dissociation phase of the sensorgrams was followed for 30 minutes. The capture surface was regenerated with one, 15 second, injection of 146 mM phosphoric acid, pH 1.5. The sensorgram data were processed using Scrubber version 1.1 g. Data from all three flow cells were fit globally to a 1:1 interaction model with a term for mass transport included; the $R_{max}$ values for each flow cell were allowed to fit locally as is appropriate in this case since the capture levels were different on each of the three flow cells. The model fit the data satisfactorily and gave the results $k_a=7.3\times10^6$ M$^{-1}$s$^{-1}$, $k_d=2.5\times10^{-4}$ s$^{-1}$, $K_D=34$ pM.

Example 12

623 and 731 KINEXA Affinity for Marmoset IL-13

This example provides the affinity data for mAb 623 and mAb 731 for marmoset IL-13 from KINEXA analysis. $K_D$ controlled as well as antigen controlled experiments were done, similarly to the other KINEXA experiments, for marmoset IL13 with mAb 623. The n-curve analysis revealed that the final $K_D$ was 403 pM. A number of experiments were also performed for mAb 731 and by n-curve analysis, the $K_D$ for 731 was determined to be <7 pM.

Example 13

Medium Resolution Screen of MABS 623 & 731 with Human IL-13 Variant (IL-13Q110R)

This example present the binding characteristics of mAb 623 and mAb 731 to IL-13Q110R. Label-free surface plasmon resonance (SPR), or Biacore™ device, was utilized to measure the antibody affinity to the antigen. For this purpose, a high-density goat α human antibody surface over a CM5 Biacore™ chip was prepared using routine amine coupling on a Biacore 2000™ instrument. mAb 731 was diluted to 4.7 μg/mL and mAb 623 to 5.2 μg/mL in degassed HBS-P (Hepes buffered saline containing 0.005% polysorbate 20) running buffer containing 100 μg/ml BSA. A capture protocol was developed for both mAbs. Before each antigen sample injection, each mAb was captured over a different flow cell for 30 seconds at a 10 μL/min flow rate. A, four minute, wash step at 100 μL/min followed to stabilize the mAb baseline. Human IL-13 variant was injected (Peprotech, Inc.) for 90 seconds at a concentration range of 23.6-0.185 nM (2× serial dilution) followed by a 15 minute dissociation. The IL-13 variant samples were prepared in HBS-P containing 100 μg/mL. All samples were randomly injected in triplicate with several buffer injections interspersed for double referencing. The high-density goat α human antibody surfaces were regenerated with one 15 second pulse of 146 mM phosphoric acid (pH 1.5) after each cycle. A flow rate of 100 μL/min was used for all variant IL-13 injection cycles. The sensorgram data were processed using Scrubber 1.1 g and were fit in Clamp 2000 to a 1:1 interaction model with the inclusion of a term for mass transport. The resulting binding constants are listed in Table 21. The data sets for both mAbs were of high quality showing high reproducibility. A 1:1 interaction model described both IL-13/mAb complexes adequately.

TABLE 21

| Sample | R$_{max}$ | k$_a$ (M$^{-1}$s$^{-1}$) | k$_d$ (s$^{-1}$) | K$_D$ (pM) |
|---|---|---|---|---|
| 731 | 45 | 5.11 × 10$^6$ | 5.02 × 10$^{-5}$ | 9.8 |
| 623 | 26 | 5.62 × 10$^6$ | 2.18 × 10$^{-4}$ | 38.8 |

Example 14

Inhibition of IL-13 and IL13Q110R Variant Induced Eotaxin Production

This example presents additional data regarding the ability of the antibodies to inhibit the variants of IL-13 and to inhibit eotaxin production. Anti-IL-13 antibodies were tested for their ability to inhibit eotaxin production in HDFa cells, a primary human dermal fibroblast cell line that expresses IL-13Rα1, IL-13Rα2 and IL-4Rα. The cells were seeded overnight at 4000 cells/well in 96 well plates. Separately, IL-13 or IL-13Q110R was pre-incubated for an hour at 37° C. at 300 pM with or without anti-IL-13 antibodies at an initial concentration of 10 nM. The IL-13 or IL-13Q110R and antibody mixture was then added to the cells treated with 50 ng/mL TNFα and incubated for 2 days at 37° C. At this point the supernatants were collected and analyzed for the presence of eotaxin using a quantitative ELISA. The experiments were conducted two or three times with triplicate data points. The results are presented in Table 22 below. Also included are IC$_{50}$'s for IL-13 measured in this assay. FIGS. 11A-D show the percent inhibition of the eotaxin release induced by IL-13 or IL-13Q110R variant by recombinant antibodies 623 and 731 compared to an isotype matched control, e.g., an IgG2 control monoclonal antibody.

TABLE 22

| | IC50 (pM) | | | |
|---|---|---|---|---|
| | 300 pM IL-13 | 300 pM IL-13Q110R | 600 pM IL-13 | 600 pM IL-13Q130R |
| 623 | 56 | 106 | 113 | 277 |
| 731 | 28 | 54 | 56 | 140 |

Example 15

Neutralization of IL-13 Bioactivity In Vitro by 623 and 731

Figure 12:
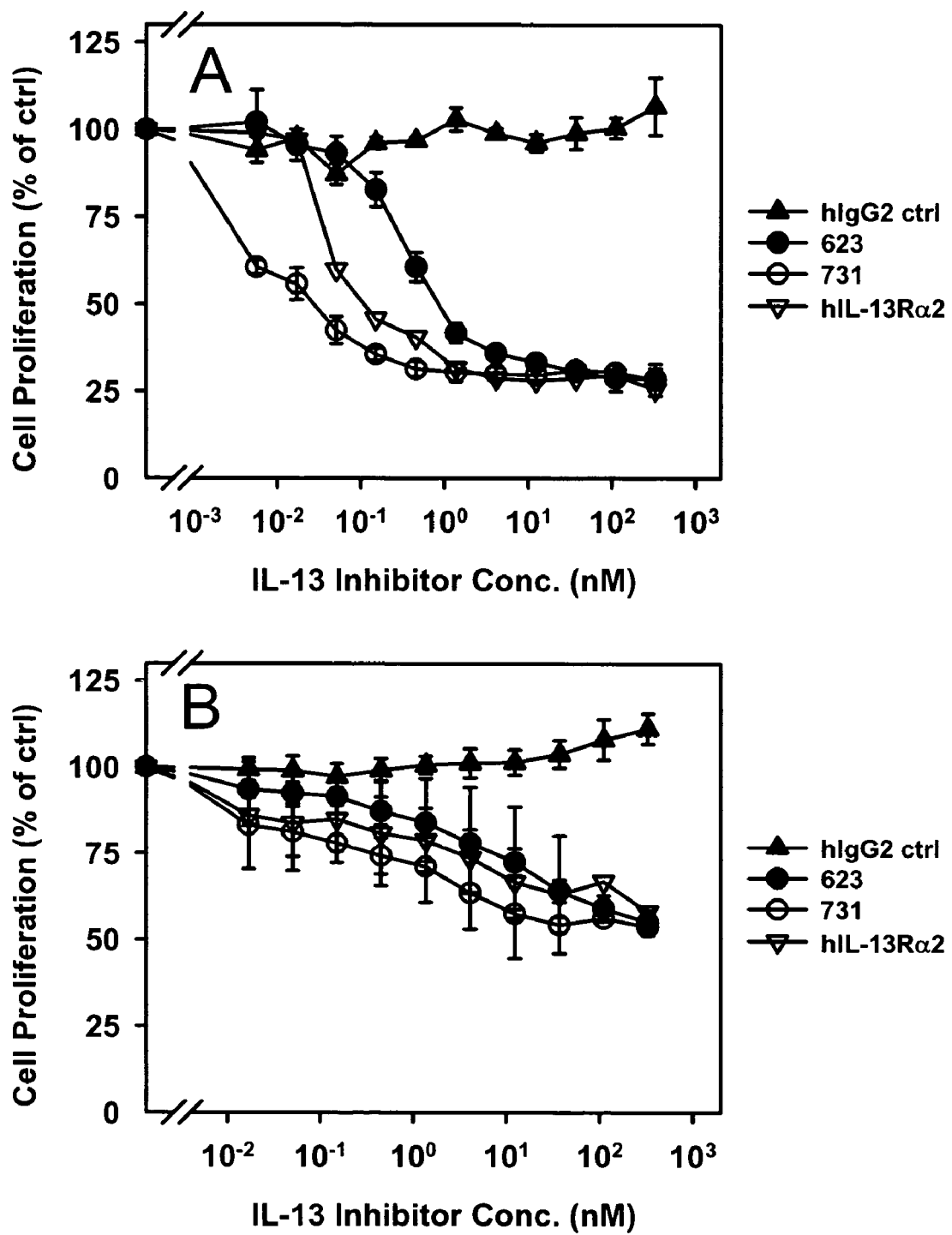
FIGS. 12A and 12B are graphs demonstrating inhibition of L-1236 (A) and HDLM-2 (B) cell line proliferation by 623 and 731. mAb 623, mAb 731 or isotype matched control were added to the plate for final concentrations of 0.017 to 330 nM (titrated 1:3).

This example demonstrates the ability of the antibodies to inhibit of HDLM-2 and L-1236 cell proliferation, two IL-13-responsive Hodgkin's lymphoma-derived cell lines. It has been shown that these cell lines not only secrete IL-13 but also use this cytokine as a growth factor, possibly by an autocrine or paracrine mechanism (Trieu et al., Claudio J O et al., Soluble interleukin-13Ralpha2 decoy receptor inhibits Hodgkin's lymphoma growth in vitro and in vivo, *Cancer Res*, 64:3271-3275 (2004)). After 72 hours of incubation with the relevant compound, cell proliferation was assessed by 3H-thymidine incorporation. Percent cell proliferation in the presence of inhibitor was calculated compared to cells alone control wells (100% production). Values were plotted as IL-13 inhibitor concentration (nM) vs percent cell proliferation. Data represent the average of five (L-1236 assay) and four (HDLM-2 assay) experiments. IL-13 neutralization by mAb 623 and mAb 731 resulted in a dose-dependent inhibition of proliferation of both cell lines (FIG. 12A and FIG. 12B). mAb 623 had EC$_{50}$s of 390 pM in the L-1236 proliferation assay (FIG. 12A) and 4.5 nM in the HDLM-2 proliferation assay (FIG. 12B). 731 had EC$_{50}$s of 5.2 pM in the L-1236 proliferation assay (FIG. 12A) and 0.18 nM in the HDLM-2 proliferation assay (FIG. 12B). hIL-13Rα2/Fc had EC$_{50}$s of 59 pM in the L-1236 proliferation assay (FIG. 12A) and 0.6 nM in the HDLM-2 proliferation assay (FIG. 12B).

The levels of IL-13 measured in the supernatant of HDLM-2 and L-1236 cells were 2.6 ng/ml and 118 pg/ml respectively.

Example 16

Inhibition of IL-13-Induced CD23 Expression in B Lymphocytes

IL-13 has been shown to induce CD23 up-regulation in B lymphocytes (Punnonen et al., Interleukin 13 induces interleukin 4-independent IgG4 and IgE synthesis and CD23 expression by human B cells, *Proc Natl Acad Sci USA*, 90:3730-3734 (1993)). This Example demonstrates mAb 623 and mAb 731's ability to inhibit IL-13-induced expression of CD23 on B lymphocytes in whole blood. Increasing concentrations of mAb 623, mAb 731 or isotype control were added to human whole blood in the presence of recombinant human IL-13 (10 ng/ml). After 24 hrs at 37° C., B-cells were immunostained using anti-CD19 and anti-CD23 antibodies and analyzed by FACS. Results (FIG. 13) were expressed as Geometric Mean expression of surface CD23 on CD19$^+$ cells compared to control wells containing IL-13 alone. Data represent the average of four (hIL-13Rα2/Fc), six (731) and eleven (623 and hIgG2) donors.

Figure 13:
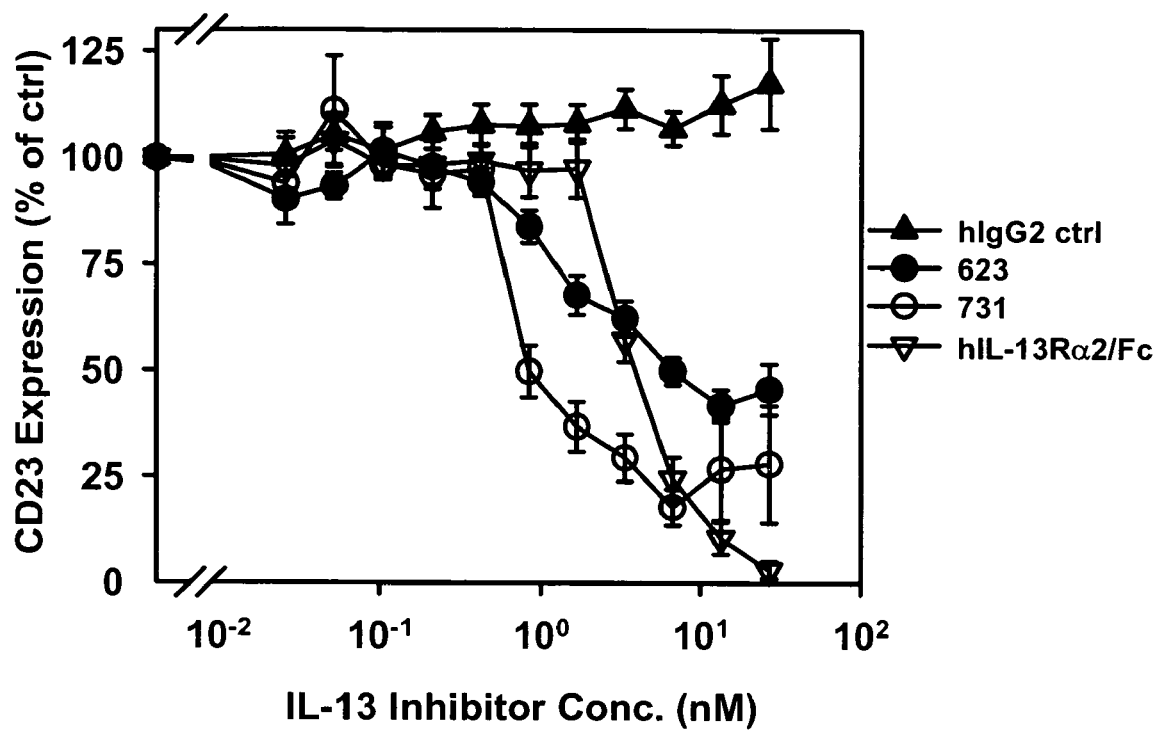
FIG. 13 is a graph displaying the impact of mAb 623 and 731 and hIL-13Ralpha2Fc on CD23 expression on whole blood B cells.

IL-13 neutralization by mAb 623 and mAb 731 resulted in a dose-dependent inhibition of CD23 expression with an IC$_{50}$ of 6.2 nM and 0.87 nM respectively. hIL-13Rα2/Fc had an IC$_{50}$ of 4.0 nM (FIG. 13).

Example 17

Additional Testing of MAB 623 and 731 in Asthma Models

As noted above, since mAb 623 and mAb 731 do not cross-react with murine IL-13, humanized IL-13 mice were generated from 129×C57BL/6 mice by the genetic disruption of the murine IL-13 gene through the introduction of the cDNA encoding the human IL-13 gene (Lexicon, The Woodland, Tex.).

Additional Ovalbumin (OVA)-Induced Asthma in IL-13 Humanized Mice: Prophylactic Studies MAB 623 and MAB 731 Fixed Dose Prophylactic OVA Study This experiment was performed in a manner similar to Example 3 above, using the 24 days protocol. The samples were examined for the effectiveness of the antibodies on reducing OVA-induced mucus production in the airways. Thus, the example demonstrates the effectiveness of the antibodies in treating asthma and similar IL-13 related disorders.

Figure 14:
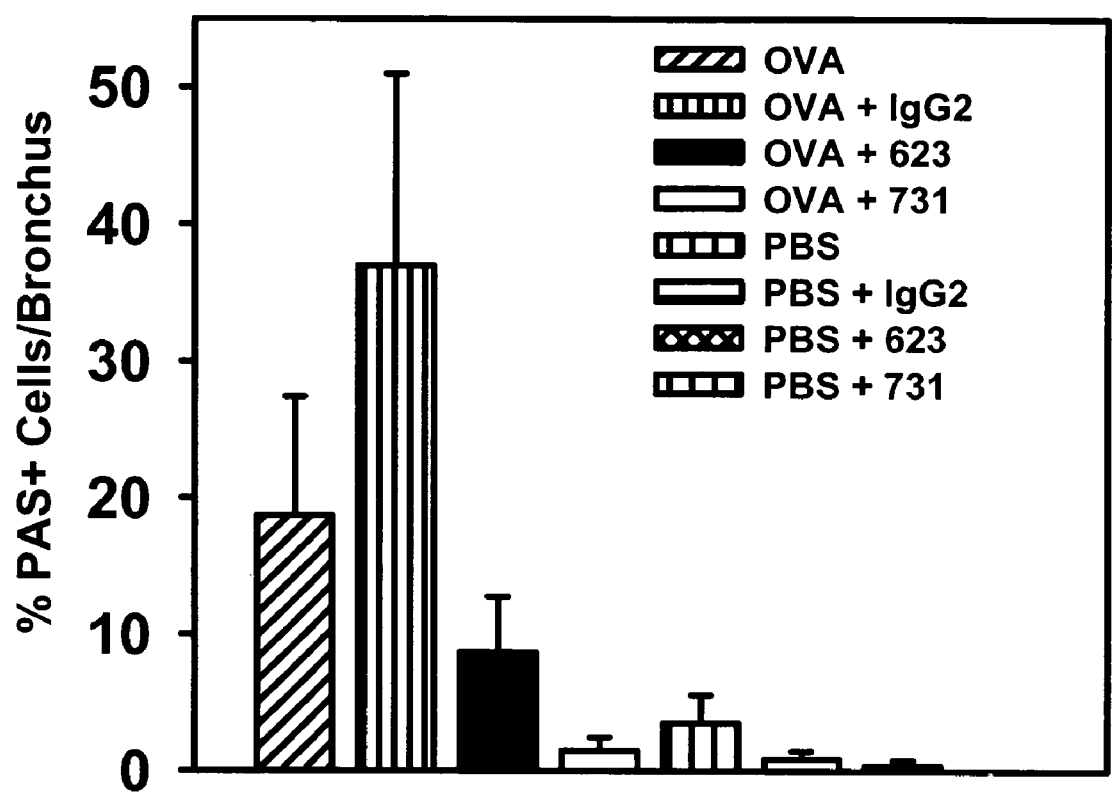
FIG. 14 is a graph displaying the inhibition of OVA-Induced mucus production by mAb 623 and mAb 731 in IL-13 humanized mice.

To examine the effect of mAb 623 and mAb 731 on mucus content of the airway epithelium, lungs slides were stained with hematoxylin and eosin plus Periodic acid-Schiff (PAS). Lung sections (one section per animal) were examined at 20×magnification. Five fields in each section were selected randomly. In each field, the percentage of PAS-positive goblet cells in each brochus was counted. Data are expressed as the average percentage of PAS-positive goblet cells/bronchus. Data are mean±SE (shown in FIG. 14). In the control groups the number of goblet cells containing mucus per bronchus is less than 4%. OVA challenge increased the number of mucus-containing cells in the bronchi to 19% in the OVA group and to 37% in the OVA+IgG2 group. As can be observed in the figure, treatment with mAb 623 reduced the percent of mucus-containing cells in the bronchi to 9%. Treatment with mAb 731 reduced the percent of mucus-containing cells in the bronchi to 2%.

Figure 15:
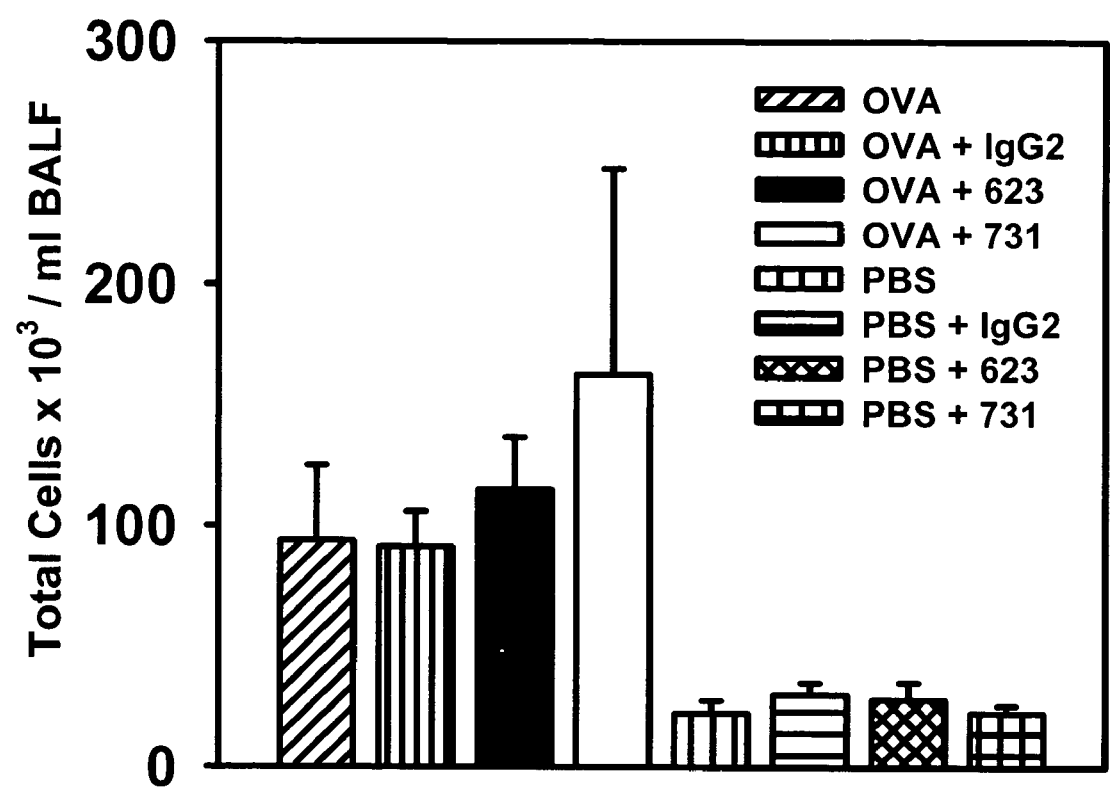
FIG. 15 is a graph displaying an experiment in which treatment with mAb 623 or 731 had little observable effect on OVA-induced leukocyte recruitment in BALF.

To further examine the effect of mAB 623 and mAb 731 on the leukocyte recruitment in the airways, after the AHR measurements (Example 3), mice were sacrificed and bronchoalveolar lavage fluid (BALF) was collected by flushing the lungs two times with 1 ml of PBS. Cell counts were determined by light microscopic evaluation of cytospin preparations. Data are mean±SE and are shown in FIG. 15. Treatment with 623 or 731 had no noticeable effect on OVA-induced leukocyte recruitment in BALF.

MAB 623 And MAB 731 Prophylactic Dose Response OVA.

Figure 16:
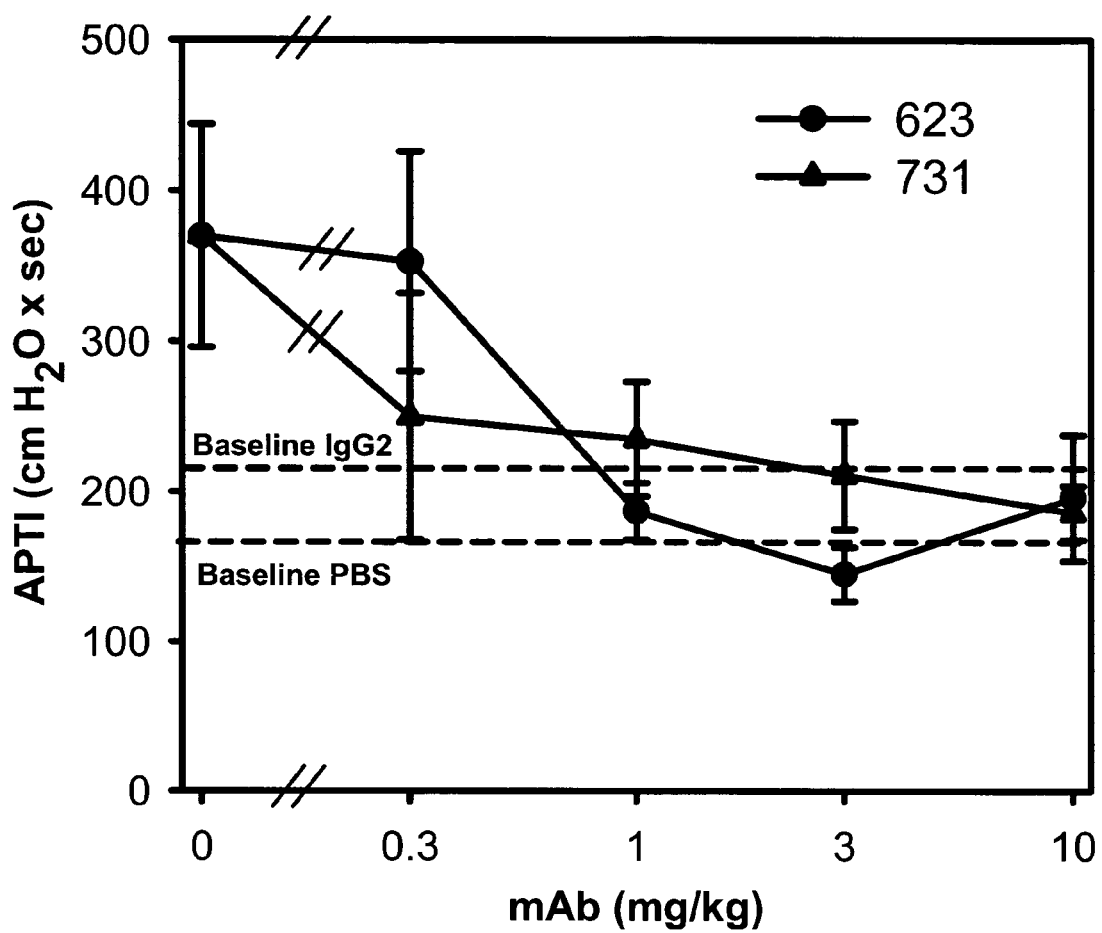
FIG. 16 is graph displaying the inhibition of OVA-induced AHR by 623 and 731 in IL-13 humanized mice in a dosage responsive manner.

This example demonstrates the dose dependency of the inhibitory effect of mAb 623 and mAb 731 on OVA-induced AHR, mucus production and leukocyte recruitment in the BALF. Mice were immunized according the 24 day protocol described above in Example 3 (used for obtaining the data for FIG. 8). On days 13 and 20 either mAb 623 or mAb 731 were administered ip at the doses of 0.3, 1, 3 or 10 mg/kg. Control mice received PBS or an irrelevant IgG2 (10 mg/kg) as isotype control. APTI was determined as described above (for FIG. 8). n=4 mice/group in the PBS, and OVA groups; n=6 mice/group in the PBS+IgG2, and OVA+IgG2 groups; n=7 mice/group in the OVA+623 (3 mg/kg), and OVA+731 (0.3 mg/kg) groups; n=8 mice/group in the OVA+623 (10 mg/kg), OVA+623 (1 mg/kg), OVA+623 (0.3 mg/kg), OVA+731 (10 mg/kg), OVA+731 (3 mg/kg), and OVA+731 (1 mg/kg) groups. Data are mean±SE. At the dose of 0.3 mg/kg neither 623 nor 731 inhibited OVA-induced AHR, whereas doses of 1 mg/kg and higher inhibited AHR to acetylcholine to baseline (PBS) (see, FIG. 16).

Figure 17:
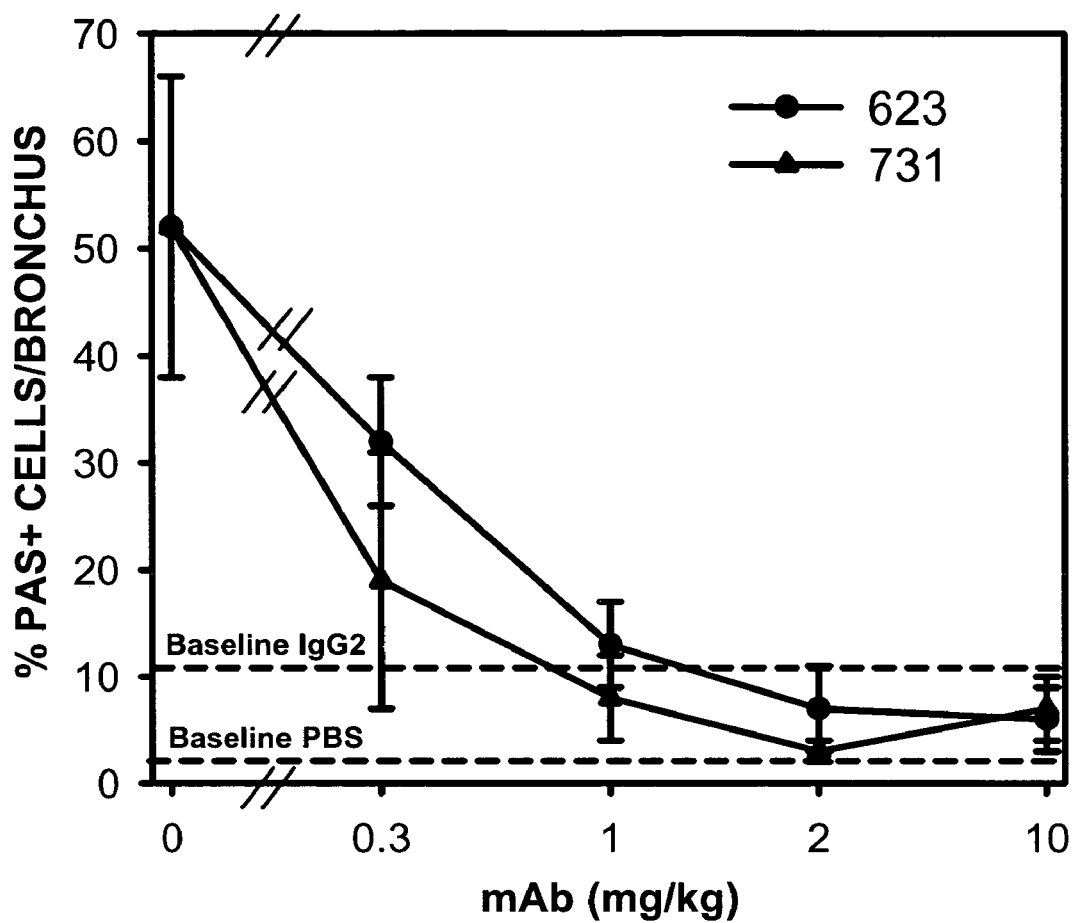
FIG. 17 is a graph displaying inhibition of OVA-induced mucus production by 623 and 731 in IL-13 humanized mice in a dosage responsive manner.

This section of the example further demonstrates the dose dependency of the inhibitory effect of mAb 623 and mAb 731 on OVA-induced mucus production. Lungs were collected and treated as described above (for FIG. 14). Data are expressed as the average percentage of PAS-positive goblet cells/bronchus. Data are mean±SE. Both mAb 623 and mAb 731 showed a similar dose dependent inhibition of the % of PAS+ cells in the airways of OVA treated mice (FIG. 17).

Figure 18:
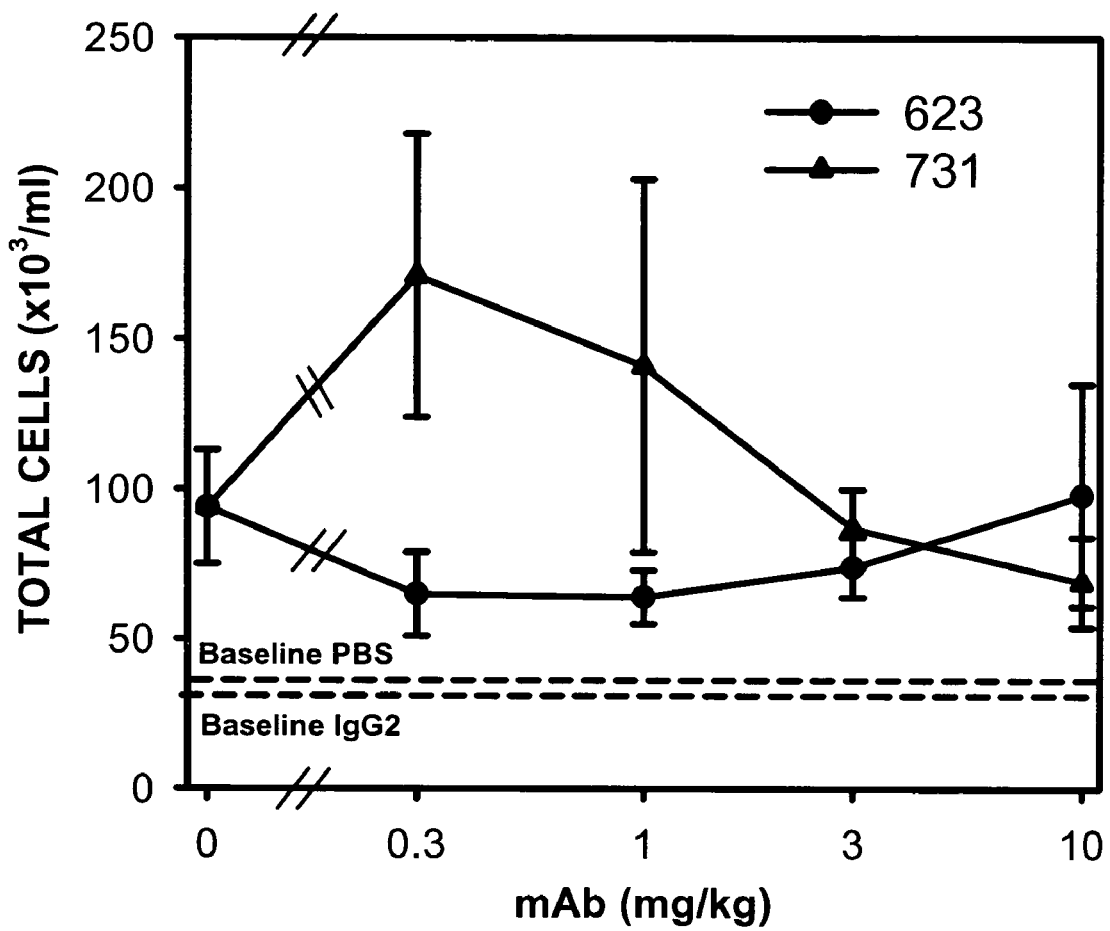
FIG. 18 is a graph displaying an effect of 623 and 731 on OVA-induced leukocyte infiltration in the BALF of IL-13 humanized mice in a dosage responsive manner.

This section of the example further demonstrates that mAb 623 and mAb 731 did not inhibit OVA-induced leukocyte recruitment in BALF at any of the doses tested (FIG. 18). BALF was collected and cell counts were performed as described above (in reference to FIG. 15). Data are mean±SE.

In this experiment the isotype control IgG2 tested at the dose of 10 mg/kg inhibited OVA-induced AHR by 85%. On the other hand the isotype control IgG2 had no effect on mucus hyperplasia and caused an apparent increase in the number of leukocyte in BALF compared to the OVA group by 146%. Thus, some variability in the effectiveness of the antibodies is to be expected and overcoming this variability will be routine in light of the present teachings and the knowledge of one of skill in the art. The results indicate that elevated levels of the antibodies can be required to observe the particular phenotype of inhibition of OVA-induced leukocyte recruitment in BALF.

Example 18

House Dust Mite (HDM)-Induced Asthma in IL-13 Humanized Mice: Prophylactic and Therapeutic Studies MAB 623 And MAB 731 Dose Response Prophylactic HDM Example.

The major allergen in house dust comes from mites. This Example uses a clinically relevant and representative allergen for an asthma model. One of skill in the art would consider this example and its results to be representative of the effectiveness of the antibodies in other organisms, including humans.

Figure 19:
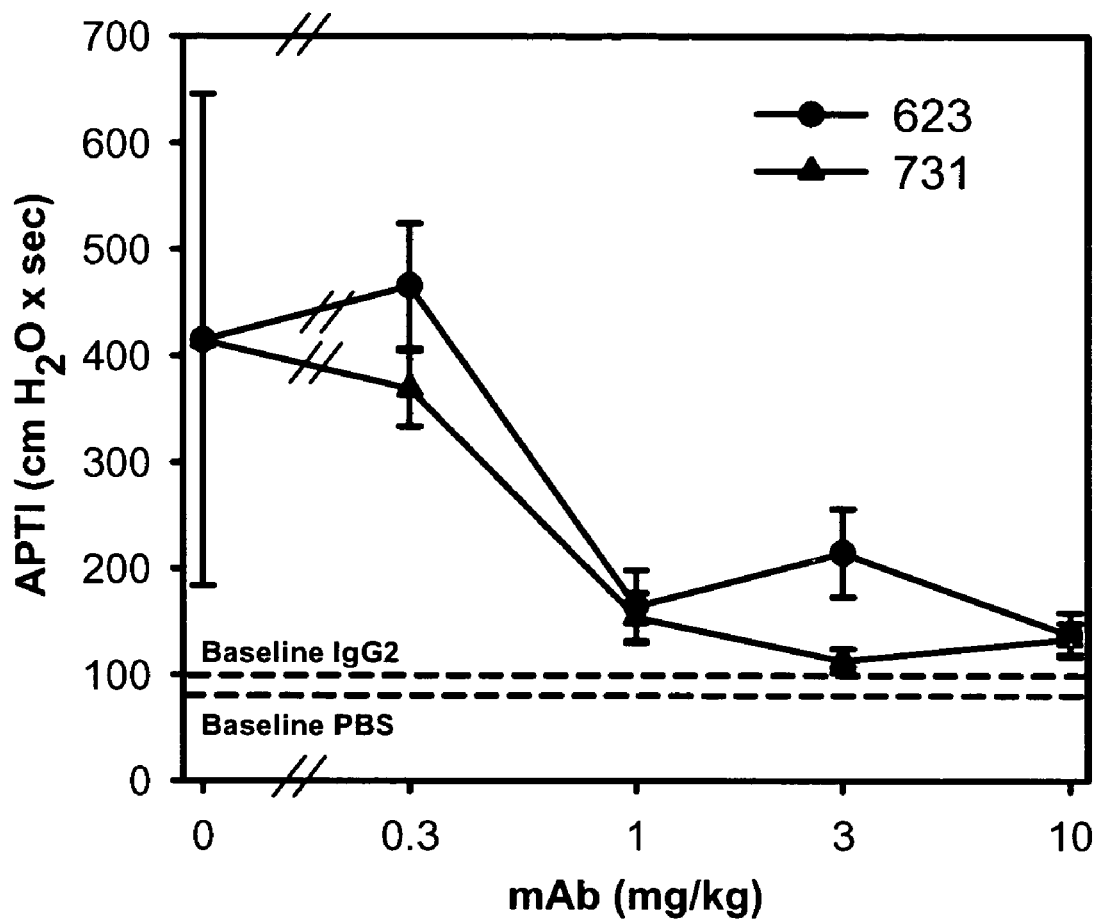
FIG. 19 is a graph displaying a dose response inhibition of HDM-Induced AHR by 623 and 731 Dose Response in IL-13 humanized mice.

On days 1, 7 and 14 mice were challenged with three intratracheal administrations of HDM (100 μg) in 50 μl of PBS. On days −1, 6 and 13 either 623 or 731 were administered intraperitoneally at the doses of 10, 3, 1, 0.3 mg/kg. Control mice received PBS or an irrelevant (e.g., negative control) IgG2 as isotype control at the dose of 10 mg/kg. On day 17 mice airway reactivity to the intravenous administration of acetylcholine was measured as described above (FIG. 8). n=2 mice/group in the PBS group; n=3 mice/group in the HDM, HDM+IgG2 groups; n=4 mice/group in the PBS+IgG2 group; n=6 mice/group in the HDM+731 (10 mg/kg), and HDM+731 (0.3 mg/kg) groups; n=8 mice/group in the HDM+623 (10 mg/kg), HDM+623 (3 mg/kg), OVA+623 (1 mg/kg), HDM+623 (0.3 mg/kg), HDM+731 (3 mg/kg), and HDM+731 (1 mg/kg) groups. Data are mean±SE. The results are shown in FIG. 19. At the dose of 0.3 mg/kg 623 and 731 had no effect on HDM-induced AHR, whereas doses of 1 mg/kg and higher inhibited AHR to baseline levels (FIG. 19). Due to the small number of animals in the HDM and HDM+IgG2 groups, AHR measured in these groups was very variable (APTI 579+463 and 415+213 in the HDM and HDM+IgG2 groups respectively). At the dose of 10 mg/kg mAb 623 reduced the percent of $PAS^+$ cells in the lung of mice challenged with HDM to baseline (PBS group).

Figure 20:
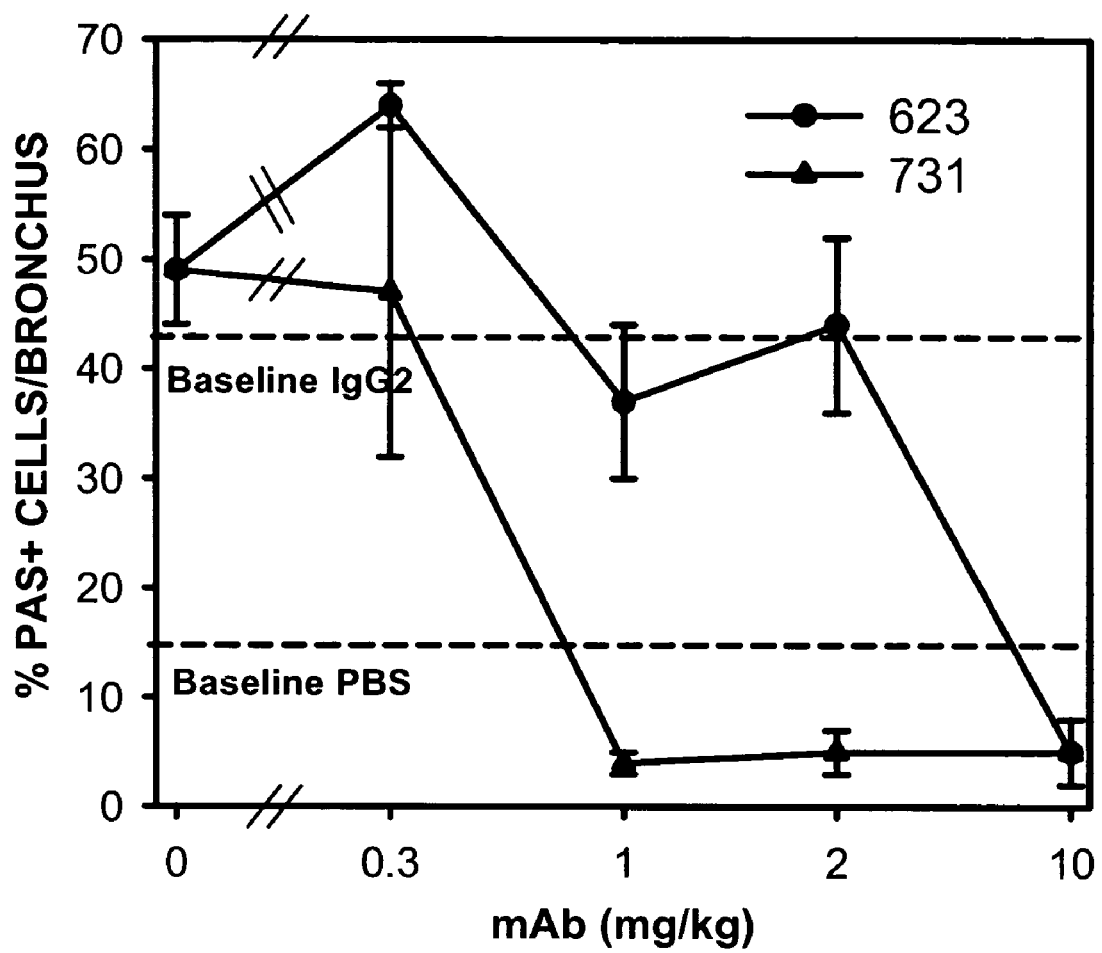
FIG. 20 is a graph displaying a dose response inhibition of HDM-induced mucus production by 623 and 731 in IL-13 humanized mice.

In a similar fashion to that described above, dose responsiveness of the inhibition of HDM-induced mucus production by mAb 623 mAb 731 in IL-13 humanized mice was examined. Lungs were collected and treated as described in reference to FIG. 14 and were examined. Data are expressed as the average percentage of PAS-positive goblet cells/bronchus. Data are mean±SE. At the dose of 10/mg/kg mAb 623 reduced the % of PAS+ cells to baseline, whereas lower doses were not as effective. At the dose of 0.3 mg/kg mAb 731 had no effect on the percent of PAS+ cells, but at higher doses it reduced the percent PAS+ cells to baseline levels (PBS group) (FIG. 20).

Figure 21:
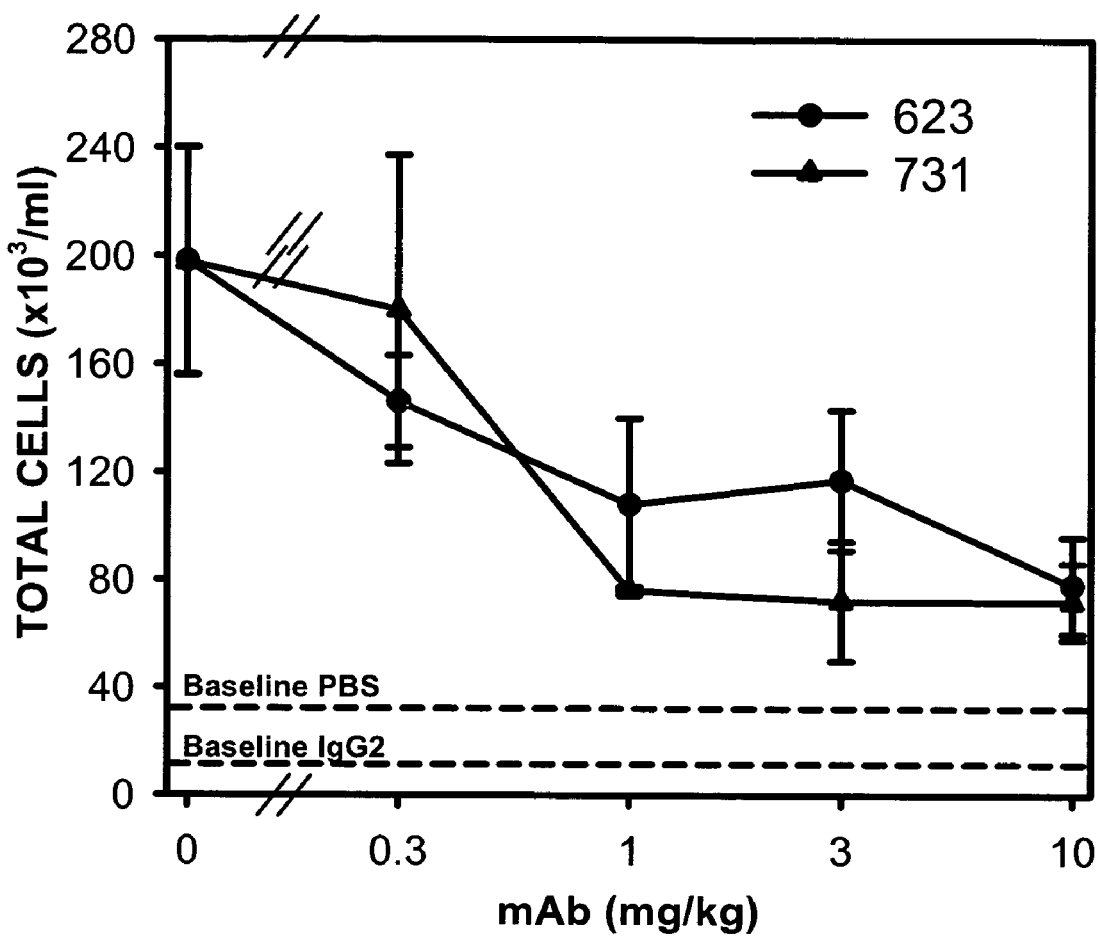
FIG. 21 is a graph displaying a dose response inhibition of 623 and 731 on HDM-induced leukocyte infiltration in the BALF of IL-13 humanized mice.

In a similar fashion to the experiments described above, mAb 623 and mAb 731 were tested and determined to inhibit HDM-induced leukocyte recruitment in a dose dependent manner, starting at the dose of 1 mg/kg (see FIG. 21). BALF was collected and cell counts were performed as described in relation to the data for FIG. 15. Data are mean±SE. The isotype control caused an apparent increase in the number of leukocytes recruited by HDM in the BALF (497±156 compared to 198±42 $10^3$ cells/ml BALF in the HDM+IgG2 and HDM group respectively).

MAB 623 Fixed Dose Therapeutic and Prophylactic HDM Study.

This Example demonstrates the effectiveness of mAb 623 as a therapeutic and prophylactic in the HDM model. In this example, mAb 623 was administered at the fixed dose of 100 μg/mouse according to 3 different schedules: i) one day before each HDM challenges (prophylactic treatment); ii) one day before the last HDM challenge and iii) at the same day of the last HDM challenge (therapeutic treatments). The allergic phenotype was assessed 3 days after the last HDM challenge. Thus, the timing of the administration of the antibody, and the resulting effectiveness, were determined. In alternative embodiments, this approach can be applied for the other antibodies.

Figure 22:
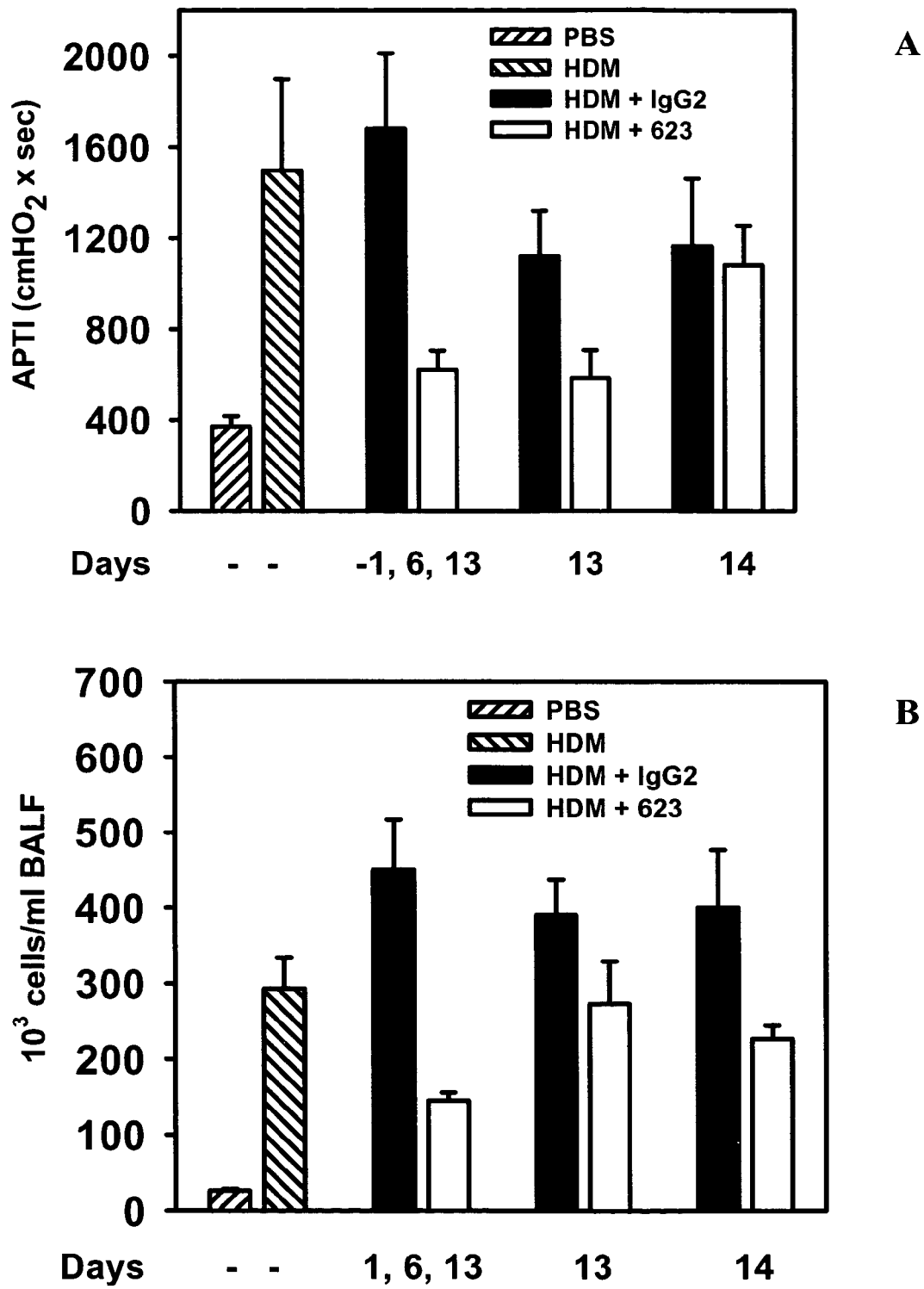
FIGS. 22A and 22B are graphs depicting the effect of prophylactic and therapeutic 623 administration on HDM-induced AHR and leukocyte infiltration in the BALF of IL-13 humanized mice.

Mice were challenged with three intratracheal administrations of HDM (100 μg) in 50 μl of PBS at day 1, 7 and 14. 623 or an IgG2 isotype control were administered intraperitoneally at the dose of 100 μg/mouse according to 3 different schedules: on day −1, 6 and 13 (prophylactic treatment), on day 13 or on day 14 (therapeutic treatment). Control mice received PBS or an irrelevant IgG2 as isotype control. On day 17 airway reactivity to the intravenous administration of acetylcholine and leukocyte infiltration in BALF were measured as described above (in reference to FIG. 8 and FIG. 15). n=8 mice/group in the PBS, HDM, HDM+IgG2 (day −1, 6 and 13), HDM+IgG2 (day 13), HDM+IgG2 (day 14), HDM+623 (day 13), groups; n=10 in the HDM+623 (day −1, 6 and 13), HDM+623 (day 14) groups. Data are mean±SE. As shown in FIG. 22A, when administered prophylactically before each HDM challenge, mAb 623 completely inhibited HDM-induced AHR. Furthermore, 623 completely inhibited HDM-induced AHR when therapeutically administered the day before the last HDM challenge. In contrast, the therapeutic administration on the same day of the last challenge had little effect on AHR (FIG. 22A). mAb 623 inhibited leukocyte recruitment in BALF when administered prophylactically before each HDM challenge (FIG. 22B).

As will be appreciated by one of skill in the art, the examples used for characterizing these antibodies can readily be applied to any antibody to IL-13 and variant thereof. Thus, the examples represent how one of skill in the art could readily and routinely determine whether an antibody, or a variant of an antibody disclosed herein, could function in altering IL-13 activity.

As will be appreciated by one of skill in the art, while the above results frequently focuse upon the prophylactic aspects of the antibodies, the above methods and results are extendable to methods for treatment as a therapy. For example, once a subject has been identified that is suffering from an IL-13 related disorder, an effective amount of the antibody can be administered. As will be appreciated by one of skill in the art, additional amounts of the antibody can be required compared to the amount for a prophylactic use. For example, the amount in addition can be 1-10, 10-100, 100-1000 fold or more above the amounts for prevention, described above. This can be required where the disorder results in large amounts of IL-13 or when large amounts of IL-13 have to be removed in order to reduce the symptoms of the disorder. In alternative situations, lower amounts of the antibody can be required to treat a subject with an IL-13 related disorder than to prevent the disorder. For example, in situations in which a single dose of the antibody is sufficient to bind and remove substantially all of the excess IL-13, whereas, to prevent the disorder, a similar amount, but an amount administered continuously, may have to be administered. Additionally, the amount can be administered in various ways, for example an i.v., and the amount can be administered continuously, if desired. The above results are fully consistent with and suggestive of the fact that the antibodies will work as a therapeutic as well as a prophylactic. As will be appreciated by one of skill in the art, multiple and/or continuous doses, e.g., treatment for the life of the subject, may be required in some situations.

Additionally, as will be appreciated by one of skill in the art, the nature of the particular host can also influence the manner and amount of treatment. For example, in subjects that are chronic (naturally sensitive to the compound and need not be sensitized to it) for a disorder (e.g., asthma) additional amounts, given by more efficient means (e.g. i.v. instead of s.c.) over a longer period of time would be expected to have a higher likelihood of working, in light of the above results and the knowledge of one of skill in the art. For example, while the above models and doses can be representative of acute models of infection, the above doses can be insufficient when administered as described above, in one form of chronic model (e.g., in monkeys that had been exposed to various agents over prolonged periods of time). This result is consistent with what one of skill in the art would expect as elevated levels of IL-13 would logically require additional amounts of the antibody. Furthermore, one of skill in the art would expect that, given larger doses of the antibody, administered frequently enough, that the same or similar results, as described above, would result. Applicants note that this is consistent with the results shown in PCT publication No. WO 2005/007699, which demonstrates that while low levels of antibodies to IL-13 were not substantially effective in monkey models, that higher levels did result in significant and predicted results. As noted above, one method by which the levels of antibody required (for any IL-13 depend disorder) can be determined is through the monitoring of the levels of biomarkers in the subject. Examples of these biomarkers are described herein.

Example 19

Characterization of IL-13 Dependent Biomarkers: Effect of MAB 623 ON Serum Levels of TARC, Eotaxin and C10 in the OVA-induced Asthma Model in IL-13 Humanized Mice This Example demonstrates and verifies serum IL-13-dependent biomarkers that can be used in the clinical setting. The serum levels of OVA-induced TARC, C10 and eotaxin were measured in mice and the effect of IL-13 inhibition on those levels were studied. (IL-13 has been shown to induce the release of TARC, C10, and eotaxin (see, e.g., Ma et al., The C10/CCL6 chemokine and CCR1 play critical roles in the pathogenesis of IL-13-induced inflammation and remodeling, *J Immunol.*, 172(3):1872-81 (2004); Zhu et al., IL-13-induced chemokine responses in the lung: role of CCR2 in the pathogenesis of IL-13-induced inflammation and remodeling, *J Immunol.* 168(6):2953-62 (2002); Nomura et al., Interleukin-13 induces thymus and activation-regulated chemokine (CCL17) in human peripheral blood mononuclear cells, *Cytokin,.* 20(2):49-55 (2002); Zhu et al., Pulmonary expression of interleukin-13 causes inflammation, mucus hypersecretion, subepithelial fibrosis, physiologic abnormalities, and eotaxin production, *J Clin Invest.*, 103(6):779-88 (1999))). As will be appreciated by one of skill in the art, the technique outlined in this approach could be used to identify other markers as well.

An OVA-induced asthma study in A/J wild type mice was first performed to establish the time of serum induction of TARC, eotaxin and C10. On days 1 and 7 mice were immunized with OVA (25 µg OVA in 2 mg Alum, ip) or Alum as control. On days 14, 15 and 17, mice were anesthetized with a mixture of ketamine and xylazine [45 and 8 mg/Kg, respectively] and challenged wit OVA (750 µg in 50 µL, intranasal) or an equivalent volume of PBS as a control. Blood was collected 3, 6 and 24 hours after the final challenge. Serum levels of TARC and eotaxin were measured by ELISA (Duoset, R&D System). Serum levels of C10 were measured by sandwich ELISA. Briefly, serum samples were titrated 1:2 on anti-C10 antibody (R&D System) coated plates for 1 hour. Biotinylated anti-C10 detection antibody (R&D System) was added, followed by an incubation of 1 µg/ml streptavidin-HRP. Captured C10 was determined using a TMB substrate reaction and ng/ml values in each sample were quantitated from a standard curve on the plate. n=6 mice/groups. Data are mean±SE. In the OVA/OVA group serum levels of TARC and eotaxin were increased at 3 and 6 h compared to Alum/PBS group; serum levels of TARC were still elevated at 24 h compared to Alum/PBS group, although to a lesser extent than at 3 and 6 h; serum levels of C10 were increased at 3, 6 and 24 h compared to Alum/PBS group, with maximal induction at 24 h (results shown in FIG. 23, FIG. 24, and FIG. 25).

Next, the ability of prophylactic administration of mAb 623 to inhibit serum levels of TARC, eotaxin and C10 using IL-13 humanized mice was assessed. As will be appreciated by one of skill in the art, this can be used for any of the present antibodies.

Figure 23:
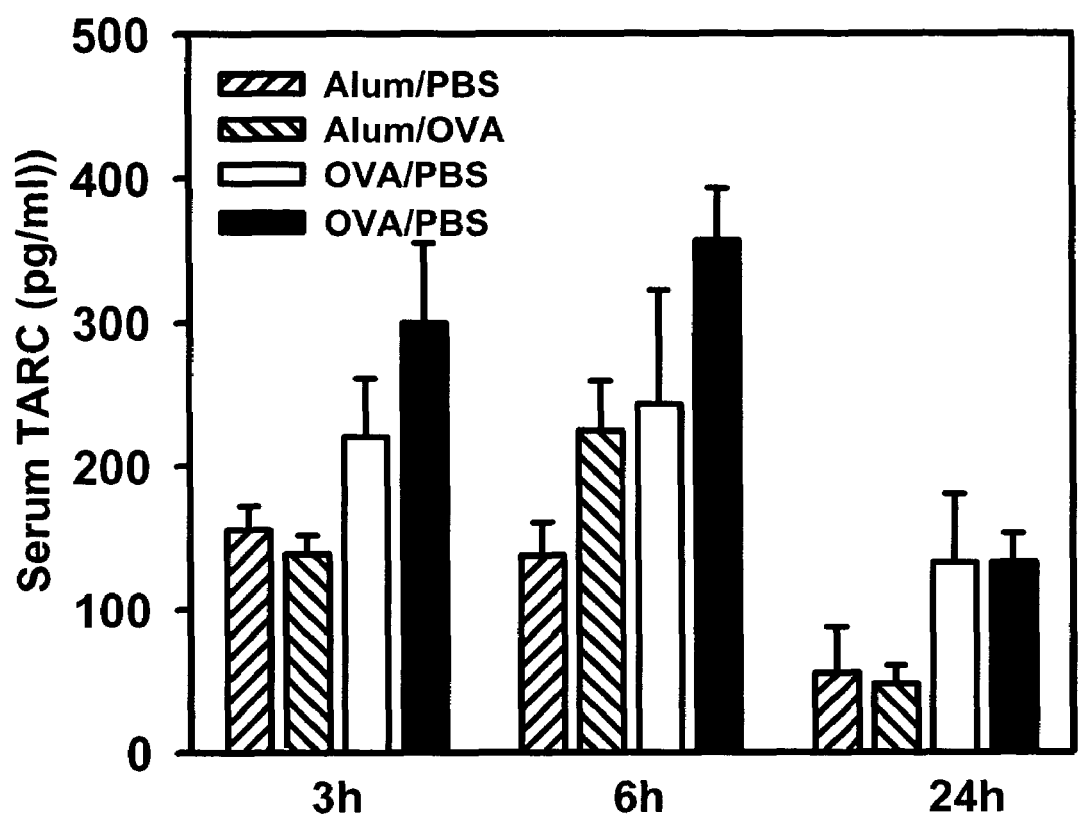
FIG. 23 is a graph depicting OVA-induced serum levels of TARC in wild type mice.
Figure 24:
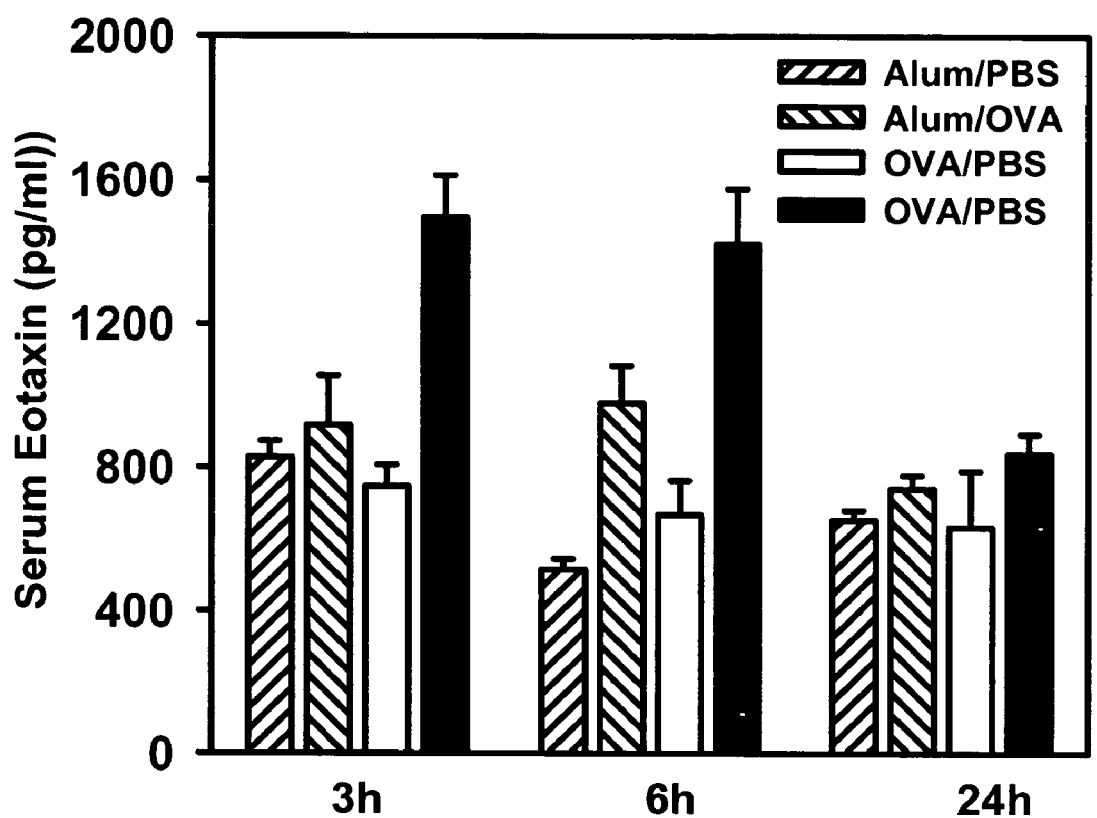
FIG. 24 is a graph depicting OVA-induced serum levels of eotaxin in wild type mice.
Figure 25:
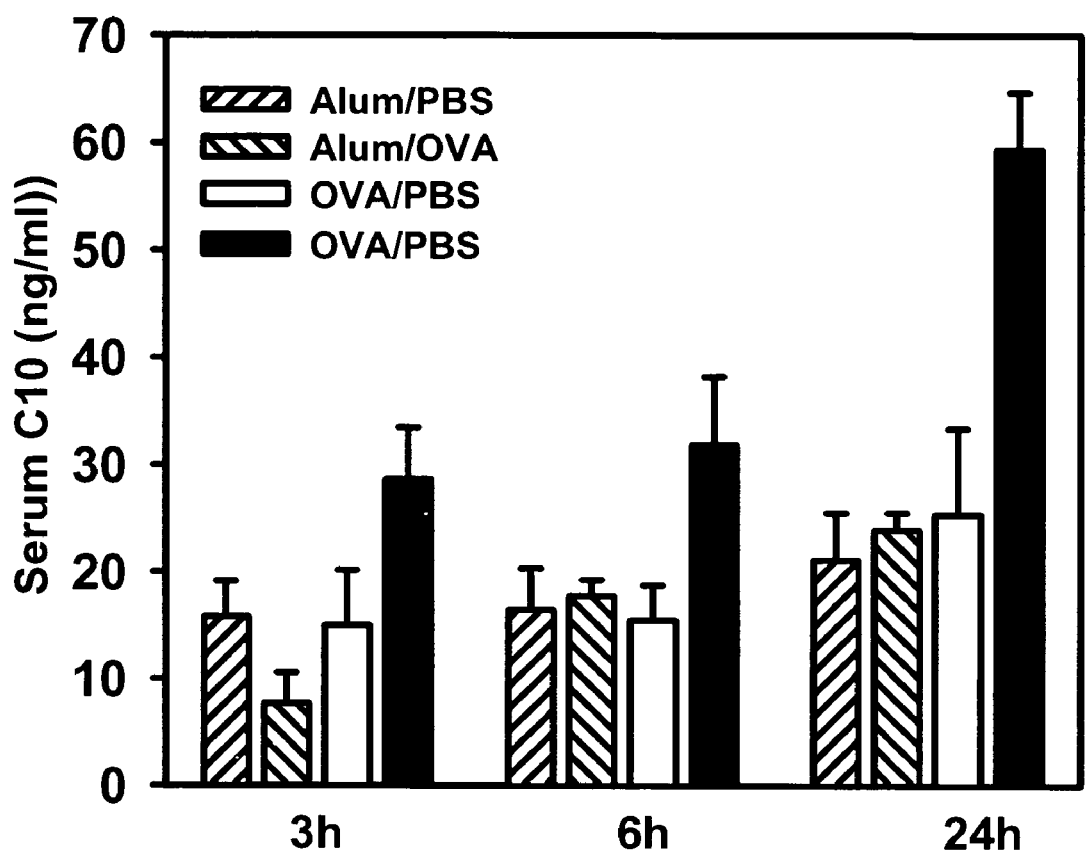
FIG. 25 is a graph depicting OVA-induced serum levels of C10 in wild type mice.
Figure 26:
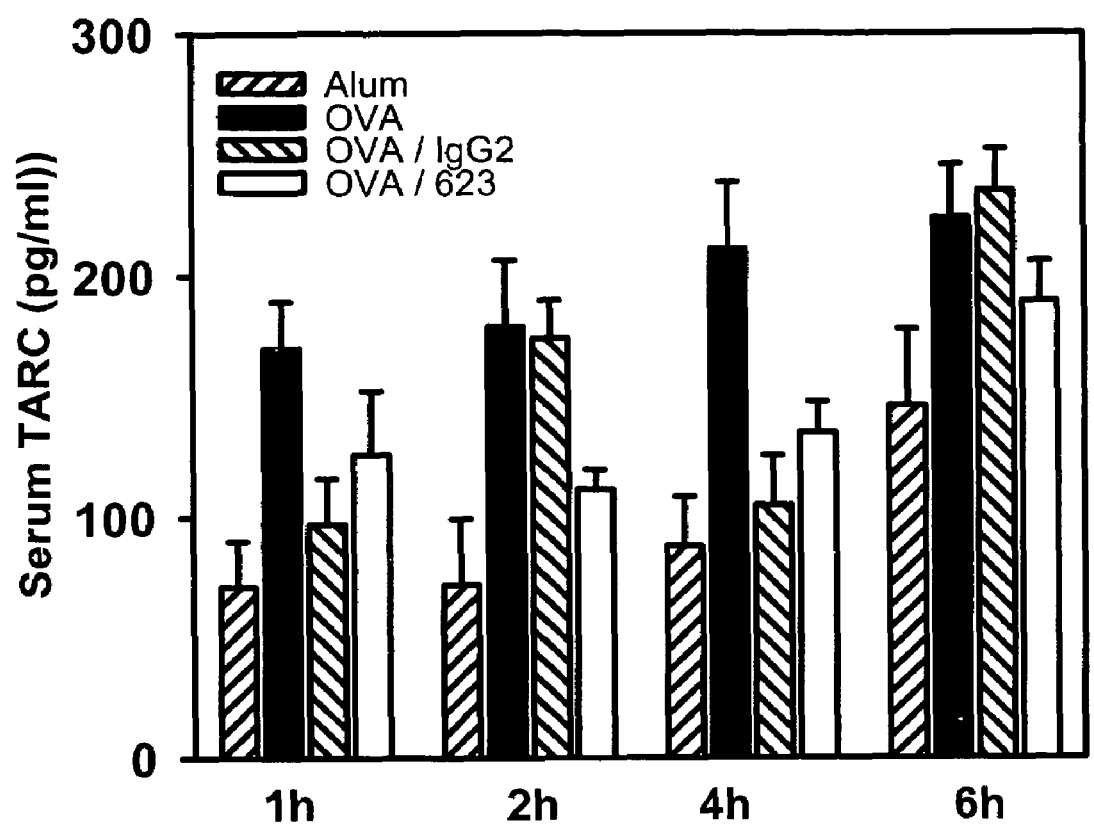
FIG. 26 is a graph depicting mAb 623 inhibition of OVA-induced serum levels of TARC in IL-13 humanized mice.
Figure 27:
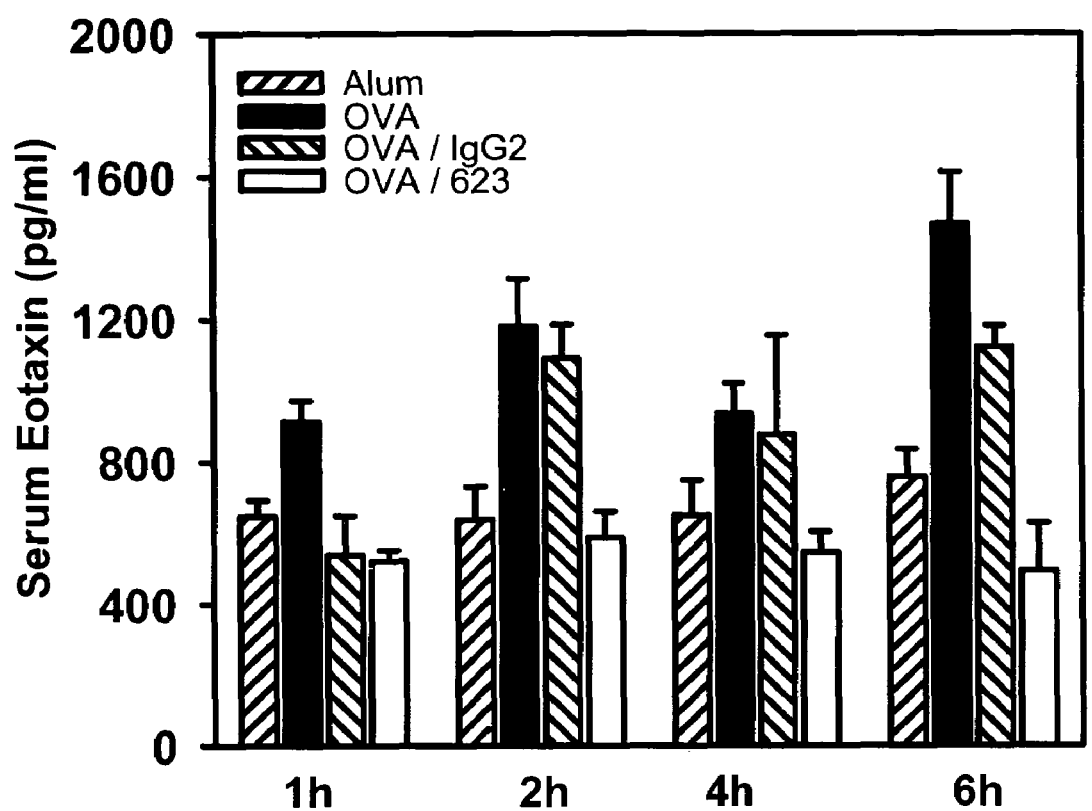
FIG. 27 is a graph depicting mAb 623 inhibition of OVA-induced serum levels of eotaxin in IL-13 humanized mice.

Mice were immunized according to the OVA-induced asthma protocol described in reference to FIG. 23, FIG. 24, and FIG. 25. mAb 623 was administered intraperitoneally at the dose of 100 µg/mouse (5 mg/kg) on days 13, 15 and 17 of the study. Control mice received PBS or an irrelevant IgG2 as isotype control. Blood was collected either at 1 and 4 hours or 2 and 6 hours after the final challenge. Serum TARC levels were measured by ELISA (Duoset Kit, R&D System). n=15 mice/group in the OVA group (n=8 for the 1 and 4 hour group and n=7 for the 2 and 6 hour group); n=14 mice/group in the OVA+IgG2 group (n=7 for the 1 and 4 hour group and n=7 for the 2 and 6 hour group); n=17 mice/group in the OVA+623 group (n=8 for the 1 and 4 hour group and n=9 for the 2 and 6 hour group); n=15 mice/group in the Alum group (n=7 for the 1 and 4 hour group and n=8 for the 2 and 6 hour group); Data are mean±SE.mAb. mAb 623 inhibited the induction of TARC, with a maximum inhibition at the 2 and 4 hours time points (see FIG. 26). Thus TARC appears to be an adequate marker.

To follow the influence on eotaxin, mice were treated as described as discussed above in reference to FIG. 26. Serum eotaxin levels were measured by ELISA (Duoset Kit, R&D System). Data are mean±SE. mAb 623 inhibited eotaxin induction at 1, 2, 4 and 6 hours (see FIG. 27). Thus, eotaxin appears to be an adequate marker.

Figure 28:
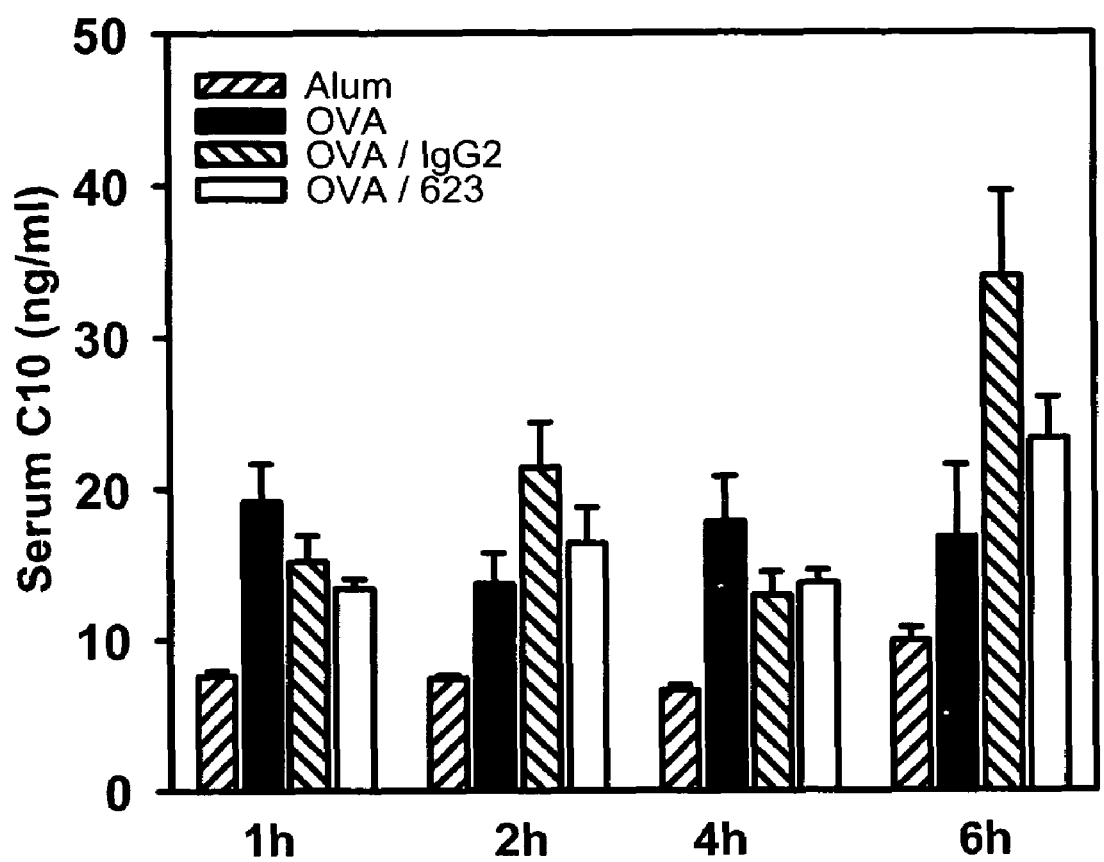
FIG. 28 is a graph depicting mAb the effect of mAb 623 treatment on OVA-induced serum levels of C10 in IL-13 humanized mice.

To follow the influence on C10 levels, mice were treated as described above, in reference to FIG. 26. Serum C10 levels were measured by ELISA as described in reference to FIG. 25. Data are mean±SE. mAb 623 had little visible effect on C10 levels at any of the time points tested (FIG. 28). It is believed that, as C10 has a longer time to peak (e.g., as shown in FIG. 25) and that additional time is likely required to see the impact on C10 from the antibody as a biomarker and for the use of C10 as a biomarker.

Thus, by the above disclosed methods, one of skill in the art will readily be able to identify additional markers that can be of use in following IL-13 related disorders and the treatment thereof.

Example 20

Use of Biomarkers in a Subject Receiving MAB 623 and/or MAB 731

This example outlines how a biomarker, such as one of the ones characterized above, can be used to monitor and adjust the amount or frequency of an antibody that is administered to the subject.

A subject with asthma is identified. The subject is administered a starting amount of mAb 623 and/or 731, e.g., 1-10 mg/kg, every particular time unit. Following this, the eotaxin levels in the subject are measured each hour via ELISA. The amount and/or frequency of the mAb administered is increased until the level of eotaxin is reduced to a level indicative of adequate treatment for the subject. This level can be any significant decrease, for example, any decrease shown in the above experiments or the maximal decrease achievable through the administration of the antibody. Once this decrease is observed the amount and/or frequency of administration of the antibody can be held constant and even decreased, if appropriate. Thus, biomarkers can allow one to determine the optimal amount of antibody needed.

As will be appreciated by one of skill in the art, this example can allow one of skill in the art to determine what a sufficient or therapeutically sufficient amount of the antibody can be for each subject. By administering a starting amount of an antibody, one can increase the amount of the antibody, until the presence of the biomarker begins to decline, thereby identifying a therapeutically sufficient amount or dose for the subject. Additionally, this can also be used to identify how (e.g., subcutaneously, intravenously, etc.) and how frequently (e.g., 1, more than once, a dose per unit of time, continuously, etc.) the antibody should be administered for the desired result. As will be appreciated by one of skill in the art, any of the antibodies could be used on any IL-13 related disorder, especially those listed herein.

Example 21

The Use of Biomarkers as a Diagnostic

This example details how the biomarkers can be used to identify a patient with an IL-13 related disorder. The level of eotaxin, TARC, and/or C10 present in a healthy individual (e.g., subject without an IL-13 related disorder) is identified. Following this, the level of eotaxin, TARC, and/or C10' in other subjects is characterized. Those with elevated levels (compared to the healthy individuals) of eotaxin, TARC, and/or C10 will be those that can be suffering from an IL-13 related disorder. For further confirmation, subjects with elevated levels of eotaxin, TARC, and/or C10 can further have their levels of the other biomarkers compared to the levels of the other biomarker in a healthy subject.

Thus, this example provides one method that allows one of skill in the art to identify a patient with an IL-13 related disorder or disease. Alternatively, the level of IL-13 in a subject or the properties of IL-13 in the subject can be examined and compared to those without an IL-13 related disorder. For example, one of the presently disclosed antibodies can be used as a diagnostic, allowing for one to detect any changes in a subject's available IL-13 and either comparing the detected amount to a health standard control amount, or for a pre illness amount for the individual (e.g., an internal control).

As will be appreciated by one of skill in the art, in some embodiments, every IL-13 related disorders will not necessarily have to be associated with an increase in eotaxin, TARC or C10. Different diseases might have different biomarkers, some subset of the above, and some IL-13 related disorder might not have biomarkers at all.

The above example can be used to help identify an individual suffering from one of the IL-13 related disorders discussed herein. Thus, in some embodiments, the use of the biomarker detectors (e.g., antibodies to the biomarkers) is as a diagnostic. In other embodiments, such as that described in Example 5, the antibodies themselves can be used as a diagnostic tool to identify patients with elevated levels of IL-13.

As the $K_D$ of the antibodies is known, one can determine the amount of IL-13 in a sample via binding of the IL-13 in a sample to the mAb.

Example 22

Determination of IL-13 Related Disorders

This example demonstrates one method by which one can determine whether a disorder is an IL-13 related or dependent disorder. A subject with a candidate disorder is identified. This can be done by randomly selecting a subject from a population. In the alternative, it can be done by selecting a candidate that is demonstrating symptoms that are characteristic of one of the disorders disclosed herein. The subject's eotaxin, TARC, and/or C10 levels are examined. The patient is administered 10 mg/kg of mAb 623 or 731. The subject's eotaxin, TARC, and/or C10 levels are again examined. This can be repeated numerous times. If a decrease in the level of the biomarkers is observed, then the disorder can be characterized as an IL-13 related disorder.

In alternative embodiments, a greater amount of the antibody is used in progressive administrations of the antibody. In alternative embodiments, all three biomarkers are examined and all three must show decreases for the disorder to be characterized as an IL-13 related disorder. In alternative embodiments, one further correlates a decrease in the symptoms of the candidate disorder along with the decrease in the biomarker(s).

As will be appreciated by one of skill in the art, while the present application has outlined numerous antibodies and tested their functionality, one of skill in the art could readily adjust the antibodies by a single amino acid (or several) and obtain a "new" antibody. In order to test such antibody variants, one can repeat any or all of the above disclosed examples to determine if the antibody functions as desired.

As will be appreciated by one of skill in the art, the above examples outline how to achieve certain results with particular antibodies; however, in light of the present teaching, one of skill in the art will readily be able to apply the other antibodies, or other similar antibodies in the above examples and embodiments.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated antibody that specifically binds to IL-13, wherein said isolated antibody comprises both a light chain variable domain and a heavy chain variable domain and wherein said antibody comprises
   a) the light chain of SEQ ID NO:40, or
   b) the heavy chain of SEQ ID NO:38, or
   c) the light chain of SEQ ID NO:40 and the heavy chain of SEQ ID NO:38, or
   d) the light chain CDR1, CDR2, and CDR3 sequences of SEQ ID NO:40 as shown in Table 20 and the heavy chain CDR1, CDR2, and CDR3 sequences of SEQ ID NO:38 as shown in Table 18, or
   e) the light chain of SEQ ID NO:52, or
   f) the heavy chain of SEQ ID NO:50, or
   g) the light chain of SEQ ID NO:52 and the heavy chain of SEQ ID NO: 50, or
   h) the light chain CDR1, CDR2, and CDR3 sequences of SEQ ID NO:52 as shown in Table 20 and the heavy chain CDR1, CDR2, and CDR3 sequences of SEQ ID NO:50 as shown in Table 18.

2. The isolated antibody of claim 1, wherein said antibody is
   a) a human antibody,
   b) a humanized antibody,
   c) a chimeric antibody,
   d) a monoclonal antibody,
   e) a polyclonal antibody,
   f) a recombinant antibody,
   g) an antigen-binding antibody fragment,
   h) an IgD antibody,
   i) an IgE antibody,
   j) an IgG1 antibody,
   k) an IgG2 antibody,
   l) an IgG3 antibody, or
   m) an IgG4 antibody.

3. A composition comprising said isolated antibody of claim 1 in a pharmaceutically acceptable carrier.

* * * * *

UNITED STATES PATENT AND TRADEMARK OFFICE
CERTIFICATE OF CORRECTION

PATENT NO. : 7,585,500 B2
APPLICATION NO. : 11/281266
DATED : September 8, 2009
INVENTOR(S) : Foltz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 826 days.

Signed and Sealed this

Fourteenth Day of September, 2010

David J. Kappos
*Director of the United States Patent and Trademark Office*